(12) United States Patent
Lichter et al.

(10) Patent No.: US 11,369,566 B2
(45) Date of Patent: *Jun. 28, 2022

(54) CONTROLLED RELEASE ANTIMICROBIAL COMPOSITIONS AND METHODS FOR THE TREATMENT OF OTIC DISORDERS

(71) Applicants: ALK-ABELLÓ, INC., Bedminster, NJ (US); The Regents of the University of California, Oakland, CA (US)

(72) Inventors: Jay Lichter, Rancho Santa Fe, CA (US); Andrew M. Trammel, Olathe, KS (US); Fabrice Piu, San Diego, CA (US); Qiang Ye, San Diego, CA (US); Luis A. Dellamary, San Marcos, CA (US); Carl Lebel, Malibu, CA (US); Jeffrey P. Harris, La Jolla, CA (US)

(73) Assignees: ALK-ABELLÓ, INC., Bedminster, NJ (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/710,727

(22) Filed: Sep. 20, 2017

(65) Prior Publication Data

US 2018/0161271 A1    Jun. 14, 2018

Related U.S. Application Data

(63) Continuation of application No. 14/741,092, filed on Jun. 16, 2015, now Pat. No. 9,867,778, which is a continuation of application No. 13/645,126, filed on Oct. 4, 2012, now Pat. No. 9,233,068, which is a continuation of application No. 12/506,127, filed on Jul. 20, 2009, now Pat. No. 8,318,817, which is a continuation-in-part of application No. 12/466,310, filed on May 14, 2009, now Pat. No. 8,030,297, and a continuation-in-part of application No. 12/427,663, filed on Apr. 21, 2009, now Pat. No. 9,132,087.

(60) Provisional application No. 61/140,033, filed on Dec. 22, 2008, provisional application No. 61/101,112, filed on Sep. 29, 2008, provisional application No. 61/094,384, filed on Sep. 4, 2008, provisional application No. 61/083,871, filed on Jul. 25, 2008, (Continued)

(51) Int. Cl.
| | |
|---|---|
| A61K 9/00 | (2006.01) |
| A61K 8/04 | (2006.01) |
| A61K 9/06 | (2006.01) |
| A61K 31/43 | (2006.01) |
| A61K 31/7036 | (2006.01) |
| A61K 9/14 | (2006.01) |
| A61P 27/16 | (2006.01) |
| A61K 9/10 | (2006.01) |
| A61K 47/34 | (2017.01) |
| A61K 9/16 | (2006.01) |
| A61K 31/522 | (2006.01) |
| A61K 31/573 | (2006.01) |
| A61K 47/02 | (2006.01) |
| A61K 47/10 | (2017.01) |
| A61K 31/496 | (2006.01) |

(52) U.S. Cl.
CPC ............ *A61K 9/0046* (2013.01); *A61K 8/042* (2013.01); *A61K 9/0019* (2013.01); *A61K 9/0024* (2013.01); *A61K 9/06* (2013.01); *A61K 9/10* (2013.01); *A61K 9/1641* (2013.01); *A61K 31/43* (2013.01); *A61K 31/496* (2013.01); *A61K 31/522* (2013.01); *A61K 31/573* (2013.01); *A61K 31/7036* (2013.01); *A61K 47/02* (2013.01); *A61K 47/10* (2013.01); *A61K 47/34* (2013.01); *A61K 9/14* (2013.01); *A61P 27/16* (2018.01)

(58) Field of Classification Search
CPC .... A61K 31/43; A61K 31/496; A61K 31/522; A61K 31/573; A61K 31/7036; A61K 47/02; A61K 47/10; A61K 47/34; A61K 8/042; A61K 9/0019; A61K 9/0024; A61K 9/0046; A61K 9/06; A61K 9/10; A61K 9/14; A61K 9/1641; A61P 27/16
See application file for complete search history.

(56) References Cited

U.S. PATENT DOCUMENTS

| | | |
|---|---|---|
| 4,188,373 A | 2/1980 | Krezanoski |
| 4,268,519 A | 5/1981 | Turner |
| 4,478,822 A | 10/1984 | Haslam et al. |

(Continued)

FOREIGN PATENT DOCUMENTS

| | | |
|---|---|---|
| CN | 101664381 A | 3/2010 |
| EP | 0551626 A1 | 7/1993 |

(Continued)

OTHER PUBLICATIONS

AAFP, AAO and AAP. Otitis Media with Effusion. Pediatrics 113(5):1412-1429 (2004).

(Continued)

*Primary Examiner* — Sarah Pihonak
(74) *Attorney, Agent, or Firm* — Procopio, Cory, Hargreaves & Savitch LLP

(57) ABSTRACT

Disclosed herein are compositions and methods for the treatment of otic diseases or conditions with antimicrobial agent compositions and formulations administered locally to an individual afflicted with an otic disease or condition, through direct application of these compositions and formulations onto or via perfusion into the targeted auris structure(s).

9 Claims, 5 Drawing Sheets

Related U.S. Application Data provisional application No. 61/082,450, filed on Jul. 21, 2008.

(56) References Cited

U.S. PATENT DOCUMENTS

| | | | |
|---|---|---|---|
| 4,938,763 A | 7/1990 | Dunn et al. | |
| 4,968,507 A | 11/1990 | Zentner et al. | |
| 5,033,252 A | 7/1991 | Carter | |
| 5,039,382 A | 8/1991 | Suzuki et al. | |
| 5,052,558 A | 10/1991 | Carter | |
| 5,292,516 A | 3/1994 | Viegas et al. | |
| 5,323,907 A | 6/1994 | Kalvelage | |
| 5,324,519 A | 6/1994 | Dunn et al. | |
| 5,401,741 A | 3/1995 | Sato et al. | |
| 5,421,818 A | 6/1995 | Arenberg | |
| 5,474,529 A | 12/1995 | Arenberg | |
| 5,476,446 A | 12/1995 | Arenberg | |
| 5,503,848 A | 4/1996 | Perbellini et al. | |
| 5,702,716 A | 12/1997 | Dunn et al. | |
| 5,744,153 A | 4/1998 | Yewey et al. | |
| 5,861,174 A | 1/1999 | Stratton et al. | |
| 5,990,194 A | 11/1999 | Dunn et al. | |
| 6,004,573 A | 12/1999 | Rathi et al. | |
| 6,045,528 A | 4/2000 | Arenberg et al. | |
| 6,117,949 A | 9/2000 | Rathi et al. | |
| 6,139,870 A | 10/2000 | Verrecchia | |
| 6,177,434 B1 | 1/2001 | Kopke et al. | |
| 6,201,065 B1 | 3/2001 | Pathak et al. | |
| 6,201,072 B1 | 3/2001 | Rathi et al. | |
| 6,239,113 B1 | 5/2001 | Dawson et al. | |
| 6,284,804 B1 | 9/2001 | Singh et al. | |
| 6,287,588 B1 | 9/2001 | Shih et al. | |
| 6,316,011 B1 | 11/2001 | Ron et al. | |
| 6,359,016 B2 | 3/2002 | Singh et al. | |
| 6,392,036 B1 | 5/2002 | Karlsson et al. | |
| 6,488,952 B1 | 12/2002 | Kennedy et al. | |
| 6,509,327 B1 | 1/2003 | Cagle et al. | |
| 6,589,549 B2 | 7/2003 | Shih et al. | |
| 6,649,621 B2 | 11/2003 | Kopke et al. | |
| 6,740,664 B2 | 5/2004 | Cagle et al. | |
| 7,001,615 B1 | 2/2006 | Singh et al. | |
| 7,018,645 B1 | 3/2006 | Piao et al. | |
| 7,220,431 B2 | 5/2007 | Sawchuk et al. | |
| 7,524,834 B2 | 4/2009 | Karlsson et al. | |
| 8,030,297 B2 | 10/2011 | Lighter et al. | |
| 8,318,817 B2 | 11/2012 | Lighter et al. | |
| 8,349,353 B2 | 1/2013 | Lighter et al. | |
| 8,390,018 B2 | 3/2013 | Jang | |
| 8,399,018 B2 | 3/2013 | Lighter et al. | |
| 8,496,957 B2 | 7/2013 | Lighter et al. | |
| 8,648,119 B2 | 2/2014 | Lighter et al. | |
| 8,784,870 B2 | 7/2014 | Lighter et al. | |
| 8,846,770 B2 | 9/2014 | Lighter et al. | |
| 9,034,294 B1 | 5/2015 | Harrison | |
| 9,132,087 B2 | 9/2015 | Lighter et al. | |
| 9,205,048 B2 | 12/2015 | Lighter et al. | |
| 9,233,068 B2 | 1/2016 | Lighter et al. | |
| 9,486,405 B2 | 11/2016 | Piu et al. | |
| 9,603,796 B2 | 3/2017 | Lighter et al. | |
| 2001/0034339 A1 | 10/2001 | Singh et al. | |
| 2002/0076441 A1 | 6/2002 | Shih et al. | |
| 2002/0099171 A1 | 7/2002 | De Robertis et al. | |
| 2002/0107238 A1 | 8/2002 | Bandyopadhyay et al. | |
| 2002/0169142 A1 | 11/2002 | Jafari et al. | |
| 2003/0092776 A1 | 5/2003 | Ron et al. | |
| 2003/0139382 A1 | 7/2003 | Wall et al. | |
| 2003/0185872 A1 | 10/2003 | Kochinke | |
| 2003/0229333 A1 | 12/2003 | Ashton et al. | |
| 2004/0022853 A1 | 2/2004 | Ashton et al. | |
| 2004/0082509 A1 | 4/2004 | Bonny | |
| 2004/0101506 A1 | 5/2004 | Fust | |
| 2004/0101560 A1 | 5/2004 | Sawchuk et al. | |
| 2004/0204471 A1 | 10/2004 | Seibert | |
| 2004/0214753 A1* | 10/2004 | Britten .................. | A61P 9/00 514/152 |
| 2004/0248803 A1 | 12/2004 | Nusse et al. | |
| 2005/0147585 A1 | 7/2005 | Schwarz | |
| 2005/0159369 A1 | 7/2005 | Lane | |
| 2005/0214338 A1 | 9/2005 | Guitton et al. | |
| 2005/0287200 A1 | 12/2005 | Murthy et al. | |
| 2006/0013858 A1 | 1/2006 | Trune | |
| 2006/0034889 A1 | 2/2006 | Jo et al. | |
| 2006/0046970 A1 | 3/2006 | Bowman et al. | |
| 2006/0063802 A1 | 3/2006 | Guitton et al. | |
| 2006/0122159 A1* | 6/2006 | Huq .................. | A61K 31/496 514/171 |
| 2006/0257488 A1 | 11/2006 | Hubbard | |
| 2006/0264897 A1 | 11/2006 | Lobl et al. | |
| 2006/0269602 A1 | 11/2006 | Dasch et al. | |
| 2007/0048338 A1 | 3/2007 | Ladd | |
| 2007/0110788 A1 | 5/2007 | Hissong et al. | |
| 2007/0138020 A1 | 6/2007 | Balagopal et al. | |
| 2007/0167918 A1 | 7/2007 | Reed et al. | |
| 2007/0178051 A1 | 8/2007 | Pruitt et al. | |
| 2008/0103118 A1 | 5/2008 | Clement et al. | |
| 2008/0124385 A1 | 5/2008 | Campbell | |
| 2008/0181952 A1 | 7/2008 | Vogel et al. | |
| 2008/0318918 A1 | 12/2008 | Campbell et al. | |
| 2009/0093449 A1 | 4/2009 | Bowman et al. | |
| 2009/0156566 A1 | 6/2009 | Wall et al. | |
| 2009/0246255 A1 | 10/2009 | Meyer | |
| 2009/0297533 A1 | 12/2009 | Lighter et al. | |
| 2009/0324552 A1 | 12/2009 | Lighter et al. | |
| 2009/0325938 A1 | 12/2009 | Lighter et al. | |
| 2010/0015228 A1 | 1/2010 | Lighter et al. | |
| 2010/0015263 A1 | 1/2010 | Lighter et al. | |
| 2010/0016218 A1 | 1/2010 | Lighter et al. | |
| 2010/0016450 A1 | 1/2010 | Lighter et al. | |
| 2010/0021416 A1 | 1/2010 | Lighter et al. | |
| 2010/0036000 A1 | 2/2010 | Lighter et al. | |
| 2010/0197800 A1 | 8/2010 | Friedman et al. | |
| 2010/0273864 A1 | 10/2010 | Lighter et al. | |
| 2011/0166060 A1 | 7/2011 | Simons et al. | |
| 2012/0277199 A1 | 11/2012 | Ye et al. | |
| 2013/0178801 A1 | 7/2013 | Branch et al. | |
| 2013/0216609 A1 | 8/2013 | Lighter et al. | |
| 2013/0306565 A1 | 11/2013 | Davis | |
| 2014/0239221 A1 | 8/2014 | Harrison et al. | |
| 2015/0045739 A1 | 2/2015 | Nickel et al. | |
| 2016/0000948 A1 | 1/2016 | Coleman et al. | |
| 2016/0038594 A1 | 2/2016 | Lighter et al. | |
| 2016/0067179 A1 | 3/2016 | Lighter et al. | |
| 2016/0230250 A1 | 8/2016 | Chung et al. | |
| 2017/0027930 A1 | 2/2017 | Piu et al. | |
| 2018/0085304 A1 | 3/2018 | Lebel et al. | |

FOREIGN PATENT DOCUMENTS

| | | |
|---|---|---|
| EP | 2567710 A1 | 3/2013 |
| FR | 3034781 A1 | 10/2016 |
| JP | H01258620 A | 10/1989 |
| JP | H04225914 A | 8/1992 |
| JP | H07215877 A | 8/1995 |
| JP | H11500740 A | 1/1999 |
| JP | 2000514811 A | 11/2000 |
| JP | 2001520188 A | 10/2001 |
| JP | 2003510259 A | 3/2003 |
| JP | 2004507450 A | 3/2004 |
| JP | 2004536836 A | 12/2004 |
| JP | 2005504804 A | 2/2005 |
| JP | 2006097031 A | 4/2006 |
| JP | 2006111585 A | 4/2006 |
| JP | 2011518195 A | 6/2011 |
| JP | 2013508381 A | 3/2013 |
| WO | WO-9515152 A1 | 6/1995 |
| WO | WO-9738698 A1 | 10/1997 |
| WO | WO-9924051 A2 | 5/1999 |
| WO | WO-9932151 A1 | 7/1999 |
| WO | WO-9932152 A2 | 7/1999 |
| WO | WO-0007603 A2 | 2/2000 |
| WO | WO-0050005 A1 | 8/2000 |
| WO | WO-0176558 A1 | 10/2001 |
| WO | WO-02056890 A1 | 7/2002 |
| WO | WO-03005961 A2 | 1/2003 |

(56) References Cited

FOREIGN PATENT DOCUMENTS

| | | |
|---|---|---|
| WO | WO-03017990 A2 | 3/2003 |
| WO | WO-03034979 A2 | 5/2003 |
| WO | WO-03051375 A1 | 6/2003 |
| WO | WO-03071986 A2 | 9/2003 |
| WO | WO-2004050021 A2 | 6/2004 |
| WO | WO-2006026570 A2 | 3/2006 |
| WO | WO-2006029074 A2 | 3/2006 |
| WO | WO-2006078886 A2 | 7/2006 |
| WO | WO-2006099325 A2 | 9/2006 |
| WO | WO-2006102964 A2 | 10/2006 |
| WO | WO-2007031098 A1 | 3/2007 |
| WO | WO-2007031280 A2 | 3/2007 |
| WO | WO-2007034989 A1 | 3/2007 |
| WO | WO-2007037874 A2 | 4/2007 |
| WO | WO-2007037886 A2 | 4/2007 |
| WO | WO-2007038949 A1 | 4/2007 |
| WO | WO-2008001341 A1 | 1/2008 |
| WO | WO-2008073938 A2 | 6/2008 |
| WO | WO-2008076556 A2 | 6/2008 |
| WO | WO-2008125872 A1 | 10/2008 |
| WO | WO-2009139924 A2 | 11/2009 |
| WO | WO-2009142719 A2 | 11/2009 |
| WO | WO-2010011609 A2 | 1/2010 |
| WO | WO-2015031393 A1 | 3/2015 |
| WO | WO-2018053173 A1 | 3/2018 |
| WO | WO-2018064164 A1 | 4/2018 |

OTHER PUBLICATIONS

Ahn et al. Lipoic acid rescues DBA mice from early-onset age-related hearing impairment. Neuroreport 19(13):1265-1269 (2008).
Ah-Tye et al. Otorrhea in Young Children After Tympanostomy-Tube Placement for Persistent Middle-Ear Effusion: Prevalence, Incidence, and Duration. Pediatrics 107(6):1251-1258 (2001).
Arnold et al. Novel slow- and fast-type drug release round-window microimplants for local drug application to the cochlea: an experimental study in guinea pigs. Audiol Neurootol 10(1):53-63 (2005).
Auris Medical. Press release reporting initiating of phase I/II clinical trial with AM-101. (1 pg.) (Feb. 22, 2007).
Auris Medical press release reporting results of phase I/II clinical trial with AM-111. (1 pg.)(Jun. 21, 2006).
Battaglia et al. Combination therapy (intratympanic dexamethasone + high-dose prednisone taper) for the treatment of idiopathic sudden sensorineural hearing loss. Otol Neurotol 29(4):453-460 (2008).
Bhoyar et al. A Noval Thermoreversible Phase transition System With Flux Enhancers For Opthalmic Application. Int J Pharm Pharm Sci. 3(4):367-370 (2011).
Bird et al. Intratympanic versus intravenous delivery of methylprednisolone to cochlear perilymph. Otology & Neurotology 28(8):1124-1130 (2007).
Bovo et al. Immune-mediated inner ear disease. Acta Oto-Laryngologica 126:1012-1021 (2006).
Campbell et al. Oral-D-methionine (MRX-1024) significantly protects against cisplatin-induced hearing loss: a phase II study in humans. Abst 32nd Ann MidWinter Res Meeting, ARO Abstracts 32:7 (Feb. 14-19, 2009).
Chang et al. Prolonged Antifungal Effects of Clotrimazole-Containing Mucoadhesive Thermosensitive Gels on Vaginitis. Journal of Controlled Release. Elsevier, Amsterdam, NL. 82(1):39-50 (2002).
Chen et al. Design and preparation of thermosensitive in situ gel of dexamethasone sodium phosphate. J Guangdong Coll Pharm 23(5):518-521 (2007) (English abstract).
Chen et al. Estrogen-related receptor beta/NR3B2 controls epithelial cell fate and endolymph production by the stria vascularis. Dev Cell 13(3):325-337 (2007).
Chen et al. Evaluation of thermosensitive in situ gel using dynamic rheological experiment, Chin Pharm J 43(6):444-447 (2008) (English abstract).
Chen et al. In vivo Distribution and Pharmacokinetics of Dexamethasone Acetate Nanoparticles Thermosensitive in situ Gel Following Intratympanic Injection. Chin. J. Otorhinolaryngol Head Neck Surg 42:533-534 (2007).
Chen et al. In vivo distribution and pharmacokinetics of dexamethasone sodium phosphate thermosensitive in situ gel following intratympanic injection. Sichuan Da Xue Xue Bao Yi Xue Ban 37(3):456-459 (2006) (English translation).
Chen et al. Preliminary study on brain-targeted drug delivery via inner ear. Acta Pharmaceutica Sinica 42:1102-1106 (2007) (English Abstract).
Chen et al. Preparation and characterization of dexamethasone acetate-loaded solid lipid nanoparticles. Chinese J Pharm 39(4):261-264 (2008) (English abstract).
Chen et al. Study on dexamethasone thermosensitive in situ gel for treating deafness. Chin Pharm J 41(9):685-688 (2006) (English abstract).
Choi et al. A novel class of phosphonate nucleosides. 9-[(1-phosphonomethoxycyclopropyl)methyl]guanine as a potent and selective anti-HBV agent. J Med Chem. (11):2864-2869 (May 20, 2004).
Choi et al. Biological roles of lysophospholipid receptors revealed by genetic null mice: an update. Biochim Biophys Acta. 1781(9):531-539 (2008).
Choi et al. Effect of additives on the physicochemical properties of liquid suppository bases. International Journal of Pharmaceutics. 190(1):13-19 (1999).
Choi et al. Enhanced production of insulin-like growth factor I fusion protein in *Escherichia coli* by coexpression of the down-regulated genes identified by transcriptome profiling. Applied And Environmental Microbiology. 69(8):4737-4742 (2003).
Choi et al. Regulation of keratin 19 gene expression by estrogen in human breast cancer cells and identification of the estrogen responsive gene region. Mol Cell Endocrinol 164(1-2):225-237 (2000).
Choi et al. Synthesis and antiviral activity of novel exomethylene cyclopropyl nucleosides. Nucleosides Nucleotides Nucleic Acids. 20(4-7):1059-1062 (Apr.-Jul. 2001).
Choi et al. The design and evaluation of heparin-binding foldamers. Angew Chem Int Ed Engl. 44(41):6685-6689 (2005).
Choi et al. Use of combinatorial genetic libraries to humanize N-linked glycosylation in the yeast Pichia pastoris. PNAS USA 100(9):5022-5027 (2003).
CIPRODEX. product label 2009 (3 pgs.).
Co-pending U.S. Appl. No. 15/717,467, filed Sep. 27, 2017.
Database WPI. Section Ch. Week 201029 Thomson Scientific. London. Class A11. Preparation of Gelatin Sustained-release Composition for Treating Mastitis of Milk Cow Comprises Spraying Aqueous Solution of Ciprofloxacin and Chitosan Film Polymer to try and Distributing into Aqueous Solution of Poloxamer. download Feb. 5, 2014, 2 pages.
Dellamary et al. Assessing and optimizing osmolality of poloxamer 407 hydrogel formulations for sustained inner ear drug delivery. Poster. 2010 AAPS National Biotechnology Conference in San Francisco (1 pg.).
Dellamary et al. Development of poloxamer hydrogel formulations for sustained inner ear drug delivery. Poster. 2010 AAPS National Biotechnology Conference in San Francisco (1 pg.).
Dellamary et al. Novel poloxamer hydrogel formulations for sustained drug delivery to the middle ear. Abstract. 2010 Annual Meeting in New Orleans, Nov. 14-18 (1 pg.).
Dellamary et al. Novel poloxamer hydrogel formulations for sustained inner ear drug delivery. Abstract. Controlled Release Society 37th Annual Meeting and Exposition in Portland Jul. 10-14, 2010 (2 pgs.).
Derin et al. The effects of L-carnitine on presbyacusis in the rat model. Clin Otolaryngol Allied Sci 29(3):238-241( 2004).
Dourmishev et al. Waardenburg syndrome. International Journal of Dermatology 38:656-663 (1999).
Dumortier et al. A Review of Poloxamer 407 Pharmaceutical and Pharmacological Characteristics. Pharm Res 23(12):2709-2728 (2006).
Elgen. Remington's Pharmaceuticals Sciences. 17th ed. pp. 1836-1837 (1985).
Endo et al. Novel strategy for treatment of inner ears using a biodegradable gel. Laryngoscope 115(11):2016-2020 (2005).

(56) References Cited

OTHER PUBLICATIONS

Fedder et al. Remington: The Science and Practice of Pharmacy. Lippincott Williams and Wilkins 21 ed. pp. 1992-1993 (2005).
Feng et al. Effect of Poloxamer 407 on the cochlear orphology and hearing function after perfusion in round window: experiment with guinea pigs. National Medical Journal of China 87(32):2289-2291 (2007) (English Translation).
Feng et al. Effect of poloxamer 407 on the middle ear and inner ear after regional perfusion in guinea pigs. Zhonghua Er Bi Yan Hou Tou Jing Wai Ke Za Zhi 42(6):443-446 (2007) (English translation).
Fernandez et al. Self-curing controlled release systems for steroids. Application of prednisolone-based polymeric systems to ear diseases. Biomaterials 26(16):3311-3318 (2005).
Friedman et al. GRM7 variants confer susceptibility to age-related hearing impairment. Hum Mol Genet 18(4):785-796. (2009).
Garcia-Berrocal et al. Does the serological study for viral infection in autoimmune inner ear disease make sense? O.R.L. 70:16-20 (2008).
Garduno-Anaya et al. Dexamethasone inner ear perfusion by intratympanic injection in unilateral Ménière's disease: a two-year prospective, placebo-controlled, double-blind, randomized trial. Otolaryngol Head Neck Surg 133(2):285-294 (2005).
Gubbels et al. Functional auditory hair cells produced in the mammalian cochlea by in utero gene transfer. Nature 455(7212):537-541 (2008).
Guyot et al. Intratympanic application of an antiviral agent for the treatment of Meniere's disease. ORL J Otorhinolaryngol Relat Spec 70(1 ):21 -6; discussion 26-27 (2008).
Hall et al. Anti-Pneumocystis activities of aromatic diamidoxime prodrugs. Antimicrobial Agents & Chemother. 42(3):666-674 (1998).
Hargunani et al. Intratympanic injection of dexamethasone: time course of inner ear distribution and conversion to its active form. Otol Neurotol 27(4):564-569 (2006).
Harris. Immunology of the inner ear: Response of the inner ear to antigen challenge. Otorhinolaryngology Head and Neck Surgery. 91:18-32 (1983).
Harris et al. Prevention of noise-induced hearing loss with Src-PTK inhibitors. Hear Res 208(1-2): 14-25 (2005).
Harris et al. Treatment of corticosteroid-responsive autoimmune inner ear disease with methotrexate: a randomized controlled trial. JAMA 290(14):1875-1883 (2003).
Hill et al. Cisplation-lnduced Ototoxicity: Effect of Intratympanic Dexamethasone Injections. Otol. Neurotol. 29(7):1005-1011 (2008).
Hoffer et al. Transtympanic management of tinnitus. Otolaryngol Clin North Am 36(2):353-358 (2003).
Hoshino et al. The non-steroidal anti-inflammatory drugs protect mouse cochlea against acoustic injury. Tohoku J Exp Med 216(1):53-59 (2008).
Inaoka et al. Local application of hepatocyte growth factor using gelatin hydrogels attenuates noise-induced hearing loss in guinea pigs. Acta Otolaryngol 129(4):453-457 (2009).
Jeong et al. Biodegradable block copolymers as injectable drug-delivery systems. Nature 388:860-862 (1997).
Jeong et al. Drug release from biodegradable injectable thermosensitive hydrogel of PEG-PLGA-PEG triblock copolymers. Journal of Controlled Release 63:155-163 (2000).
Jeong et al. Thermosensitive sol-gel reversible hydrogels. Advanced Drug Delivery Reviews 54:37-51 (2002).
Jia et al. Intratympanic dexamethasone for refractory sudden deafness. Lin Chung Er Bi Yan Hou Tou Jing Wai Ke Za Zhi 22(7):309-311 (2008) (English translation).
Karolewicz et al. Thermosensitive polymers in drug form technology H. Possibilities of use of thermosensitive polymers as active substance carriers. Polimery W Medycynie 38(1):15-26 (2008) (English abstract).
Kazama et al. Lithium effectively complements vasopressin V2 receptor antagonist in the treatment of hyponatraemia of SIADH rats. Nephrol Dial Transplant 22(1):68-76 (2007).
Keithley et al. GDNF protects the cochlea against noise damage. Neuroreport 9(10):2183-2187 (1998).
Khoo et al. Formulations fortrans-tympanic antibiotic delivery. Biomaterials 34:1281-1288 (2013).
Kim et al. Effects of tumor necrosis factor alpha antagonist, platelet activating factor antagonist, and nitric oxide synthase inhibitor on experimental otitis media with effusion. Ann Otol Rhinol Laryngol 115(8):617-623 (2006).
Kitahara et al. Up-regulation of cochlear aquaporin-3 mRNA expression after intra-endolymphatic sac application of dexamethasone. Neurol Res. 25(8):865-870 (2003).
Lamm et al. The effect of prednisolone and non-steroidal anti-inflammatory agents on the normal and noise-damaged guinea pig inner ear. Hear Res 115(1-2):149-161 (1998).
Lavreysen et al. Therapeutic potential of group III metabotropic glutamate receptors. Curr Med Chem 15(7):671-84 (2008).
Lee et al. Novel therapy for hearing loss: delivery of insulin-like growth factor 1 to the cochlea using gelatin hydrogel. Otol Neurotol 28(7):976-981 (2007).
Lee et al. Regional delivery of vancomycin using pluronic F-127 to inhibit methicillin resistant *Staphylococcus aureus* (MRSA) growth in chronic otitis media in vitro and in vivo. J Control Release 96(1):1-7 (2004).
Letter indicating that an opposition brief was filed in connection with Peruvian Patent Application No. 000959-2009/DIN (2 pgs.) (Aug. 20, 2010).
Lieberthal et al. The Diagnosis and Management of Acute Otitis Media. Pediatrics 131(3):e964-e999 (2013).
Lin et al. In Vitro Evaluation of Lysozyme-loaded Microspheres in Thermosensitive Methylcellulose-base Hydrogel. Chin J Chem Eng 15(4):566-572 (2007).
Liu et al. Permeability of different Dexamethasone drugs through round window membrane. Zhonghua Er Bi Yan Hou Tou Jing Wai Ke Za Zhi 41(3):211-215 (2006) (English abstract).
Lloyd et al. A patient with tinnitus. Clin Otolaryngology 33:25-28 (2008).
Majithiya et al. Thermoreversible-mucoadhesive Gel for Nasal Delivery of Sumatriptan. AAPS PharmSciTech 7(3):E1-E7 (2006).
Mansour et al. Ocular Poloxamer-Based Ciprofloxacin Hydrochloride in Situ Forming Gels. Drug Development and Industrial Pharmacy. 34(7):744-752 (2008).
McCarthy et al. Alport syndrome: a review. Clinical Eye and Vision Care 12:139-150 (2000).
McGuinness et al. Exogenous BDNF rescues rat spiral ganglion neurons in vivo. Otol Neurotol 26(5):1064-1072 (2005).
Meltser et al. Estrogen receptor beta protects against acoustic trauma in mice. J Clin Invest 118(4): 1563-1570 (2008).
Miceli et al. Molecular pharmacology and therapeutic potential of neuronal Kv7—modulating drugs. Curr Opin Pharmacol 8(1):65-74 (2008).
Mitsukawa et al. A selective metabotropic glutamate receptor 7 agonist: activation of receptor signaling via an allosteric site modulates stress parameters in vivo. PNAS USA 102(51):18712-18717 (2005).
Miyazaki et al. Thermally reversible xyloglucan gels as vehicles for rectal drug delivery. Journal of Controlled Release (Elsevier, Amsterdam, NL) 56(1-3):75-83 (1998).
Morden et al. Topical Fluoroquinolones for Eye and Ear. Am Fam Physician 62(8):1 870-1876 (2000).
MOSTAFA Transtympanic Membrane Delivery of Antibiotics-Pharmacokinetic Studies in Chinchillas. Dissertation submitted to the Graduate School of the University of Minnesota in (Mar. 2007).
Nakagawa et al. Local drug delivery to inner ear for treatment of hearing loss. Curr Drug Ther 3:143-147 (2008).
Nance et al. The Genetics of Deafness. Mental Retardation and Developmental Disabilities 9:109-119 (2003).
Nishimaki et al. Reduction of metabotropic glutamate receptor-mediated heterosynaptic inhibition of developing MNTB-LSO inhibitory synapses. Eur J Neurosci 26(2):323-330 (2007).
Nouvian et al. Degeneration of sensory outer hair cells following pharmacological blockade of cochlear KCNQ channels in the adult guinea pig. Eur J Neurosci 17(12):2553-2562 (2003).
Oldstone. Virus-induced autoimmunity: molecular mimicry as a route to autoimmune disease. J. Autoimmune 2(suppl):187-194 (1989).

(56) References Cited

OTHER PUBLICATIONS

Oliveira et al. Viral etiology for inner ear diseases: proven, unproven, unlikely. ORL 70:42-51 (2008).
Pappas et al. Topical Antibiotic Ear Drops: Are They Safe? Int J Clin Pract. 60:1115-1119 (2006).
Park et al. Effect of inhibitor of tumor necrosis factor-alpha and oxatomide on immune mediated otitis media. Laryngoscope 116(9):1642-1646 (2006).
Parnes et al. Corticosteroid pharmacokinetics in the inner ear fluids: an animal study followed by clinical application. Laryngoscope 109(7 Pt 2 Supplement No. 91):1-17 (1999).
Patent Interference No. 106,030. Decisions on Motions §41.124 entered Jan. 26, 2017 (47 pgs).
Patent Interference No. 106,030. Judgment §41.127 entered Jan. 26, 2017 (3 pgs).
Patent Interference No. 106,030. Redeclaration 37 CFR §41.203(c) entered on Jan. 26, 2017 (4 pgs.).
Paulson et al. A novel controlled local drug delivery system for inner ear disease. Laryngoscope 118(4):706-711 (2008).
PCT/US2008/061330 International Search Report dated Jul. 31, 2008.
PCT/US2009/051172 International Search Report dated Feb. 18, 2010.
PCT/US2009/067552 International Search Report dated Aug. 18, 2010.
PCT/US2010/053214 International Search Report dated Jul. 1, 2011.
PCT/US2014/052754 International Preliminary Report on Patentability dated Mar. 10, 2016.
PCT/US2014/52754 International Search Report and Written Opinion dated Nov. 4, 2014.
Pelton et al. Recent Advances in Otitis Media. Pediatric Infectious Disease Journal 28(10):S133-S137 (2009).
Peng et al. Clinical investigation of different routes of administration of dexamethasone on sudden deafness. Lin Chung Er Bi Yan Hou Tou Jing Wai Ke Za Zhi 22(10):442-445. (2008) (English translation).
Piu et al. OTO-104: A Sustained-Release Dexamethasone Hydrogel for the Treatment of Otic Disorders. Otol & Neurology 32(1):171-179 (2011).
Piu et al. OTO-104: A Sustained-Release Dexamethasone Hydrogel formulation for the treatment of Meniere's disease, Oral Presentation title: Recent Topics in Meniere's disease treatment, Nov. 16, 2010 (1 pg.).
Piu et al. Towards predicting human inner ear pharmacokinetics: allometric scaling using guinea pigs and sheep. Abstract. ARO Meeting, Feb. 6-10, 2010 (1 pg).
Plontke et al. Rapid clearance of methylprednisolone after intratympanic application in humans. Comment on: Bird PA. Begg EJ. Zhang M et al. Intratympanic versus intravenous delivery of methylprednisolone to cochlear perilymph. Otol Neurotol (2007); 28:1124-30. Otol Neurotol 29(5):732-733 (2008).
Pondugula et al. Glucocorticoid regulation of genes in the amiloride-sensitive sodium transport pathway by semicircular canal duct epithelium of neonatal rat. Physiol Genomics 24(2):114-123 (2006).
Pondugula et al. Glucocorticoids stimulate cation absorption by semicircular canal duct epithelium via epithelial sodium channel. Am J Physiol Renal Physiol 286(6):F1127-1135 (2004).
Psillas et al. Potential efficacy of early treatment of acute acoustic trauma with steroids and piracetam after gunshot noise. Eur Arch Otorhinolaryngol 265(12):1465-1469 (2008).
Puel. Chemical synaptic transmission in the cochlea. Prog Neurobiol 47(6):449-476 (1995).
Qi et al. Development of a Poloxamer Analogs/Carbopol-based in situ Gelling and Mucoadhesive Ophthalmic Delivery System for Puerarin. International Journal of Pharmaceuticals. Elsevier BV. NL. 337(1-2):178-187 (2007).
Richard et al. Effects of sterilizing-grade filters on the physicochemical properties of onionlike vesicles. Int J Pharm 312(1-2):144-150 (2006).
Roland et al. Microbiology of Acute Otitis Media With Tympanostomy Tubes. Otolaryngology—Head and Neck Surgery 133(4):585-595 (2005).
Ross et al. Aqueous Solubilities of some variously Substituted Quinolone Antimicrobials. Int'l J of Pharm 63:237-250 (1990).
Salt et al. Distribution of Dexamethasone and Preservation of Inner Ear Function following Intratympanic Delivery of a Gel-Based Formulation. Audiology Neurology 16:323-335 (2011).
Salt et al. Local Inner Ear Drug Delivery and Pharmacokinetics. Drug Discovery Today NIH 10(19): 1299-1306 (2005).
Satoh et al. Tumor necrosis factor-alpha, an initiator, and etanercept, an inhibitor of cochlear inflammation. Laryngoscope 112:1627-1634 (2002).
Schoepp et al. Pharmacological agents acting at subtypes of metabotropic glutamate receptors. Neuropharmacology 38(10):1431-1476 (1999).
Schuknecht. Ablation therapy for the relief of Ménière's disease. Laryngoscope 66:859-870 (1956).
Seidman et al. Anti-intercellular adhesion molecule-1 antibody's effect on noise damage. Laryngoscope 119(4):707-712 (2009).
Shaikh et al. How do parents of preverbal children with acute otitis media determine how much ear pain their child is having? The Journal of Pain 11(12):1291-1294 (2010).
She et al. A short term study on the efficacies of intratympanic prednisolone and dexamethasone injection for subjective tinnitus. Lin Chung Er Bi Yan Hou Tou Jing Wai Ke Za Zhi 22(19):871-873 (2008) (English translation).
Shepherd et al. Neurotrophins and electrical stimulation for protection and repair of spiral ganglion neurons following sensorineural hearing loss. Hear Res 242(1-2):100-109 (2008).
Shin et al. Mucoadhesive and Physicochemical Characterization of Carbopol-Poloxamergels Containing Trimcinolone Acetonide. Drug Development and Industrial Pharmacy 26(3):307-312 (2000).
Shinohara et al. Neurotrophic factor intervention restores auditory function in deafened animals. PNAS USA 99(3):1657-1660 (2002).
Sismanis. Tinnitus. Curr Neurol Neurosci Rep. 1(5):492-499 (2001).
Song. Design and Synthesis of Factor Xa Inhibitors and their Prodrugs. Bioorganic & Medicinal Chemistry Letters 13:297-300 (2003).
Sun et al. In vitro permeability of round window membrane to transforming dexamethasone with delivery vehicles—a dosage estimation. Chin Med J 120(24):2284-2289 (2007) (English translation).
Synphora Ab. website printout for JB004/A 2009 (1 pg.).
Tabuchi et al. Hearing impairment in TRPV4 knockout mice. Neurosci Lett 382(3):304-308 (2005).
Taguchi et al. Expressions of aquaporin-2. vasopressin type 2 receptor, transient receptor potential channel vanilloid (TRPV)1. and TRPV4 in the human endolymphatic sac. Laryngoscope 117(4):695-698 (2007).
Tahera et al. NF-κB mediated glucocorticoid response in the inner ear after acoustic trauma. J Neurosci Res 83(6):1066-1076 (2006).
Takeda et al. Aquaporins as potential drug targets for Meniere's disease and its related diseases. Handb Exp Pharmacol 190:171-184 (2009).
Takeda et al. Decompression effects of erythritol on endolymphatic hydrops. Auris Nasus Larynx 36(2):146-151 (2009).
Takeda et al. The effects of V2 antagonist (OPC-31260) on endolymphatic hydrops. Hear Res 182(1-2):9-18. (2003).
Takemura et al. Direct inner ear infusion of dexamethasone attenuates noise-induced trauma in guinea pig. Hear Res 196(1-2):58-68 (2004).
Taktak et al. Assay of Pyrogens by lnterleukin-6 Release from Monocytic Cell Lines. J. Pharm. Pharmacol. 43:578-582 (1991).
Takumida et al. Nitric oxide in the inner ear. Cur Opin Neurol 15(1):11-15 (2002).
Tang et al. COUP-TFI controls Notch regulation of hair cell and support cell differentiation. Development 133(18):3683-3693 (2006).
The Royal National Institute for Deaf People (RNID) advertisement insert in Nature Reviews Drug Discovery, May 2009 (4 pgs.).
The U. S. Food and Drug Administration has provided regulatory guidance in the publication: Guidance for Industry: Sterile Drug Products Produced by Aseptic Processing, available at: http://www.fda.gov/cder/guidance/5882fn1.htm (Aug. 2003) (63 pgs.).

(56) References Cited

OTHER PUBLICATIONS

Thorne et al. Potential role of purinergic signalling in cochlear pathology. Audiol Neurootol 7(3):180-184 (2002).
U.S. Appl. No. 12/486,697 Office Action dated Apr. 26, 2011.
U.S. Appl. No. 12/504,553 Office Action dated Feb. 14, 2012.
U.S. Appl. No. 12/506,091 Office Action dated Feb. 22, 2012.
U.S. Appl. No. 13/500,971 Office Action dated Jan. 9, 2015.
U.S. Appl. No. 13/500,971 Office Action dated Jul. 17, 2014.
U.S. Appl. No. 13/500,971 Office Action dated Mar. 11, 2013.
U.S. Appl. No. 13/500,971 Office Action dated Mar. 24, 2016.
U.S. Appl. No. 13/500,971 Office Action dated May 29, 2015.
U.S. Appl. No. 13/500,971 Office Action dated Oct. 15, 2015.
U.S. Appl. No. 13/500,971 Office Action dated Sep. 18, 2013.
U.S. Appl. No. 13/645,126 Office Action dated Jan. 22, 2015.
U.S. Appl. No. 13/645,126 Office Action dated Jun. 12, 2015.
U.S. Appl. No. 13/848,636 Office Action dated May 14, 2015.
U.S. Appl. No. 14/469,408 Office Action dated May 6, 2016.
U.S. Appl. No. 14/469,408 Office Action dated October?, 2015.
U.S. Appl. No. 14/618,926 Office Action dated Mar. 24, 2015.
U.S. Appl. No. 14/618,926 Office Action dated May 4, 2015.
U.S. Appl. No. 14/741,092 Office Action dated May 31, 2016.
U.S. Appl. No. 14/741,092 Office Action dated Nov. 14, 2016.
U.S. Appl. No. 14/836,184 Office Action dated Aug. 5, 2016.
U.S. Appl. No. 14/836,184 Office Action dated Oct. 13, 2016.
U.S. Appl. No. 14/922,448 Office Action dated Apr. 15, 2016.
U.S. Appl. No. 14/922,448 office Action dated Sep. 6, 2016.
U.S. Appl. No. 15/264,107 Office Action dated Jan. 6, 2017.
Van Wijk et al. Local perfusion of the tumor necrosis factor alpha blocker infliximab to the inner ear improves autoimmune neurosensory hearing loss. Audiol Neurootol 11(6):357-365 (2006).
Varshosaz et al. Designing of a Thermosensitive Chitosan/Poloxamer In Situ Gel for Ocular Delivery of Ciprofloxacin. The Open Drug Delivery Journal 2:61-70 (2008).
Viegas et al. Osmotic behavior of poloxamer 407 and other non-ionic surfactants in aqueous solutions. Int. J. Pharm. 160:157-162 (1998).
Wang et al. A novel dual inhibitor of calpains and lipid peroxidation (BN82270) rescues the cochlea from sound trauma. Neuropharmacology 52(6):1426-1437 (2007).
Wang et al. Dose-dependent sustained release of dexamethasone in inner ear cochlear fluids using a novel local delivery approach. Audiol Neurotol 14:393-401 (2009).
Wang et al. Over-expression of X-linked inhibitor of apoptosis protein slows presbycusis in C57BL/6J mice. Neurobiol Aging 12 pgs. (2008).
Wang et al. Pharmacokinetic and safety profile of OTO-104: a sustained release dexamethasone hydrogel for inner ear delivery. Abstract. ARO Meeting, Feb. 6-10, 2010 (1 pg).
Wang et al. Pharmacokinetic and toxicity profile of the clinical candidate OTO-104: a sustained release dexamethasone hydrogel for inner ear delivery. 2010 Abstracts selected for AOS spring meeting. Las Vegas, NV. May 1-2, 2010 (2 pgs.).
Wang et al. Pharmacokinetic and toxicity profile of the clinical candidate OTO-104: a sustained release dexamethasone hydrogel for inner ear delivery. Abstract. COSM Meeting, May 1-2, 2010 (2 pgs.).
Wang et al. Pharmacokinetic and Toxicity Profile OTO-104: A Sustained Release Dexamethasone Hydrogel for Inner Ear Delivery. Abstract 644. Section: Q8. Feb. 8, 2010 (2 pgs.).
Wang et al. Pharmacokinetics of dexamethasone solution following intratympanic injection in guinea pig and sheep. Audiol Neurotol 16:233-241 (2011).
Wang et al. Principles of Inner Ear Sustained Release Following Intratympanic Administration, Laryngoscope 121:385-391 (2011).
Watanabe et al. Inhibition of inducible nitric oxide synthase lowers the cochlear damage by lipopolysaccharide in guinea pigs. Free Radic Res 32(4):363-370. (2000).
Watanabe et al. Nitric oxide synthase inhibitor reduces the apoptotic change in the cisplatin-treated cochlea of guinea pigs. Anticancer Drugs 11 (9):731-735 (2000).
Watanabe et al. Nitric oxide synthase inhibitor suppresses the ototoxic side effect of cisplatin in guinea pigs. Anticancer Drugs 11(5):401-406. (2000).
Yamamoto et al. Inhibition of Notch/RBP-J signaling induces hair cell formation in neonate mouse cochleas. J Mol Med 84(1):37-45 (2006).
Yang et al. Intratympanic immunosuppressives for prevention of inunune-mediated sensorineural hearing loss. Am J Otol 21(4):499-504 (2000).
Yildirim et al. Effect of intratympanic dexamethasone on noise-induced temporary threshold shift. Laryngoscope 115(7):1219-1222 (2005).
Zheng et al. Vanilloid receptors in hearing: altered cochlear sensitivity by vanilloids and expression of TRPV1 in the organ of corti. J Neurophysiol 90(1):444-455 (2003).
Zhou et al. Intratympanic administration of methylprednisolone reduces impact of experimental intensive impulse noise trauma on hearing. Acta Oto-Laryngologica 129:602-607 (2009).
Dohar. Tympanostomy Tubes: Not the Magic Bullet for Acute Otitis Media. Medscape (https://medscape.org/viewarticle/730700_print) (9 pgs) (2010).
External Acoustic Meatus Dec. 27, 2015 BodyMaps (2 pgs.).
PCT/US2017/051625 International Search Report and Written Opinion dated Jan. 2, 2018.
PCT/US2017/053715 International Search Report and Written Opinion dated Nov. 22, 2017.
U.S. Appl. No. 15/264,107 Office Action dated Nov. 2, 2018.
U.S. Appl. No. 15/622,633 Office Action dated Dec. 21, 2018.
U.S. Appl. No. 15/622,633 Office Action dated Jul. 13, 2018.
U.S. Appl. No. 15/622,633 Office Action dated Mar. 7, 2018.
U.S. Appl. No. 15/705,101 Office Action dated Apr. 5, 2018.
U.S. Appl. No. 15/705,101 Office Action dated Jan. 2, 2019.
U.S. Appl. No. 15/717,467 Office Action dated Sep. 24, 2018.
WebMD. What is Swimmer's Ear? © 2018. Accessed Sep. 29, 2018. Available from:<https://www.webmd.com/cold-and-flu/ear-infection/understanding-swimmer-ear-basics#1 (6 pgs) (2018).
Chung et al. Thermo-sensitive and biodegradable hydrogels based on stereocomplexed Pluronic multi-block copolymers for controlled protein delivery. J Control Release 127(1):22-30 (2008).
Ibrahim et al. Formulation and evaluation of quercetin in certain dermatological preparations. J Drug Del Sci Tech 17(6):431-436 (2007).
Liu et al. A small-molecule agonist of the Wnt signaling pathway. Angew Chem Int Ed Engl. 44(13):1987-1990 (2005).
Ribeiro et al. Solubilisation of griseofulvin, quercetin and rutin in micellar formulations of triblock copolymers E62P39E62 and E137S18E137. IntJ Pharm 378(1-2):211-214 (2009).
McCall et al. Drug delivery for treatment of inner ear disease: current state of knowledge. Ear Hear 31(2):156-165 (2010).
U.S. Appl. No. 15/622,633 Office Action dated Jun. 6, 2019.
U.S. Appl. No. 15/717,467 Office Action dated Jul. 10, 2019.

\* cited by examiner

CONTROLLED RELEASE ANTIMICROBIAL COMPOSITIONS AND METHODS FOR THE TREATMENT OF OTIC DISORDERS

CROSS-REFERENCE

This patent application is a Continuation of U.S. application Ser. No. 14/741,092, filed Jun. 16, 2015, now U.S. Pat. No. 9,867,778, which is a Continuation of U.S. Ser. No. 13/645,126, filed Oct. 4, 2012, now U.S. Pat. No. 9,233,068, which is a Continuation of U.S. application Ser. No. 12/506,127 filed on Jul. 20, 2009, now U.S. Pat. No. 8,318,817, which claims the benefit of U.S. Provisional Application Ser. No. 61/082,450 filed Jul. 21, 2008; U.S. Provisional Application Ser. No. 61/083,871 filed Jul. 25, 2008; U.S. Provisional Application Ser. No. 61/094,384 filed Sep. 4, 2008; U.S. Provisional Application Ser. No. 61/101,112 filed Sep. 29, 2008; U.S. Provisional Application Ser. No. 61/140,033 filed Dec. 22, 2008; this patent application is a Continuation-in-Part of U.S. application Ser. No. 12/427,663 filed Apr. 21, 2009, now U.S. Pat. No. 9,132,087 and a Continuation-in-Part of U.S. application Ser. No. 12/466,310 filed May 14, 2009, now U.S. Pat. No. 8,030,297; all of which are incorporated by reference herein in their entirety.

JOINT RESEARCH AGREEMENT

The claimed invention was made as a result of activities undertaken within the scope of a joint research agreement between Jay Benjamin Lichter, Benedikt K. Vollrath, Otonomy, Inc., and Avalon Ventures VIII GP, LLC that was in effect on or before the date the invention was made.

BACKGROUND OF THE INVENTION

Vertebrates have a pair of ears, placed symmetrically on opposite sides of the head. The ear serves as both the sense organ that detects sound and the organ that maintains balance and body position. The ear is generally divided into three portions: the outer ear, auris media (or middle ear) and the auris interna (or inner ear).

SUMMARY OF THE INVENTION

Described herein are compositions, formulations, manufacturing methods, therapeutic methods, uses, kits, and delivery devices for the controlled release of desired agents to at least one structure or region of the ear.

Disclosed herein are controlled release formulations for delivering at least one antimicrobial agent to the ear, or a target portion thereof, for the treatment of an otic disorder. In some embodiments, the antimicrobial agent is an antibacterial agent, an antifungal agent, an antiviral agent, an antiprotozoal agent, and/or an antiparasitic agent. In certain embodiments, the antimicrobial agent is a protein, an antibody, DNA, a carbohydrate, an inorganic compound, an organic compound, or combinations thereof. In certain embodiments, the antimicrobial agent is a small organic molecule.

In some embodiments, the target portion of the ear is the middle ear or auris media. In other embodiments, the target portion of the ear is the inner ear, or auris interna or a specific substructure therein. In other embodiments, the target portion of the ear is the middle ear, or auris media. In still other embodiments, the target portion of the ear is both the auris media and the auris interna. In some embodiments, the controlled release formulations further comprise a rapid or immediate release component for delivering an antimicrobial agent to the auris media and/or the auris interna. All formulations comprise excipients that are auris-media and/or auris-interna acceptable.

In certain embodiments, the controlled release composition further comprises an additional therapeutic agent, including an additional antimicrobial agent, an anti-inflammatory agent, a corticosteroid, a cytotoxic agent, an anti-TNF agent, a collagen, a gamma-globulin, an interferon, a platelet activator factor antagonist, a nitric oxide synthase inhibitor, or combinations thereof. In another aspect, the additional therapeutic agent is an immediate release or a controlled release agent.

Disclosed herein are controlled release formulations for delivering an antimicrobial agent to the ear. In some embodiments, the composition is administered so that the composition is in contact with the crista fenestrae cochleae, the round window or the tympanic cavity.

The auris formulations and therapeutic methods described herein have numerous advantages that overcome the previously-unrecognized limitations of formulations and therapeutic methods described in prior art.

Sterility

The environment of the inner ear is an isolated environment. The endolymph and the perilymph are static fluids and are not in contiguous contact with the circulatory system. The blood-labyrinth-barrier (BLB), which includes a blood-endolymph barrier and a blood-perilymph barrier, consists of tight junctions between specialized epithelial cells in the labyrinth spaces (i.e., the vestibular and cochlear spaces). The presence of the BLB limits delivery of active agents (e.g., antimicrobial agents) to the isolated microenvironment of the inner ear. Auris hair cells are bathed in endolymphatic or perilymphatic fluids and cochlear recycling of potassium ions is important for hair cell function. When the inner ear is infected, there is an influx of leukocytes and/or immunoglobins (e.g. in response to a microbial infection) into the endolymph and/or the perilymph and the delicate ionic composition of inner ear fluids is upset by the influx of leukocytes and/or immunoglobins. In certain instances, a change in the ionic composition of inner ear fluids results in hearing loss, loss of balance and/or ossification of auditory structures. In certain instances, even trace amounts of pyrogens and/or microbes can trigger infections and related physiological changes in the isolated microenvironment of the inner ear.

Due to the susceptibilty of the inner ear to infections, auris formulations require a level of sterility that has not been recognized hitherto in prior art. Provided herein are auris formulations that are manufactured with low bioburden or sterilized with stringent sterility requirements and are suitable for administration to the middle and/or inner ear. In some embodiments, the auris compatible compositions described herein are substantially free of pyrogens and/or microbes.

Compatibility with Inner Ear Environment

Described herein are otic formulations with an ionic balance that is compatible with the perilymph and/or the endolymph and does not cause any change in cochlear potential. In specific embodiments, osmolarity/osmolality of the present formulations is adjusted, for example, by the use of appropriate salt concentrations (e.g., concentration of sodium salts) or the use of tonicity agents which renders the formulations endolymph-compatible and/or perilymph-compatible (i.e. isotonic with the endolymph and/or perilymph). In some instances, the endolymph-compatible and/or perilymph-compatible formulations described herein cause minimal disturbance to the environment of the inner ear and cause minimum discomfort (e.g., vertigo) to a mammal (e.g., a human) upon administration. Further, the formulations comprise polymers that are biodegradable and/or dispersable, and/or otherwise non-toxic to the inner ear environment. In some embodiments, the formulations described herein are free of preservatives and cause minimal disturbance (e.g., change in pH or osmolarity, irritation) in auditory structures. In some embodiments, the formulations described herein comprise antioxidants that are non-irritating and/or non-toxic to otic structures.

Dosing Frequency

The current standard of care for auris formulations requires multiple administrations of drops or injections (e.g. intratympanic injections) over several days (e.g., up to two weeks), including schedules of receiving multiple injections per day. In some embodiments, auris formulations described herein are controlled release formulations, and are administered at reduced dosing frequency compared to the current standard of care. In certain instances, when an auris formulation is administered via intratympanic injection, a reduced frequency of administration alleviates discomfort caused by multiple intratympanic injections in individuals undergoing treatment for a middle and/or inner ear disease, disorder or condition. In certain instances, a reduced frequency of administration of intratympanic injections reduces the risk of permanent damage (e.g., perforation) to the ear drum. The formulations described herein provide a constant, sustained, extended, delayed or pulsatile rate of release of an active agent into the inner ear environment and thus avoid any variability in drug exposure in treatment of otic disorders. In some embodiments, the compositions or devices described herein avoid variability in contact with the round window (a major site of inner ear drug absorption). In some embodiments, the compositions or devices described herein avoid a short residence time in the middle ear.

Therapeutic Index

Auris formulations described herein are administered into the ear canal, or in the vestibule of the ear. Access to, for example, the vestibular and cochlear apparatus will occur through the auris media including the round window membrane, the oval window/stapes footplate, the annular ligament and through the otic capsule/temporal bone. Otic administration of the formulations described herein avoids toxicity associated with systemic administration (e.g., hepatotoxicity, cardiotoxicity, gastrointestinal side effects, renal toxicity) of the active agents. In some instances, localized administration in the ear allows an active agent to reach a target organ (e.g., inner ear) in the absence of systemic accumulation of the active agent. In some instances, local administration to the ear provides a higher therapeutic index for an active agent that would otherwise have dose-limiting systemic toxicity.

Prevention of Drainage into Eustachian Tube

In some instances, a disadvantage of liquid formulations is their propensity to drip into the eustachian tube and cause rapid clearance of the formulation from the inner ear. Provided herein, in certain embodiments, are auris formulations comprising polymers that gel at body temperature and remain in contact with the target auditory surfaces (e.g., the round window) for extended periods of time. In some embodiments, the formulations further comprise mucoadhesives that allow the formulations to adhere to otic mucosal surfaces. In some instances, the auris formulations described herein avoid attenuation of therapeutic benefit due to drainage or leakage of active agents via the eustachian tube.

Description of Certain Embodiments

Described herein are controlled release compositions and devices for treating otic disorders comprising a therapeutically-effective amount of an antimicrobial agent, a controlled release auris-acceptable excipient and an auris-acceptable vehicle. In one aspect, the controlled release auris-acceptable excipient is an auris-acceptable polymer, an auris-acceptable viscosity enhancing agent, an auris-acceptable gel, an auris-acceptable paint, an auris-acceptable microsphere, microcapsule or microparticle, an auris-acceptable in situ forming spongy material, an auris-acceptable hydrogel, an auris-acceptable liposome, an auris-acceptable nanocapsule, nanoparticle, or nanosphere, an auris-acceptable thermoreversible gel, an auris-acceptable foam, an auris-acceptable xerogel, or combinations thereof. In certain specific embodiments, the auris-acceptable viscosity enhancing agent is a carbomer, a cellulose, a cellulose ether, alginate, polyvinylpyrrolidone, a gum, a cellulosic polymer or combinations thereof. In yet another embodiment, the auris-acceptable viscosity enhancing agent is present in an amount sufficient to provide a viscosity of between about 1000 to about 1,000,000 centipoise. In still another aspect, the auris-acceptable viscosity enhancing agent is present in an amount sufficient to provide a viscosity of between about 50,000 to about 1,000,000 centipoise. In some embodiments, the antimicrobial agent formulations or compositions are optimal for osmolality or osmolarity of the target auris structure to ensure homeostasis is maintained.

In some embodiments, the compositions are formulated for pH, and a practical osmolality or osmolarity to ensure that homeostasis of the target auris structure is maintained. A perilymph-suitable osmolarity/osmolality is a practical/deliverable osmolarity/osmolality that maintains the homeostasis of the target auris structure during administration of the pharmaceutical formulations described herein.

For example, the osmolarity of the perilymph is between about 270-300 mOsm/L, and the compositions described herein are optionally formulated to provide a practical osmolarity of about 150 to about 1000 mOsm/L. In certain embodiments, the formulations described herein provide a practical and/or deliverable osmolarity within about 150 to about 500 mOsm/L at the target site of action (e.g., the inner ear and/or the perilymph and/or the endolymph). In certain embodiments, the formulations described herein provide a practical osmolarity within about 200 to about 400 mOsm/L at the target site of action (e.g., the inner ear and/or the perilymph and/or the endolymph). In certain embodiments, the formulations described herein provide a practical osmolarity within about 250 to about 320 mOsm/L at the target site of action (e.g., the inner ear and/or the perilymph and/or the endolymph). In certain embodiments, the formulations described herein provide a perilymph-suitable osmolarity within about 150 to about 500 mOsm/L, about 200 to about 400 mOsm/L or about 250 to about 320 mOsm/L at the target site of action (e.g., the inner ear and/or the perilymph and/or the endolymph). In certain embodiments, the formulations described herein provide a perilymph-suitable osmolality within about 150 to about 500 mOsm/kg, about 200 to about 400 mOsm/kg or about 250 to about 320 mOsm/kg at the target site of action (e.g., the inner ear and/or the perilymph and/or the endolymph). Similarly, the pH of the perilymph is about 7.2-7.4, and the pH of the present formulations is formulated (e.g., with the use of buffers) to provide a perilymph-suitable pH of about 5.5 to about 9.0, about 6.0 to about 8.0 or about 7.0 to about 7.6. In certain embodiments, the pH of the formulations is within about 6.0 to about 7.6. In certain instances, the pH of the endolymph is about 7.2-7.9, and the pH of the present formulations is formulated (e.g., with the use of buffers) to be within about 5.5 to about 9.0, within about 6.5 to about 8.0 or within about 7.0 to about 7.6.

In some aspects, the controlled-release auris-acceptable excipient is biodegradable. In some aspects the controlled release auris-acceptable excipient is bioeliminated (e.g., degraded and/or eliminated through urine, feces or other routes of elimination). In another aspect, the controlled release composition further comprises an auris-acceptable mucoadhesive, an auris-acceptable penetration enhancer or an auris-acceptable bioadhesive.

In one aspect, the controlled release antimicrobial agent composition is delivered using a drug delivery device, which is a needle and syringe, a pump, a microinjection device or combinations thereof. In some embodiments, the antimicrobial agent of the controlled release composition has limited or no systemic release, is toxic when administered systemically, has poor pK characteristics or combinations thereof. In some aspects, the antimicrobial agent is a small molecule.

Also disclosed herein are methods for the treatment of otic disorders comprising local administration of an antimicrobial agent controlled release formulation to the ear. Otic disorders treatable with the formulations disclosed herein include otitis externa, otitis media, Ramsay Hunt syndrome, otosyphilis, autoimmune inner ear disease (AIED), Meniere's disease, and vestibular neuronitis. In certain embodiments, a method for treating an otic disorder comprises administering any of the compositions disclosed herein at least once every 3, 4, 5, 6, 7, 8, 9, 10, 11, 12, 13, 14 or 15 days; or at least once a week, once every two weeks, once every three weeks, once every four weeks, once every five weeks, or once every six weeks; or once a month, once every two months, once every three months, once every four months, once every five months, once every six months, once every seven months, once every eight months, once every nine months, once every ten months, once every eleven months, or once every twelve months.

In particular embodiments, the controlled release formulations described herein provide a sustained dose of antimicrobial agent to the inner ear between subsequent doses of the controlled release formulation. That is, taking one example only, if new doses of the antimicrobial agent controlled release formulation are adminstered via intratympanic injection to the round window membrane every 10 days, then the controlled release formulation provides an effective dose of antimicrobial agent to the inner ear (e.g., across the round window membrane) during that 10-day period.

In one aspect, the composition is administered so that the composition is in contact with the crista fenestrae cochleae, the round window membrane or the tympanic cavity. In one aspect the composition is administered by intratympanic injection.

Provided herein is a pharmaceutical composition or device comprising an amount of an antimicrobial agent that is therapeutically effective for treating an otic disease or condition associated with a microbial infection, the pharmaceutical composition or device comprising substantially low degradation products of the antimicrobial agent, the pharmaceutical composition or device further comprising two or more characteristics selected from:

(i) between about 0.1% to about 10% by weight of the antimicrobial agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate antimicrobial agent;
(v) a gelation temperature between about 19° C. to about 42° C.;
(vi) less than about 50 colony forming units (cfu) of microbiological agents per gram of formulation;
(vii) less than about 5 endotoxin units (EU) per kg of body weight of a subject;
(viii) a mean dissolution time of about 30 hours for the antimicrobial agent; and
(ix) an apparent viscosity of about 100,000 cP to about 500,000 cP.

In some embodiments, the pharmaceutical composition comprises at least three of the aforementioned characteristics. In some embodiments, the pharmaceutical composition comprises at least four of the aforementioned characteristics. In some embodiments, the pharmaceutical composition comprises at least five of the aforementioned characteristics. In some embodiments, the pharmaceutical composition comprises at least six of the aforementioned characteristics. In some embodiments, the pharmaceutical composition comprises at least seven of the aforementioned characteristics. In some embodiments, the pharmaceutical composition comprises all of the aforementioned characteristics.

In some embodiments, a pharmaceutical composition or device described herein comprises:
(i) between about 0.1% to about 10% by weight of the antimicrobial agent, or pharmaceutically acceptable prodrug or salt thereof;
(ii) between about 14% to about 21% by weight of a polyoxyethylene-polyoxypropylene triblock copolymer of general formula E106 P70 E106; and
(iii) multiparticulate antimicrobial agent; and
(iv) an apparent viscosity of about 100,000 cP to about 500,000 cP.

In some embodiments, a pharmaceutical composition or device described herein comprises:
(i) between about 0.1% to about 10% by weight of the antimicrobial agent, or pharmaceutically acceptable prodrug or salt thereof;
(ii) between about 14% to about 21% by weight of a polyoxyethylene-polyoxypropylene triblock copolymer of general formula E106 P70 E106;
(iii) multiparticulate antimicrobial agent;
(iv) a gelation temperature between about 19° C. to about 42° C.; and
(v) a mean dissolution time of about 30 hours for the antimicrobial agent.

In some embodiments, a pharmaceutical composition or device described herein comprises:
(i) multiparticulate antimicrobial agent;
(ii) a gelation temperature between about 19° C. to about 42° C.; and
(iii) a mean dissolution time of about 30 hours for the antimicrobial agent; and
(iv) an apparent viscosity of about 100,000 cP to about 500,000 cP.

In some embodiments, a pharmaceutical composition or device described herein comprises:
(i) multiparticulate antimicrobial agent; and
(ii) a mean dissolution time of about 30 hours for the antimicrobial agent.

In some embodiments a pharmaceutical composition or device described above provides a practical osmolarity between about 150 and 500 mOsm/L. In some embodiments a pharmaceutical composition or device described above provides a practical osmolarity between about 200 and 400 mOsm/L. In some embodiments a pharmaceutical composition or device described above provides a practical osmolarity between about 250 and 320 mOsm/L.

In some embodiments, the antimicrobial agent is released from the pharmaceutical composition or device described above for a period of at least 3 days. In some embodiments, the antimicrobial agent is released from the pharmaceutical composition or device described above for a period of at least 5 days. In some embodiments, the antimicrobial agent is released from the pharmaceutical composition or device described above for a period of at least 10 days. In some embodiments, the antimicrobial agent is released from the pharmaceutical composition or device described above for a period of at least 14 days. In some embodiments, the antimicrobial agent is released from the pharmaceutical composition or device described above for a period of at least one month.

In some embodiments, a pharmaceutical composition or device described above comprises antimicrobial agent as a neutral compound, a free acid, a free base, a salt or a prodrug. In some embodiments, a pharmaceutical composition or device described above comprises antimicrobial agent as a neutral compound, a free acid, a free base, a salt or a prodrug, or a combination thereof. In some embodiments of the pharmaceutical compositions or devices described herein, the antimicrobial agent is administered in the form of a ester prodrug or a phosphate prodrug. In some embodiments pharmaceutical compositions or devices described herein comprise one or more antimicrobial agent, or pharmaceutically acceptable salt thereof, prodrug or combination thereof as an immediate release agent.

In some embodiments, a pharmaceutical composition or device described above is an auris-acceptable thermoreversible gel. In some embodiments of the pharmaceutical composition or device, the polyoxyethylene-polyoxypropylene triblock copolymer is bioeliminated.

In some embodiments the pharmaceutical composition or device further comprises a penetration enhancer. In some embodiments, the pharmaceutical composition or device further comprises a dye.

In some embodiments, the pharmaceutical composition or device further comprises the antimicrobial agent, or pharmaceutically acceptable salt thereof, prodrug or combination thereof as an immediate release agent.

In some embodiments the pharmaceutical composition or device comprises the antimicrobial agent as multiparticulates. In some embodiments of the pharmaceutical composition or device, the antimicrobial agent is essentially in the form of micronized particles. In some embodiments of the pharmaceutical composition or device, the antimicrobial agent is in the form of micronized antimicrobial agent powder.

In some embodiments, a pharmaceutical composition or device described above comprises about 10% of a polyoxyethylene-polyoxypropylene triblock copolymer of general formula E106 P70 E106 by weight of the composition. In some embodiments, a pharmaceutical composition or device described above comprises about 15% of a polyoxyethylene-polyoxypropylene triblock copolymer of general formula E106 P70 E106 by weight of the composition. In some embodiments, a pharmaceutical composition or device described above comprises about 20% of a polyoxyethylene-polyoxypropylene triblock copolymer of general formula E106 P70 E106 by weight of the composition. In some embodiments, a pharmaceutical composition or device described above comprises about 25% of a polyoxyethylene-polyoxypropylene triblock copolymer of general formula E106 P70 E106 by weight of the composition.

In some embodiments, a pharmaceutical composition or device described above comprises about 0.01% of an antimicrobial agent, or pharmaceutically acceptable prodrug or salt thereof, by weight of the composition. In some embodiments, a pharmaceutical composition or device described above comprises about 0.05% of an antimicrobial agent, or pharmaceutically acceptable prodrug or salt thereof, by weight of the composition. In some embodiments, a pharmaceutical composition or device described above comprises about 0.1% of an antimicrobial agent, or pharmaceutically acceptable prodrug or salt thereof, by weight of the composition. In some embodiments, a pharmaceutical composition or device described above comprises about 1% of an antimicrobial agent, or pharmaceutically acceptable prodrug or salt thereof, by weight of the composition. In some embodiments, a pharmaceutical composition or device described above comprises about 2.5% of an antimicrobial agent, or pharmaceutically acceptable prodrug or salt thereof, by weight of the composition. In some embodiments, a pharmaceutical composition or device described above comprises about 5% of an antimicrobial agent, or pharmaceutically acceptable prodrug or salt thereof, by weight of the composition. In some embodiments, a pharmaceutical composition or device described above comprises about 10% of an antimicrobial agent, or pharmaceutically acceptable prodrug or salt thereof, by weight of the composition. In some embodiments, a pharmaceutical composition or device described above comprises about 20% of an antimicrobial agent, or pharmaceutically acceptable prodrug or salt thereof, by weight of the composition. In some embodiments, a pharmaceutical composition or device described above comprises about 30% of an antimicrobial agent, or pharmaceutically acceptable prodrug or salt thereof, by weight of the composition. In some embodiments, a pharmaceutical composition or device described above comprises about 40% of an antimicrobial agent, or pharmaceutically acceptable prodrug or salt thereof, by weight of the composition. In some embodiments, a pharmaceutical composition or device described above comprises about 50% of an antimicrobial agent, or pharmaceutically acceptable prodrug or salt thereof, by weight of the composition.

In some embodiments, a pharmaceutical composition or device described above has a pH between about 5.5 to about 8.0. In some embodiments, a pharmaceutical composition or device described above has a pH between about 6.0 to about 8.0. In some embodiments, a pharmaceutical composition or device described above has a pH between about 6.0 to about 7.6. In some embodiments, a pharmaceutical composition or device described above has a pH between about 7.0 to about 7.6.

In some embodiments, a pharmaceutical composition or device described above contains less than 100 colony forming units (cfu) of microbiological agents per gram of formulation. In some embodiments, a pharmaceutical composition or device described above contains less than 50 colony forming units (cfu) of microbiological agents per gram of formulation. In some embodiments, a pharmaceutical composition or device described above contains less than 10 colony forming units (cfu) of microbiological agents per gram of formulation.

In some embodiments, a pharmaceutical composition or device described above contains less than 5 endotoxin units (EU) per kg of body weight of a subject. In some embodiments, a pharmaceutical composition or device described above contains less than 4 endotoxin units (EU) per kg of body weight of a subject.

In some embodiments a pharmaceutical composition or device described above provides a gelation temperature between about between about 19° C. to about 42° C. In some embodiments a pharmaceutical composition or device described above provides a gelation temperature between about between about 19° C. to about 37° C. In some embodiments a pharmaceutical composition or device described above provides a gelation temperature between about between about 19° C. to about 30° C.

In some embodiments, a pharmaceutical composition or device described above further comprises an anti-inflammatory agent. In some embodiments, a pharmaceutical composition or device described above further comprises an anti-inflammatory agent that is essentially in the form of micronized particles.

In some embodiments, the pharmaceutical composition or device is an auris-acceptable thermoreversible gel. In some embodiments, the polyoxyethylene-polyoxypropylene triblock copolymer is biodegradable and/or bioeliminated (e.g., the copolymer is eliminated from the body by a biodegradation process, e.g., elimination in the urine, the feces or the like). In some embodiments, a pharmaceutical composition or device described herein further comprises a mucoadhesive. In some embodiments, a pharmaceutical composition or device described herein further comprises a penetration enhancer. In some embodiments, a pharmaceutical composition or device described herein further comprises a thickening agent. In some embodiments, a pharmaceutical composition or device described herein further comprises a dye.

In some embodiments, a pharmaceutical composition or device described herein further comprises a drug delivery device selected from a needle and syringe, a pump, a microinjection device, a wick, an in situ forming spongy material or combinations thereof.

In some embodiments, a pharmaceutical composition or device described herein is a pharmaceutical composition or device wherein the antimicrobial agent, or pharmaceutically acceptable salt thereof, has limited or no systemic release, systemic toxicity, poor PK characteristics, or combinations thereof.

In some embodiments, pharmaceutical compositions or devices described herein are pharmaceutical compositions or devices wherein the pH of the pharmaceutical composition or device is between about 6.0 to about 7.6.

In some embodiments of the pharmaceutical compositions or devices described herein, the ratio of a polyoxyethylene-polyoxypropylene triblock copolymer of general formula E106 P70 E106 to a thickening agent is from about 40:1 to about 5:1. In some embodiments, the thickening agent is carboxymethyl cellulose, hydroxypropyl cellulose or hydroxypropyl methylcellulose.

In some embodiments, the otic disease or condition is otitis externa, otitis media, Ramsay Hunt syndrome, otosyphilis, AIED, Meniere's disease, or vestibular neuronitis.

Also provided herein is a method of alleviating infection or inflammation associated with an otic intervention comprising administering to an individual in need thereof an intratympanic composition or device comprising a therapeutically effective amount of an antimicrobial agent, the composition or device comprising substantially low degradation products of the antimicrobial agent, the composition or device further comprising two or more characteristics selected from:
(i) between about 0.1% to about 10% by weight of the antimicrobial agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate antimicrobial agent;
(v) a gelation temperature between about 19° C. to about 42° C.;
(vi) less than about 50 colony forming units (cfu) of microbiological agents per gram of formulation;
(vii) less than about 5 endotoxin units (EU) per kg of body weight of a subject;
(viii) a mean dissolution time of about 30 hours; and
(ix) an apparent viscosity of about 100,000 cP to about 500,000 cP.

In some embodiments, the pharmaceutical composition comprises at least three of the aforementioned characteristics. In some embodiments, the pharmaceutical composition comprises at least four of the aforementioned characteristics. In some embodiments, the pharmaceutical composition comprises at least five of the aforementioned characteristics. In some embodiments, the pharmaceutical composition comprises at least six of the aforementioned characteristics. In some embodiments, the pharmaceutical composition comprises at least seven of the aforementioned characteristics. In some embodiments, the pharmaceutical composition comprises all of the aforementioned characteristics.

Also provided herein is a method of treating an otic disease or condition associated with a microbial infection comprising administering to an individual in need thereof an intratympanic composition or device comprising a therapeutically effective amount of an antimicrobial agent, the composition or device comprising substantially low degradation products of the antimicrobial agent, the composition or device further comprising two or more characteristics selected from:
(i) between about 0.1% to about 10% by weight of the antimicrobial agent, or pharmaceutically acceptable prodrug or salt thereof;
(ii) between about 14% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate antimicrobial agent;
(v) a gelation temperature between about 19° C. to about 42° C.;
(vi) less than about 50 colony forming units (cfu) of microbiological agents per gram of formulation;
(vii) less than about 5 endotoxin units (EU) per kg of body weight of a subject;
(viii) a mean dissolution time of about 30 hours for the antimicrobial agent; and
(ix) an apparent viscosity of about 100,000 cP to about 500,000 cP.

In some embodiments, the pharmaceutical composition comprises at least three of the aforementioned characteristics. In some embodiments, the pharmaceutical composition comprises at least four of the aforementioned characteristics. In some embodiments, the pharmaceutical composition comprises at least five of the aforementioned characteristics. In some embodiments, the pharmaceutical composition comprises at least six of the aforementioned characteristics. In some embodiments, the pharmaceutical composition comprises at least seven of the aforementioned characteristics. In some embodiments, the pharmaceutical composition comprises all of the aforementioned characteristics.

In some embodiments of the methods described above, the antimicrobial agent is released from the composition or device for a period of at least 3 days. In some embodiments of the methods described above, the antimicrobial agent is released from the composition or device for a period of at least 5 days. In some embodiments of the methods described above, the antimicrobial agent is released from the composition or device for a period of at least 10 days. In some embodiments of the method described above, the antimicrobial agent is essentially in the form of micronized particles.

In some embodiments of the methods, a pharmaceutical composition or device described above further comprises an anti-inflammatory agent. In some embodiments of the methods, a pharmaceutical composition or device described above further comprises an anti-inflammatory agent that is essentially in the form of micronized particles. In some embodiments of the methods, a pharmaceutical composition or device described above is administered in combination with an otic intervention. In some embodiments of the methods, a pharmaceutical composition or device described above is administered before an otic intervention. In some embodiments of the methods, a pharmaceutical composition or device described above is administered during an otic intervention. In some embodiments of the methods, a pharmaceutical composition or device described above is administered after an otic intervention.

In some embodiments, the otic and/or vestibular disorder is otitis externa, otitis media, Ramsay Hunt syndrome, otosyphilis, AIED, Meniere's disease, or vestibular neuronitis. In some embodiments, administration of any antimicrobial composition or device described above reduces the risk of development of antibiotic resistance.

DETAILED DESCRIPTION OF THE INVENTION

Figure 1:
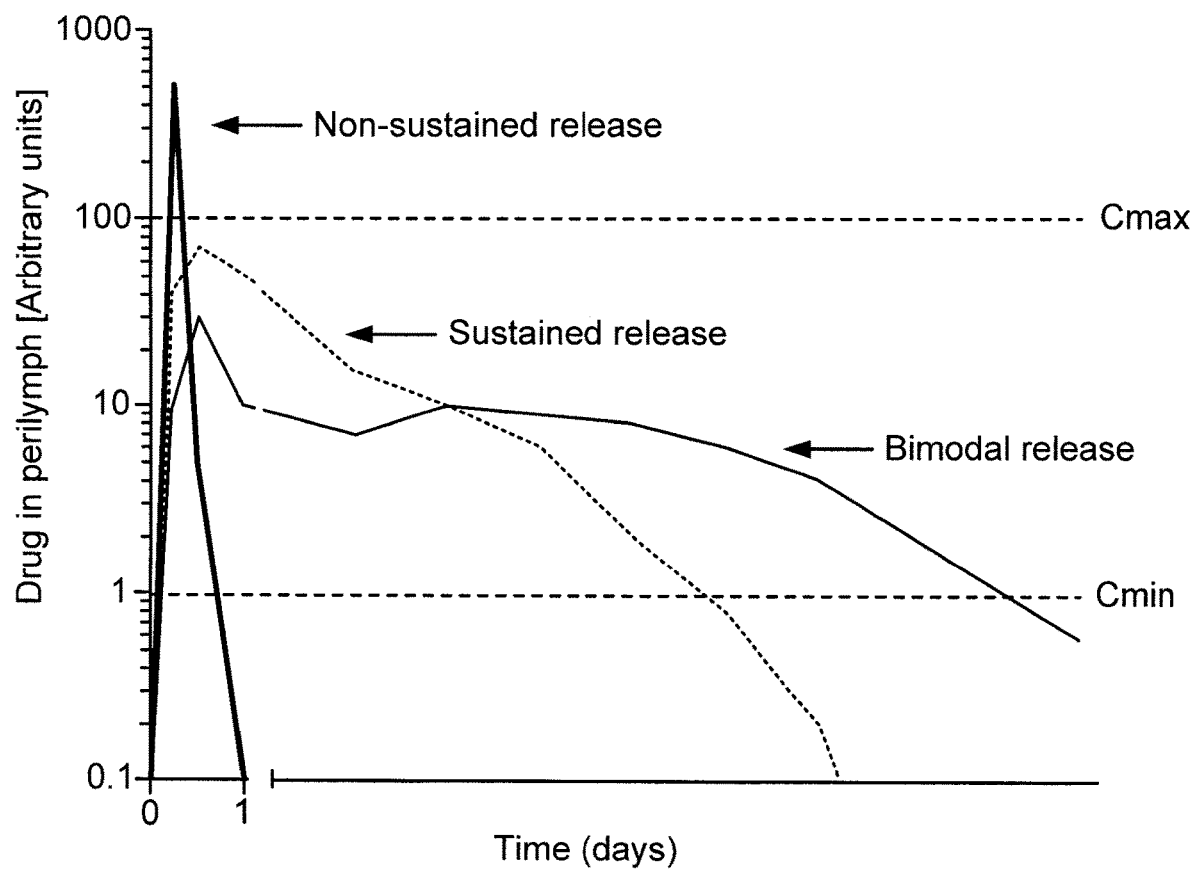
FIG. 1. illustrates a comparison of non-sustained release and sustained release formulations.
Figure 2:
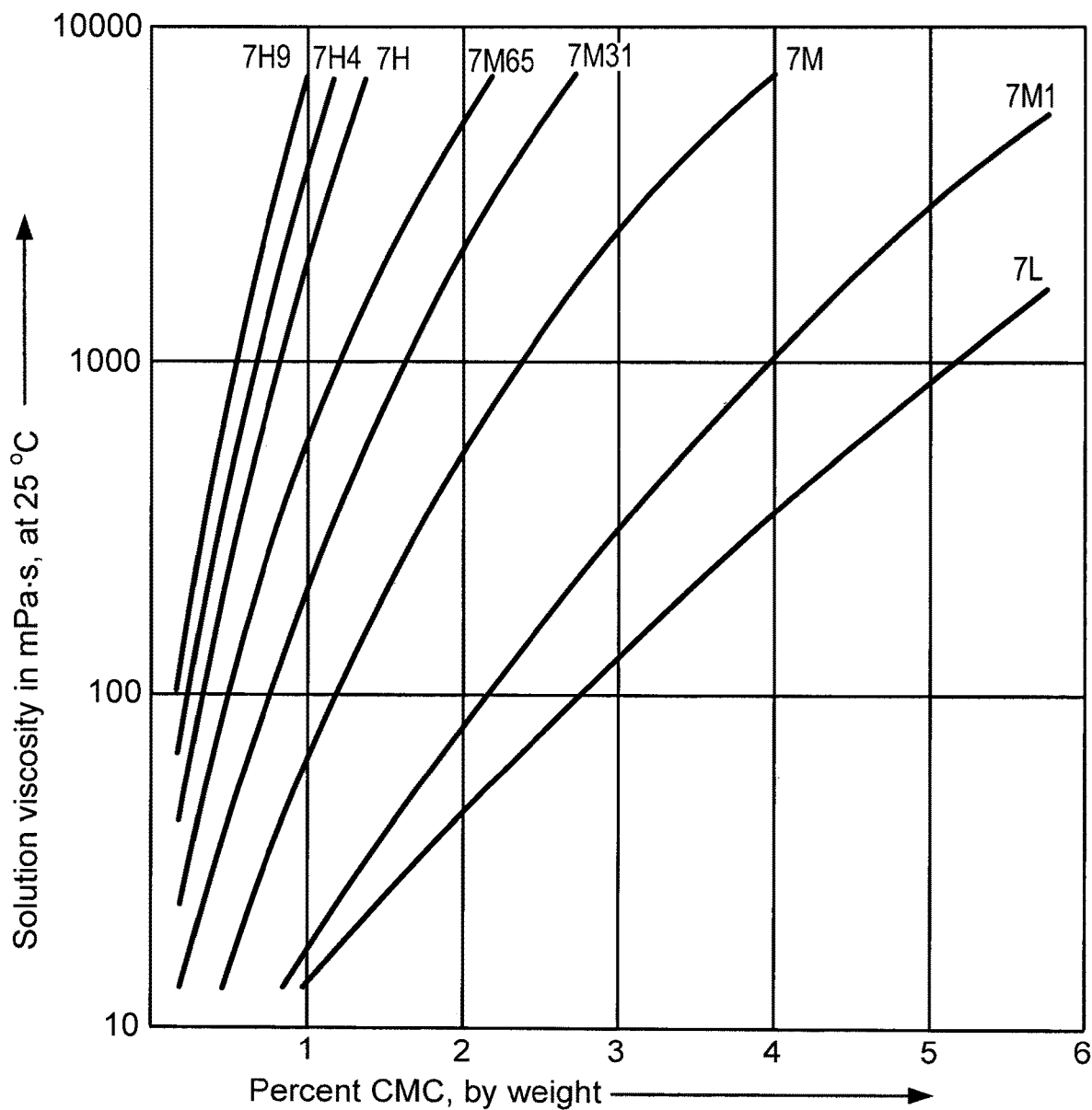
FIG. 2 illustrates the effect of concentration on the viscosity of aqueous solutions of Blanose refined CMC.
Figure 3:
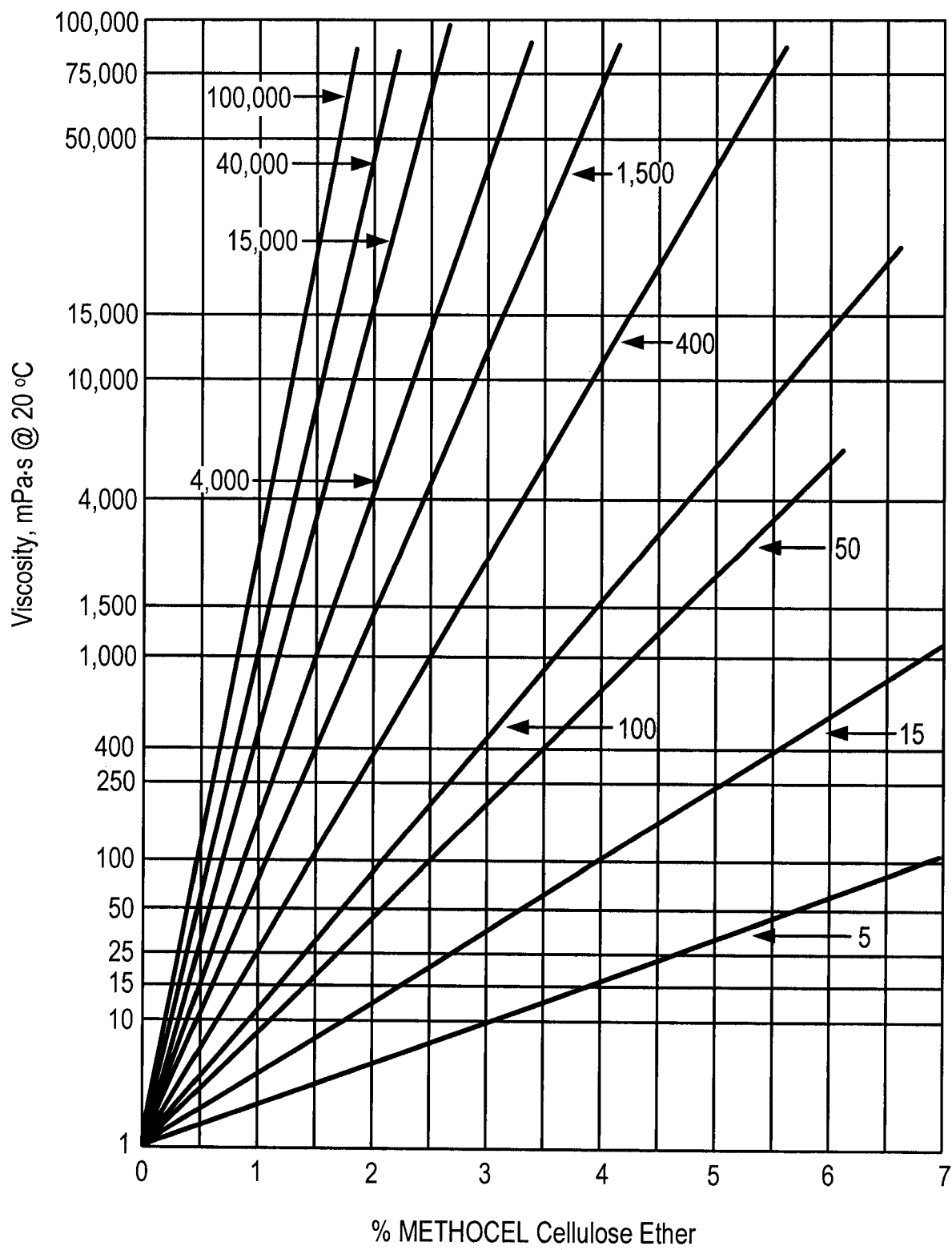
FIG. 3 illustrates the effect of concentration on the viscosity of aqueous solutions of Methocel.

Provided herein are controlled release antimicrobial agent compositions and formulations for the treatment of otic disorders, including otitis externa, otitis media, Ramsay Hunt syndrome, otosyphilis, AIED, Meniere's disease, and vestibular neuronitis. In some embodiments, the antimicrobial agent is an antibacterial agent, an antifungal agent, an antiviral agent, an antiprotozoal agent, and/or an antiparasitic agent. In certain embodiments, the antimicrobial agent is a protein, an antibody, DNA, a carbohydrate, an inorganic compound, an organic compound, or combinations thereof. In certain particular embodiments, the antimicrobial agent is a small organic molecule. Compositions comprising combinations of therapeutic agents useful for the treatment of otic disorders, including combinations of different antimicrobial agents, as well as combinations of antimicrobial agents with other therapeutic agents, are also encompassed in certain embodiments disclosed herein.

Otitis externa (OE), also referred to as swimmer's ear, is an inflammation of the external ear and/or ear canal. OE is primarily caused by bacteria (e.g., *Pseudomonas aeruginosa* and *Staphylococcus aureus*) or fungi (e.g., *Candida albicans* and *Aspergillus*) in the outer ear, which establish infection following damage to the skin of the ear canal. Symptoms of OE include otalgia, swelling, and otorrhea. If the condition progresses significantly, OE may cause temporary conductive hearing loss as a result of the swelling and discharge. Treatment of OE involves eliminating the aggravating pathogen from the ear canal and reducing inflammation, which is usually accomplished by administering combinations of antimicrobial agents, e.g., antibacterial and antifungal agents, with anti-inflammatory agents, e.g., steroids.

Otitis media (OM) is an inflammation of the middle ear. Bacterial infection accounts for a large percentage of OM cases, with more than 40% of cases attributed to *Streptococcus pneumoniae* infection. However, viruses, as well as other microbes, may account for OM conditions. Because OM can be caused by a virus, bacteria or both, various antimicrobial agents are used to eliminate the underlying pathogen.

Syphilis is a venereal disease, caused by the spirochete *Treponema pallidum*, which may result in otic disorders, particularly cochleovestibular disorders, due to membranous labyrinthitis, and secondarily meningitis. Both acquired and congenital syphilis can cause otic disorders. Symptoms of cochleovestibular disorders resulting from syphilis are often similar to those of other otic disorders, such as AIED and Meniere's disease, and include tinnitus, deafness, vertigo, malaise, sore throat, headaches, and skin rashes.

Treatment of otosyphilis (syphilis presenting otic symptoms) typically includes a combination of steroids and antibacterial agents. Such treatments may be effective in eradicating the spirochete organism while reducing inflammation. However, Treponemas may remain in the cochlear and vestibular endolymph even after eradication from other sites in the body. Accordingly, long term treatment with penicillins may be required to achieve complete eradication of the spirochete organism from the endolymph fluid.

Systemic antimicrobial administration for the treatment of otic disorders, e.g., OE, OM and otosyphilis, may create a potential inequality in drug concentration with higher circulating levels in the serum, and lower levels in the target auris interna organ structures. As a result, fairly large amounts of drug are required to overcome this inequality in order to deliver sufficient, therapeutically effective quantities to the inner ear. Further, bioavailability is often decreased due to metabolism of the drug by the liver. In addition, systemic drug administration may increase the likelihood of systemic toxicities and adverse side effects as a result of the high serum amounts required to effectuate sufficient local delivery to the target site. Systemic toxicities may also occur as a result of liver breakdown and processing of the therapeutic agents, forming toxic metabolites that effectively erase any benefit attained from the administered therapeutic.

To overcome the toxic and attendant undesired side effects of systemic delivery of antimicrobial agents (which are generally understood to be toxic to cells), disclosed herein are methods and compositions for local delivery of antimicrobial agents to auris media and/or auris interna structures. Access to, for example, the vestibular and cochlear apparatus will occur through the auris media or auris interna, including the round window membrane, the oval window/stapes footplate, the annular ligament and through the otic capsule/temporal bone. In further or alternative embodiments, the auris controlled-release formulations are capable of being administered on or near the round window membrane via intratympanic injection. In other embodiments, the auris controlled release formulations are administered on or near the round window or the crista fenestrae cochleae through entry via a post-auricular incision and surgical manipulation into or near the round window or the crista fenestrae cochleae area. Alternatively, the auris controlled release formulation is applied via syringe and needle, wherein the needle is inserted through the tympanic membrane and guided to the area of the round window or crista fenestrae cochleae.

In addition, localized treatment of the auris interna also affords the use of previously undesired therapeutic agents, including agents with poor pK profiles, poor uptake, low systemic release, and/or toxicity issues.

Because of the localized targeting of the antimicrobial agent formulations and compositions, as well as the biological blood barrier present in the auris interna, the risk of adverse effects will be reduced as a result of treatment with previously characterized toxic or ineffective antimicrobial agent. Localized administration of antimirobial agent compositions reduces the risk of development of resistance to antibiotics compared to the risk for development of antibiotic resistance when an antibiotic is administered systemically. The compositions described herein are effective for recurring otic diseases or conditions including, for example, recurring ear infections in children without the need for changing treatment regimens (e.g., in response to development of antibiotic resistance). Accordingly, also contemplated within the scope of the embodiments herein is the use of antimicrobial agents in the treatment of otic diseases or conditions including otitis externa, otitis media, Ramsay Hunt syndrome, otosyphilis, AIED, Meniere's disease, and vestibular neuronitis, including therapeutic agents that have been previously rejected by practitioners because of adverse effects or ineffectiveness of the antimicrobial agent(s).

Also included within the embodiments disclosed herein is the use of additional auris media and/or auris interna-acceptable agents in combination with the antimicrobial agent formulations and compositions disclosed herein. When used, such agents assist in the treatment of hearing or equilibrium loss or dysfunction resulting from an autoimmune disorder, including vertigo, tinnitus, hearing loss, balance disorders, infections, inflammatory response or combinations thereof. Accordingly, agents that ameliorate or reduce the effects of vertigo, tinnitus, hearing loss, balance disorders, infections, inflammatory response or combinations thereof are also contemplated to be used in combination with the antimicrobial agent(s) described herein.

In some embodiments, the composition further comprises an antimicrobial agent as an immediate release agent wherein the immediate release antimicrobial agent is the same agent as the controlled-release agent, a different antimicrobial agent, an additional therapeutic agent, or a combination thereof. In some embodiments, the composition further comprises an additional therapeutic agent, including an additional antimicrobial agent, an anti-inflammatory agent, a corticosteroid, a cytotoxic agent, an anti-TNF agent, a collagen, a gamma-globulin, an interferon, a platelet activator factor antagonist, a nitric oxide synthase inhibitor, or combinations thereof. In another aspect, the additional therapeutic agent is an immediate release or a controlled release agent.

In some embodiments, the additional therapeutic agent is an immediate release agent. In some embodiments, the additional therapeutic agent is a controlled release agent.

Accordingly, provided herein are controlled release antimicrobial agent formulations and compositions to locally treat auris media and/or auris interna structures, thereby avoiding side effects as a result of systemic administration of the antimicrobial agents. The locally applied antimicrobial agent formulations and compositions are compatible with auris media and/or auris interna structures, and are administered either directly to the desired auris media and/or auris interna structure, e.g. the cochlear region or the tympanic cavity, or administered to a structure in direct communication with areas of the auris interna, including but not limited to the round window membrane, the crista fenestrae cochleae or the oval window membrane. By specifically targeting the auris media or auris interna structures, adverse side effects as a result of systemic treatment are avoided. Moreover, by providing a controlled release antimicrobial agent formulation or composition to treat otic disorders, a constant and/or extended source of antimicrobial agent is provided to the individual or patient suffering from an otic disorder, reducing or eliminating the variability of treatment.

Intratympanic injection of therapeutic agents is the technique of injecting a therapeutic agent behind the tympanic membrane into the auris media and/or auris interna. Despite early success with this technique (Schuknecht, Laryngoscope (1956) 66, 859-870) some challenges do remain. For example, access to the round window membrane, the site of drug absorption into the auris interna, can be challenging.

However, intra-tympanic injections create several unrecognized problems not addressed by currently available treatment regimens, such as changing the osmolarity and pH of the perilymph and endolymph, and introducing pathogens and endotoxins that directly or indirectly damage inner ear structures. One of the reasons the art may not have recognized these problems is that there are no approved intratympanic compositions: the inner ear provides sui generis formulation challenges. Thus, compositions developed for other parts of the body have little to no relevance for an intra-tympanic composition.

There is no guidance in the prior art regarding requirements (e.g., level of sterility, pH, osmolarity) for otic formulations that are suitable for administration to humans. There is wide anatomical disparity between the ears of animals across species. A consequence of the inter-species differences in auditory structures is that animal models of inner ear disease are often unreliable as a tool for testing therapeutics that are being developed for clinical approval.

Provided herein are otic formulations that meet stringent criteria for pH, osmolarity, ionic balance, sterility, endotoxin and/or pyrogen levels. The auris compositions described herein are compatible with the microenvironment of the inner ear (e.g., the perilymph) and are suitable for administration to humans. In some embodiments, the formulations described herein comprise dyes and aid visualization of the administered compositions obviating the need for invasive procedures (e.g., removal of perilymph) during preclinical and/or clinical development of intratympanic therapeutics.

Provided herein are controlled release antimicrobial agent formulations and compositions to locally treat targeted auris structures, thereby avoiding side effects as a result of systemic administration of the antimicrobial agent formulations and compositions. The locally applied antimicrobial agent formulations and compositions and devices are compatible with the targeted auris structures, and administered either directly to the desired targeted auris structure, e.g. the cochlear region, the tympanic cavity or the external ear, or administered to a structure in direct communication with areas of the auris interna, including but not limited to the round window membrane, the crista fenestrae cochleae or the oval window membrane. By specifically targeting an auris structure, adverse side effects as a result of systemic treatment are avoided. Moreover, clinical studies have shown the benefit of having long term exposure of drug to the perilymph of the cochlea, for example with improved clinical efficacy of sudden hearing loss when the therapeutic agent is given on multiple occasions. Thus, by providing a controlled release antimicrobial agent formulation or composition to treat otic disorders, a constant, and/or extended source of antimicrobial agent is provided to the individual or patient suffering from an otic disorder, reducing or eliminating variabilities in treatment. Accordingly, one embodiment disclosed herein is to provide a composition that enables at least one antimicrobial agent to be released in therapeutically effective doses either at variable or constant rates such as to ensure a continuous release of the at least one agent. In some embodiments, the antimicrobial agents disclosed herein are administered as an immediate release formulation or composition. In other embodiments, the antimicrobial agents are administered as a sustained release formulation, released either continuously, variably or in a pulsatile manner, or variants thereof. In still other embodiments, antimicrobial agent formulation is administered as both an immediate release and sustained release formulation, released either continuously, variably or in a pulsatile manner, or variants thereof. The release is optionally dependent on environmental or physiological conditions, for example, the external ionic environment (see, e.g. Oros® release system, Johnson & Johnson).

In addition, the auris-acceptable controlled-release antimicrobial agent formulations and treatments described herein are provided to the target ear region of the individual in need, including the inner ear, and the individual in need is additionally administered an oral dose of antimicrobial agent. In some embodiments, the oral dose of antimicrobial agent is administered prior to administration of the auris-acceptable controlled-release antimicrobial agent formulation, and then the oral dose is tapered off over the period of time that the auris-acceptable controlled-release antimicrobial agent formulation is provided. Alternatively, the oral dose of antimicrobial agent is administered during administration of the auris-acceptable controlled-release antimicrobial agent formulation, and then the oral dose is tapered off over the period of time that the auris-acceptable controlled-release antimicrobial agent formulation is provided. Alternatively, the oral dose of antimicrobial agent is administered after administration of the auris-acceptable controlled-release antimicrobial agent formulation has been initiated, and then the oral dose is tapered off over the period of time that the auris-acceptable controlled-release antimicrobial agent formulation is provided.

In addition, the antimicrobial agent pharmaceutical compositions or formulations or devices included herein also include carriers, adjuvants, such as preserving, stabilizing, wetting or emulsifying agents, solution promoters, salts for regulating the osmotic pressure, and/or buffers. Such carriers, adjuvants, and other excipients will be compatible with the environment in the targeted auris structure(s). Accordingly, specifically contemplated for the compositions and devices described herein are carriers, adjuvants and excipients that lack ototoxicity or are minimally ototoxic in order to allow effective treatment of the otic disorders contemplated herein with minimal side effects in the targeted regions or areas.

Intratympanic injection of compositions or devices creates several additional problems that must also be addressed before the composition or device can be administered. For example, there are many excipients that are ototoxic. While these excipients can be used when formulating an active agent for delivery by another method (e.g., topical), their use should be limited, reduced or eliminated when formulating a delivery device to be administered to the ear due to their ototoxic effects.

By way of non-limiting example, the use of the following commonly used solvents should be limited, reduced or eliminated when formulating agents for administration to the ear: alcohols, propylene glycol, and cyclohexane. Thus, in some embodiments, a device disclosed herein is free or substantially free of alcohols, propylene glycol, and cyclohexane. In some embodiments, a device disclosed herein comprises less than about 50 ppm of each of alcohols, propylene glycol, and cyclohexane. In some embodiments, a device disclosed herein comprises less than about 25 ppm of each of alcohols, propylene glycol, and cyclohexane. In some embodiments, a device disclosed herein comprises less than about 20 ppm of each of alcohols, propylene glycol, and cyclohexane. In some embodiments, a device disclosed herein comprises less than about 10 ppm of each of alcohols, propylene glycol, and cyclohexane. In some embodiments, a device disclosed herein comprises less than about 5 ppm of each of alcohols, propylene glycol, and cyclohexane. In some embodiments, a device disclosed herein comprises less than about 1 ppm of each of alcohols, propylene glycol, and cyclohexane.

Further, by way of non-limiting example, the use of the following commonly utilized preservatives should be limited, reduced or eliminated when formulating agents for administration to the ear: Benzethonium chloride, Benzalkonium chloride, and Thiomersal. Thus, in some embodiments, a device disclosed herein is free or substantially free of benzethonium chloride, benzalkonium chloride, and thiomersal. In some embodiments, a device disclosed herein comprises less than about 50 ppm of each of benzethonium chloride, benzalkonium chloride, and thiomersal. In some embodiments, a device disclosed herein comprises less than about 25 ppm of each of benzethonium chloride, benzalkonium chloride, and thiomersal. In some embodiments, a device disclosed herein comprises less than about 20 ppm of each of benzethonium chloride, benzalkonium chloride, and thiomersal. In some embodiments, a device disclosed herein comprises less than about 10 ppm of each of benzethonium chloride, benzalkonium chloride, and thiomersal. In some embodiments, a device disclosed herein comprises less than about 5 ppm of each of benzethonium chloride, benzalkonium chloride, and thiomersal. In some embodiments, a device disclosed herein comprises less than about 1 ppm of each of benzethonium chloride, benzalkonium chloride, and thiomersal.

Certain antiseptics used to disinfect components of therapeutic preparations (or the devices utilized to administer the preparations) should be limited, reduced, or eliminated in otic preparations. For example, acetic acid, iodine, and merbromin are all known to be ototoxic. Additionally, chlorhexidene, a commonly used antiseptic, should be limited, reduced or eliminated to disinfect any component of an otic preparation (including devices used to administer the preparation) as it is highly ototoxic in minute concentrations (e.g., 0.05%). Thus, in some embodiments, a device disclosed herein is free or substantially free of acetic acid, iodine, merbromin, and chlorhexidene. In some embodiments, a device disclosed herein comprises less than about 50 ppm of each of acetic acid, iodine, merbromin, and chlorhexidene. In some embodiments, a device disclosed herein comprises less than about 25 ppm of each of acetic acid, iodine, merbromin, and chlorhexidene. In some embodiments, a device disclosed herein comprises less than about 20 ppm of each of acetic acid, iodine, merbromin, and chlorhexidene. In some embodiments, a device disclosed herein comprises less than about 10 ppm of each of acetic acid, iodine, merbromin, and chlorhexidene. In some embodiments, a device disclosed herein comprises less than about 5 ppm of each of acetic acid, iodine, merbromin, and chlorhexidene. In some embodiments, a device disclosed herein comprises less than about 1 ppm of each of acetic acid, iodine, merbromin, and chlorhexidene.

Further, otic preparations require particularly low concentrations of several potentially-common contaminants that are known to be ototoxic. Other dosage forms, while seeking to limit the contamination attributable to these compounds, do not require the stringent precautions that otic preparations require. For example, the following contaminants should be absent or nearly absent from otic preparations: arsenic, lead, mercury, and tin. Thus, in some embodiments, a device disclosed herein is free or substantially free of arsenic, lead, mercury, and tin. In some embodiments, a device disclosed herein comprises less than about 50 ppm of each of arsenic, lead, mercury, and tin. In some embodiments, a device disclosed herein comprises less than about 25 ppm of each of arsenic, lead, mercury, and tin. In some embodiments, a device disclosed herein comprises less than about 20 ppm of each of arsenic, lead, mercury, and tin. In some embodiments, a device disclosed herein comprises less than about 10 ppm of each of arsenic, lead, mercury, and tin. In some embodiments, a device disclosed herein comprises less than about 5 ppm of each of arsenic, lead, mercury, and tin. In some embodiments, a device disclosed herein comprises less than about 1 ppm of each of arsenic, lead, mercury, and tin.

To prevent ototoxicity, antimicrobial agent pharmaceutical compositions or formulations or devices disclosed herein are optionally targeted to distinct regions of the targeted auris structures, including but not limited to the tympanic cavity, vestibular bony and membranous labyrinths, cochlear bony and membranous labyrinths and other anatomical or physiological structures located within the auris interna.

Certain Definitions

The term "auris-acceptable" with respect to a formulation, composition or ingredient, as used herein, includes having no persistent detrimental effect on the auris interna (or inner ear) of the subject being treated. By "auris-pharmaceutically acceptable," as used herein, refers to a material, such as a carrier or diluent, which does not abrogate the biological activity or properties of the compound in reference to the auris interna (or inner ear), and is relatively or is reduced in toxicity to the auris interna (or inner ear), i.e., the material is administered to an individual without causing undesirable biological effects or interacting in a deleterious manner with any of the components of the composition in which it is contained.

As used herein, amelioration or lessening of the symptoms of a particular otic disease, disorder or condition by administration of a particular compound or pharmaceutical composition refers to any decrease of severity, delay in onset, slowing of progression, or shortening of duration, whether permanent or temporary, lasting or transient that is attributed to or associated with administration of the compound or composition.

"Antioxidants" are auris-pharmaceutically acceptable antioxidants, and include, for example, butylated hydroxytoluene (BHT), sodium ascorbate, ascorbic acid, sodium metabisulfite and tocopherol. In certain embodiments, antioxidants enhance chemical stability where required. Antioxidants are also used to counteract the ototoxic effects of certain therapeutic agents, including agents that are used in combination with the antimicrobial agents disclosed herein.

"Auris interna" refers to the inner ear, including the cochlea and the vestibular labyrinth, and the round window that connects the cochlea with the middle ear.

"Auris-interna bioavailability" refers to the percentage of the administered dose of compounds disclosed herein that becomes available in the inner ear of the animal or human being studied.

"Auris media" refers to the middle ear, including the tympanic cavity, auditory ossicles and oval window, which connects the middle ear with the inner ear.

"Balance disorder" refers to a disorder, illness, or condition which causes a subject to feel unsteady, or to have a sensation of movement. Included in this definition are dizziness, vertigo, disequilibrium, and pre-syncope. Diseases which are classified as balance disorders include, but are not limited to, Ramsay Hunt's Syndrome, Meniere's Disease, mal de debarquement, benign paroxysmal positional vertigo, and labyrinthitis.

"Blood plasma concentration" refers to the concentration of compounds provided herein in the plasma component of blood of a subject.

"Carrier materials" are excipients that are compatible with the antimicrobial agent, the auris interna and the release profile properties of the auris-acceptable pharmaceutical formulations. Such carrier materials include, e.g., binders, suspending agents, disintegration agents, filling agents, surfactants, solubilizers, stabilizers, lubricants, wetting agents, diluents, and the like. "Auris-pharmaceutically compatible carrier materials" include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

The term "diluent" refers to chemical compounds that are used to dilute the antimicrobial agent prior to delivery and which are compatible with the auris interna.

"Dispersing agents," and/or "viscosity modulating agents" are materials that control the diffusion and homogeneity of the antimicrobial agent through liquid media. Examples of diffusion facilitators/dispersing agents include but are not limited to hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropyl cellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose are also be used as dispersing agents. Dispersing agents useful in liposomal dispersions and self-emulsifying dispersions of the antimicrobial agents disclosed herein are dimyristoyl phosphatidyl choline, natural phosphatidyl choline from eggs, natural phosphatidyl glycerol from eggs, cholesterol and isopropyl myristate.

"Drug absorption" or "absorption" refers to the process of movement of the antimicrobial agents from the localized site of administration, by way of example only, the round window membrane of the inner ear, and across a barrier (the round window membranes, as described below) into the auris interna or inner ear structures. The terms "co-administration" or the like, as used herein, are meant to encompass administration of the antimicrobial agents to a single patient, and are intended to include treatment regimens in which the antimicrobial agents are administered by the same or different route of administration or at the same or different time.

The terms "effective amount" or "therapeutically effective amount," as used herein, refer to a sufficient amount of the active agent or otic agent (e.g., an antimicrobial agent, an anti-inflammatory agent) being administered that would be expected to relieve to some extent one or more of the symptoms of the disease or condition being treated. For example, the result of administration of an antimicrobial agent disclosed herein is reduction and/or alleviation of the signs, symptoms, or causes of tinnitus or balance disorders. For example, an "effective amount" for therapeutic uses is the amount of antimicrobial agent, including a formulation as disclosed herein required to provide a decrease or amelioration in disease symptoms without undue adverse side effects. The term "therapeutically effective amount" includes, for example, a prophylactically effective amount. An "effective amount" of an antimicrobial agent disclosed herein is an amount effective to achieve a desired pharmacologic effect or therapeutic improvement without undue adverse side effects. It is understood that "an effective amount" or "a therapeutically effective amount" varies, in some embodiments, from subject to subject, due to variation in metabolism of the compound administered, age, weight, general condition of the subject, the condition being treated, the severity of the condition being treated, and the judgment of the prescribing physician. It is also understood that "an effective amount" in an extended-release dosing format may differ from "an effective amount" in an immediate release dosing format based upon pharmacokinetic and pharmacodynamic considerations.

The terms "enhance" or "enhancing" refers to an increase or prolongation of either the potency or duration of a desired effect of antimicrobial agent, or a diminution of any adverse symptomatology that is consequent upon the administration of the therapeutic agent. Thus, in regard to enhancing the effect of the antimicrobial agents disclosed herein, the term "enhancing" refers to the ability to increase or prolong, either in potency or duration, the effect of other therapeutic agents that are used in combination with the antimicrobial agent disclosed herein. An "enhancing-effective amount," as used herein, refers to an amount of antimicrobial agent or other therapeutic agent which is adequate to enhance the effect of another therapeutic agent or antimicrobial agent of the target auris structure in a desired system. When used in a patient, amounts effective for this use will depend on the severity and course of the disease, disorder or condition, previous therapy, the patient's health status and response to the drugs, and the judgment of the treating physician.

The term "inhibiting" includes preventing, slowing, or reversing the development of a condition, for example, or advancement of a condition in a patient necessitating treatment.

The terms "kit" and "article of manufacture" are used as synonyms.

"Pharmacodynamics" refers to the factors which determine the biologic response observed relative to the concentration of drug at the desired site within the auris media and/or auris interna.

"Pharmacokinetics" refers to the factors which determine the attainment and maintenance of the appropriate concentration of drug at the desired site within the auris media and/or auris interna.

As used herein, the term "antimicrobial agent" refers to compounds that inhibit the growth, proliferation, or multiplication of microbes, or that kill microbes. Suitable "antimicrobial agents" may be antibacterial agents (effective against bacteria), antiviral agents (effective against viruses), antifungal agents (effective against fungi), antiprotozoal (effective against protozoa), and/or antiparasitic to any class of microbial parasites. "Antimicrobial agents" may work by any suitable mechanism against the microbes, including by being toxic or cytostatic.

The phrase "antimicrobial small molecule" refers to antimicrobial compounds that are of relatively low molecular weight, e.g., less than 1,000 molecular weight, that are effective for the treatment of otic disorders, particularly otic disorders caused by pathogenic microbes, and are suitable for use in the formulations disclosed herein. Suitable "antimicrobial small molecules" include antibacterial, antiviral, antifungal, antiprotozoal, and antiparasitic small molecules.

The term "otic intervention" means an external insult or trauma to one or more auris structures and includes implants, otic surgery, injections, cannulations, or the like. Implants include auris-interna or auris-media medical devices, examples of which include cochlear implants, hearing sparing devices, hearing-improvement devices, tympanostomy tubes, short electrodes, micro-prostheses or piston-like prostheses; needles; stem cell transplants; drug delivery devices; any cell-based therapeutic; or the like. Otic surgery includes middle ear surgery, inner ear surgery, typanostomy, cochleostomy, labyrinthotomy, mastoidectomy, stapedectomy, stapedotomy, endolymphatic sacculotomy or the like. Injections include intratympanic injections, intracochlear injections, injections across the round window membrane or the like. Cannulations include intratympanic, intracochlear, endolymphatic, perilymphatic or vestibular cannulations or the like.

In prophylactic applications, compositions comprising the antimicrobial agents described herein are administered to a patient susceptible to or otherwise at risk of a particular disease, disorder or condition. For example, such conditions include and are not limited to otitis externa, otitis media, Ramsay Hunt syndrome, otosyphilis, AIED, Meniere's disease, and vestibular neuronitis. Such an amount is defined to be a "prophylactically effective amount or dose." In this use, the precise amounts also depend on the patient's state of health, weight, and the like.

As used herein, a "pharmaceutical device" includes any composition described herein that, upon administration to an ear, provides a reservoir for extended release of an active agent described herein.

The term "substantially low degradation products" means less than 5% by weight of the active agent are degradation products of the active agent. In further embodiments, the term means less than 3% by weight of the active agent are degradation products of the active agent. In yet further embodiments, the term means less than 2% by weight of the active agent are degradation products of the active agent. In further embodiments, the term means less than 1% by weight of the active agent are degradation products of the active agent. In some embodiments, any individual impurity (e.g., metal impurity, degradation products of active agent and/or excipients, or the like) present in a formulation described herein is less than 5%, less than 2%, or less than 1% by weight of the active agent. In some embodiments the formulation does not contain precipitate during storage or change in color after manufacturing and storage.

As used herein "essentially in the form of micronized powder" includes, by way of example only, greater than 70% by weight of the active agent is in the form of micronized particles of the active agent. In further embodiments, the term means greater than 80% by weight of the active agent is in the form of micronized particles of the active agent. In yet further embodiments, the term means greater than 90% by weight of the active agent is in the form of micronized particles of the active agent.

The mean residence time (MRT) is the average time that molecules of an active agent (e.g., a microbial agent) reside in an otic structure after a dose.

A "prodrug" refers to an antimicrobial agent that is converted into the parent drug in vivo. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. In one embodiment, the prodrug is designed to alter the metabolic stability or the transport characteristics of a drug, to mask side effects or toxicity, or to alter other characteristics or properties of a drug. Compounds provided herein, in some embodiments, are derivatized into suitable prodrugs.

"Solubilizers" refer to auris-acceptable compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like that assist or increase the solubility of the antimicrobial agents disclosed herein.

"Stabilizers" refers to compounds such as any antioxidation agents, buffers, acids, preservatives and the like that are compatible with the environment of the auris interna. Stabilizers include but are not limited to agents that will do any of (1) improve the compatibility of excipients with a container, or a delivery system, including a syringe or a glass bottle, (2) improve the stability of a component of the composition, or (3) improve formulation stability.

"Steady state," as used herein, is when the amount of drug administered to the auris interna is equal to the amount of drug eliminated within one dosing interval resulting in a plateau or constant levels of drug exposure within the targeted structure.

As used herein, the term "subject" is used to mean an animal, preferably a mammal, including a human or non-human. The terms patient and subject may be used interchangeably.

"Surfactants" refer to compounds that are auris-acceptable, such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants are included to enhance physical stability or for other purposes.

The terms "treat," "treating" or "treatment," as used herein, include alleviating, abating or ameliorating a disease or condition, for example tinnitus, symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Other objects, features, and advantages of the methods and compositions described herein will become apparent from the following detailed description. It should be understood, however, that the detailed description and the specific examples, while indicating specific embodiments, are given by way of illustration only.

Anatomy of the Ear

Figure 4:
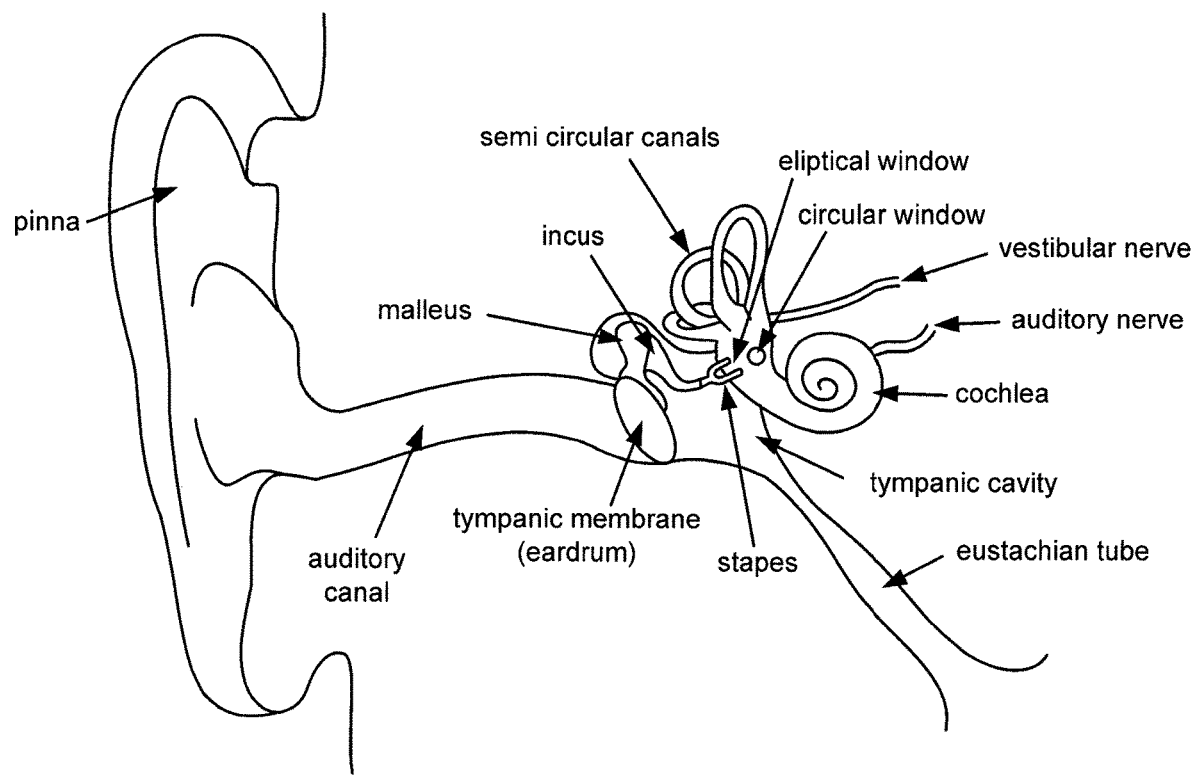
FIG. 4 illustrates the anatomy of the ear

As shown in FIG. 4, the outer ear is the external portion of the organ and is composed of the pinna (auricle), the auditory canal (external auditory meatus) and the outward facing portion of the tympanic membrane, also known as the ear drum. The pinna, which is the fleshy part of the external ear that is visible on the side of the head, collects sound waves and directs them toward the auditory canal. Thus, the function of the outer ear, in part, is to collect and direct sound waves towards the tympanic membrane and the middle ear.

The middle ear is an air-filled cavity, called the tympanic cavity, behind the tympanic membrane. The tympanic membrane, also known as the ear drum, is a thin membrane that separates the external ear from the middle ear. The middle ear lies within the temporal bone, and includes within this space the three ear bones (auditory ossicles): the malleus, the incus and the stapes. The auditory ossicles are linked together via tiny ligaments, which form a bridge across the space of the tympanic cavity. The malleus, which is attached to the tympanic membrane at one end, is linked to the incus at its anterior end, which in turn is linked to the stapes. The stapes is attached to the oval window, one of two windows located within the tympanic cavity. A fibrous tissue layer, known as the annular ligament connects the stapes to the oval window. Sound waves from the outer ear first cause the tympanic membrane to vibrate. The vibration is transmitted across to the cochlea through the auditory ossicles and oval window, which transfers the motion to the fluids in the auris interna. Thus, the auditory ossicles are arranged to provide a mechanical linkage between the tympanic membrane and the oval window of the fluid-filled auris interna, where sound is transformed and transduced to the auris interna for further processing. Stiffness, rigidity or loss of movement of the auditory ossicles, tympanic membrane or oval window leads to hearing loss, e.g. otosclerosis, or rigidity of the stapes bone.

The tympanic cavity also connects to the throat via the eustachian tube. The eustachian tube provides the ability to equalize the pressure between the outside air and the middle ear cavity. The round window, a component of the auris interna but which is also accessible within the tympanic cavity, opens into the cochlea of the auris interna. The round window is covered by round window membrane, which consists of three layers: an external or mucous layer, an intermediate or fibrous layer, and an internal membrane, which communicates directly with the cochlear fluid. The round window, therefore, has direct communication with the auris interna via the internal membrane.

Movements in the oval and round window are interconnected, i.e. as the stapes bone transmits movement from the tympanic membrane to the oval window to move inward against the auris interna fluid, the round window (round window membrane) is correspondingly pushed out and away from the cochlear fluid. This movement of the round window allows movement of fluid within the cochlea, which leads in turn to movement of the cochlear inner hair cells, allowing hearing signals to be transduced. Stiffness and rigidity in round window membrane leads to hearing loss because of the lack of ability of movement in the cochlear fluid. Recent studies have focused on implanting mechanical transducers onto the round window, which bypasses the normal conductive pathway through the oval window and provides amplified input into the cochlear chamber.

Auditory signal transduction takes place in the auris interna. The fluid-filled auris interna, or inner ear, consists of two major components: the cochlear and the vestibular apparatus. The auris interna is located in part within the osseous or bony labyrinth, an intricate series of passages in the temporal bone of the skull. The vestibular apparatus is the organ of balance and consists of the three semi-circular canals and the vestibule. The three semi-circular canals are arranged relative to each other such that movement of the head along the three orthogonal planes in space can be detected by the movement of the fluid and subsequent signal processing by the sensory organs of the semi-circular canals, called the crista ampullaris. The crista ampullaris contains hair cells and supporting cells, and is covered by a dome-shaped gelatinous mass called the cupula. The hairs of the hair cells are embedded in the cupula. The semi-circular canals detect dynamic equilibrium, the equilibrium of rotational or angular movements.

When the head turns rapidly, the semicircular canals move with the head, but endolymph fluid located in the membranous semi-circular canals tends to remain stationary. The endolymph fluid pushes against the cupula, which tilts to one side. As the cupula tilts, it bends some of the hairs on the hair cells of the crista ampullaris, which triggers a sensory impulse. Because each semicircular canal is located in a different plane, the corresponding crista ampullaris of each semi-circular canal responds differently to the same movement of the head. This creates a mosaic of impulses that are transmitted to the central nervous system on the vestibular branch of the vestibulocochlear nerve. The central nervous system interprets this information and initiates the appropriate responses to maintain balance. Of importance in the central nervous system is the cerebellum, which mediates the sense of balance and equilibrium.

The vestibule is the central portion of the auris interna and contains mechanoreceptors bearing hair cells that ascertain static equilibrium, or the position of the head relative to gravity. Static equilibrium plays a role when the head is motionless or moving in a straight line. The membranous labyrinth in the vestibule is divided into two sac-like structures, the utricle and the saccule. Each structure in turn contains a small structure called a macula, which is responsible for maintenance of static equilibrium. The macula consists of sensory hair cells, which are embedded in a gelatinous mass (similar to the cupula) that covers the macula. Grains of calcium carbonate, called otoliths, are embedded on the surface of the gelatinous layer.

When the head is in an upright position, the hairs are straight along the macula. When the head tilts, the gelatinous mass and otoliths tilts correspondingly, bending some of the hairs on the hair cells of the macula. This bending action initiates a signal impulse to the central nervous system, which travels via the vestibular branch of the vestibulocochlear nerve, which in turn relays motor impulses to the appropriate muscles to maintain balance.

The cochlea is the portion of the auris interna related to hearing. The cochlea is a tapered tube-like structure which is coiled into a shape resembling a snail. The inside of the cochlea is divided into three regions, which is further defined by the position of the vestibular membrane and the basilar membrane. The portion above the vestibular membrane is the scala vestibuli, which extends from the oval window to the apex of the cochlea and contains perilymph fluid, an aqueous liquid low in potassium and high in sodium content. The basilar membrane defines the scala tympani region, which extends from the apex of the cochlea to the round window and also contains perilymph. The basilar membrane contains thousands of stiff fibers, which gradually increase in length from the round window to the apex of the cochlea. The fibers of the basement membrane vibrate when activated by sound. In between the scala vestibuli and the scala tympani is the cochlear duct, which ends as a closed sac at the apex of the cochlea. The cochlear duct contains endolymph fluid, which is similar to cerebrospinal fluid and is high in potassium.

The organ of Corti, the sensory organ for hearing, is located on the basilar membrane and extends upward into the cochlear duct. The organ of Corti contains hair cells, which have hairlike projections that extend from their free surface, and contacts a gelatinous surface called the tectorial membrane. Although hair cells have no axons, they are surrounded by sensory nerve fibers that form the cochlear branch of the vestibulocochlear nerve (cranial nerve VIII).

As discussed, the oval window, also known as the elliptical window communicates with the stapes to relay sound waves that vibrate from the tympanic membrane. Vibrations transferred to the oval window increases pressure inside the fluid-filled cochlea via the perilymph and scala vestibuli/ scala tympani, which in turn causes the round window membrane to expand in response. The concerted inward pressing of the oval window/outward expansion of the round window allows for the movement of fluid within the cochlea without a change of intra-cochlear pressure. However, as vibrations travel through the perilymph in the scala vestibuli, they create corresponding oscillations in the vestibular membrane. These corresponding oscillations travel through the endolymph of the cochlear duct, and transfer to the basilar membrane. When the basilar membrane oscillates, or moves up and down, the organ of Corti moves along with it. The hair cell receptors in the Organ of Corti then move against the tectorial membrane, causing a mechanical deformation in the tectorial membrane. This mechanical deformation initiates the nerve impulse which travels via the vestibulocochlear nerve to the central nervous system, mechanically transmitting the sound wave received into signals that are subsequently processed by the central nervous system.

Diseases

Otic disorders, including auris interna, auris media, and auris externa disorders, produce symptoms which include but are not limited to hearing loss, nystagmus, vertigo, tinnitus, inflammation, swelling, infection and congestion. These disorders may have many causes, such as infection, injury, inflammation, tumors and adverse response to drugs or other chemical agents.

Inflammatory Disorders of the Ear

Otitis externa (OE), also referred to as swimmer's ear, is an inflammation and/or infection of the external ear. OE is often caused by bacteria in the outer ear, which establish infection following damage to the skin of the ear canal. Primary bacterial pathogens that cause OE are *Pseudomonas aeruginosa* and *Staphylococcus aureus*, but the condition is associated with the presence of many other strains of gram positive and negative bacteria. OE is also sometimes caused by fungal infection in the outer ear, including *Candida albicans* and *Aspergillus*. Symptoms of OE include otalgia, swelling, and otorrhea. If the condition progresses significantly, OE may cause temporary conductive hearing loss as a result of the swelling and discharge.

Treatment of OE involves eliminating the aggravating pathogen from the ear canal and reducing inflammation, which is usually accomplished by administering combinations of antimicrobial agents, e.g., antibacterial and antifungal agents, with anti-inflammatory agents, e.g., steroids. Typical antibacterial agents for the treatment of OE include aminoglycosides (e.g., neomycin, gentamycin, and tobramycin), polymyxins (e.g., polymyxin B), fluoroquinolone (e.g., ofloxacin, ciprofloxacin, levofloxacin, trovafloxacin), cephalosporins (e.g., cefuroxime, ceflacor, cefprozil, loracarbef, cefindir, cefixime, cefpodoxime proxetil, cefibuten, and ceftriaxone), penicillins (e.g., amoxicillin, amoxicillin-clavulanate, and penicillinase-resistant penicillins), and combinations thereof. Typical antifungal agents for the treatment of OE include clotrimazole, thimerasol, M-cresyl acetate, tolnaftate, itraconazole, and combinations thereof. Acetic acid is also administered to the ear, alone and in combination with other agents, to treat bacterial and fungal infections. Ear drops are often used as the vehicle for administration of the active agents. In the case that ear swelling has progressed substantially and ear drops do not penetrate significantly into the ear canal, a wick can be inserted into the ear canal to facilitate penetration of the treatment solutions. Oral antibiotics are also administered in the case of extensive soft tissue swelling that extends to the face and neck. When the pain of OE is extremely severe such that it interferes with normal activity, e.g., sleeping, pain relievers such as topical analgesics or oral narcotics may be given until the underlying inflammation and infection are alleviated.

Notably, some types of topical ear drops, such as ear drops containing neomycin, are safe and effective for use in the ear canal, but can be irritating and even ototoxic to the auris media, prompting concern that such topical preparations should not be used unless the tympanic membrane is known to be intact. Utilization of the formulations disclosed herein for the treatment of OE allows for use of active agents that are potentially damaging to the auris media, even when the tympanic membrane is not intact. Specifically, the controlled release formulations disclosed herein can be applied locally in the external ear with improved retention time, thus eliminating concern that the active agents will leak out of the ear canal into the auris media. Furthermore, otoprotectants can be added when ototoxic agents, such as neomycin, are used.

Treatment of severe OE with the antimicrobial compositions disclosed herein, particularly highly viscous and/or mucoadhesive formulations, also obviates the need for extended use of an ear wick. Specifically, the compositions disclosed herein have increased retention time in the ear canal as a result of the formulation technology, thus eliminating the need for a device to maintain their presence in the outer ear. The formulations can be applied in the outer ear with a needle or an ear dropper, and the active agents can be maintained at the site of inflammation without the aid of an ear wick. In some embodiments, antimicrobial agent compositions described herein further comprise anti-inflammatory agents and are useful in the treatment of otitis externa.

In some embodiments, the treatment of OE with antimicrobial formulations disclosed herein encompasses the treatment of granular myringitis, a specific form of OE characterized by chronic inflammation of the pars tensa of the tympanic membrane. The outer epithelial and underlying fibrous layers of the tympanic membrane are replaced by a proliferating granulation tissue. The predominant symptom is foul-smelling otorrhea. A variety of bacteria and fungi cause the condition, including *Proteus* and *Psuedomonas* species. Accordingly, antimicrobial agent formulations disclosed herein comprising antibacterial or antifungal agents are useful for the treatment of granular myringitis.

In some embodiments, the treatment of OE with antimicrobial formulations disclosed herein encompasses the treatment of chronic stenosing otitis externa. Chronic stenosing otitis externa is characterized by repeated infections, typically caused by bacteria or fungi. The primary symptoms are pruritus in the ear canal, otorrhea, and chronic swelling. Antimicrobial agent formulations disclosed herein comprising antibacterial or antifungal agents are useful for the treatment of chronic stenosing otitis externa.

In some embodiments, the treatment of OE with antimicrobial formulations disclosed herein encompasses the treatment of malignant or necrotizing external otitis, an infection involving the temporal and adjacent bones. Malignant external otitis is typically a complication of external otitis. It occurs primarily in persons with compromised immunity, especially in older persons with diabetes mellitus. Malignant external otitis is often caused by the bacteria *Pseudomonas aeruginosa*. Treatment typically involves correction of immunosuppression when possible, in conjunction with antibacterial therapy and pain relievers. According, antimicrobial agent formulations disclosed herein are useful for the treatment of malignant or necrotizing external otitis.

Otitis media (OM), which includes acute otitis media (AOM), chronic otitis media, otitis media with effusion (OME), recurrent acute otitis media (RAOM), chronic otitis media with effusion (COME), secretory otitis media, and chronic secretory otitis media as examples, is a condition affecting both adults and children. OM susceptibility is multifactorial and complex, including environmental, microbial and host factors. Bacterial infection accounts for a large percentage of OM cases, with more than 40% of cases attributed to *Streptococcus pneumoniae* infection. However, viruses, as well as other microbes, may also account for OM conditions. In some instances, otitis media is associated with eustachian tube dysfunction that is caused by, for example, anatomic blockage to inflammation, secondary to allergies, upper respiratory tract infection (URTI), trauma or the like.

Otitis media with effusion (OME) is characterized by a nonpurulent effusion of the middle ear that may be either mucoid or serous. Symptoms usually involve hearing loss or aural fullness. In children, hearing loss is generally mild and is often detected only with an audiogram. Serous otitis media is a specific type of OME caused by transudate formation as a result of a rapid decrease in middle ear pressure relative to the atmospheric pressure.

Because OM can be caused by a virus, bacteria or both, it is often difficult to identify the exact cause and thus the most appropriate treatment. Treatment options for OM include antibiotics, such as penicillins (e.g., amoxicillin and amoxicillin-clavulanate), clavulanate acid, trimethoprim-sulfamethoxazole, fluoroquinolone (e.g., ofloxacin, ciprofloxacin, levofloxacin, trovafloxacin), cephalosporins (e.g., cefuroxime, ceflacor, cefprozil, loracarbef, cefindir, cefixime, cefpodoxime proxetil, cefibuten, and ceftriaxone), macrolides and azalides (e.g., erythromycin, clarithromycin, and azithromycin), sulfonamides, and combinations thereof. Surgical intervention is also available, including myringotomy, an operation to insert a tympanostomy tube through the tympanic membrane and into the patient's middle ear to drain the fluid and balance the pressure between the outer and middle ear. Antipyretics and analgesics, including benzocaine, ibuprofen and acetaminophen, may also be prescribed to treat accompanying fever or pain effects. Antimicrobial agent compositions disclosed herein comprising antibacterial or antifungal agents are useful for the treatment of Otitis media (OM), which includes acute otitis media (AOM), chronic otitis media, otitis media with effusion (OME), recurrent acute otitis media (RAOM), chronic otitis media with effusion (COME), secretory otitis media, and chronic secretory otitis media or the like. In some embodiments, antimicrobial agent compositions described herein further comprise anti-inflammatory agents and are useful in the treatment of Otitis media (OM), which includes acute otitis media (AOM), chronic otitis media, otitis media with effusion (OME), recurrent acute otitis media (RAOM), chronic otitis media with effusion (COME), secretory otitis media, and chronic secretory otitis media or the like.

Regardless of the causative agent, increases in cytokine production, including interleukins and TNF, have been observed in the effluent media of individuals afflicted with OM. IL-1β, IL-6 and TNF-α are acute-phase cytokines that promote acute inflammatory response after infection with viruses and bacteria. Moreover, higher TNF-α levels have been associated with a history of multiple tympanostomy tube placements, indicating a role for TNF-α in chronic OM cases. Finally, direct injection of TNF-α and interleukins has been shown to induce middle ear inflammation in a guinea pig model. These studies support the role that cytokines may play in the origin and maintenance of OM in the auris media. Thus, treatment of OM includes the use of antimicrobial agents in conjunction with anti-inflammatory agents to eliminate the pathogen and treat the symptoms of inflammation. Such treatments include use of steroids, TNF-α inhibitors, platelet activating factor antagonists, nitric oxide synthase inhibitors, histamine antagonists, and combinations thereof in conjunction with the antimicrobial formulations disclosed herein.

Mastoiditis is an infection of the mastoid process, which is the portion of the temporal bone behind the ear. It is typically caused by untreated acute otitis media. Mastoiditis may be acute or chronic. Symptoms include pain, swelling, and tenderness in the mastoid region, as well as otalgia, erythematous, and otorrhea. Mastoiditis typically occurs as bacteria spread from the middle ear to the mastoid air cells, where the inflammation causes damage to the bony structures. The most common bacterial pathogens are *Streptococcus pneumoniae, Streptococcus pyogenes, Staphylococcus aureus*, and gram-negative bacilli. Accordingly, antimicrobial agent formulations disclosed herein comprising antibacterial agents effective against the bacteria are useful for the treatment of mastoiditis, including acute mastoiditis and chronic mastoiditis.

Bullous myringitis is an infection of the tympanic membrane, caused by a variety of bacteria and viruses, including *Mycoplasma* bacteria. The infection leads to inflammation of the tympanic membrane and nearby canal, and causes the formation of blisters on the ear drum. The primary symptom of Bullous myringitis is pain, which may be relieved through the administration of analgesics. Antimicrobial formulations disclosed herein comprising antibacterial and antiviral agents are useful for the treatment of Bullous myringitis.

Eustachian tubal catarrh, or Eustachian salpingitis, is caused from inflammation and swelling of the Eustachian tubes, resulting in a build-up of catarrh. Accordingly, antimicrobial formulations disclosed herein are useful for the treatment of Eustachian salpingitis.

Labyrinthitis, e.g., serous labyrinthitis, is an inflammation of the inner ear that involves one or more labyrinths housing the vestibular system. The primary symptom is vertigo, but the condition is also characterized by hearing loss, tinnitus, and nystagmus. Labrynthitis maybe acute, lasting for one to six weeks and being accompanied by severe vertigo and vomiting, or chronic, with symptoms lasting for months or even years. Labyrinthitis is typically caused by viral or bacterial infection. Accordingly, antimicrobial formulations disclosed herein comprising antibacterial and antiviral agents are useful for the treatment of labyrinthitis.

Facial nerve neuritis is a form of neuritis, an inflammation of the peripheral nervous system, afflicting the facial nerve. The primary symptoms of the condition are a tingling and burning sensation, and stabbing pains in the affected nerves. In severe cases, there may be numbness, loss of sensation, and paralysis of the nearby muscles. The condition is typically caused by herpes zoster or herpes simplex viral infection, but has also been associated with bacterial infection, e.g., leprosy. Accordingly, antimicrobial formulations disclosed herein comprising antibacterial and antiviral agents are useful for the treatment of facial nerve neuritis.

In some embodiments, antimicrobial formulations disclosed herein are also useful for the treatment of temporal bone osteoradionecrosis.

Ramsay Hunt Syndrome (Herpes Zoster Oticus)

Ramsay Hunt syndrome is caused by a herpes zoster infection of the auditory nerve. The infection may cause severe ear pain, hearing loss, vertigo, blisters on the outer ear, in the ear canal, as well as on the skin of the face or neck supplied by the nerves. Facial muscles may also become paralyzed if the facial nerves are compressed by the swelling. Hearing loss may be temporary or permanent, with vertigo symptoms usually lasting from several days to weeks.

Treatment of Ramsay Hunt's syndrome includes administration of antiviral agents, such as ganciclovir, acyclovir, famciclovir and valacyclovir. Antiviral agents may be given in combination with agents that treat symptoms of the infection, such as corticosteroids, analgesics and narcotics to relieve the pain, and scopolamine, diazempam, or other central nervous system agents to suppress vertigo. Capsaicin, lidocaine patches and nerve blocks may also be used. Surgery may be performed on compressed facial nerves to relieve facial paralysis.

Otosyphilis

Syphilis is a venereal disease, caused by the spirochete *Treponema pallidum*, which in its secondary and tertiary stages may result in otic disorders, particularly cochleovestibular disorders, due to membranous labyrinthitis, and secondarily meningitis. Both acquired and congenital syphilis can cause otic disorders. Symptoms of cochleovestibular disorders resulting from syphilis are often similar to those of other otic disorders, such as AIED and Meniere's disease, and include tinnitus, deafness, vertigo, malaise, sore throat, headaches, and skin rashes. Syphilis infection may lead to congenital prenatal hearing loss, affecting approximately 11.2 per 100,000 live births in the United States, as well as sudden hearing loss in adults.

Treatment of otosyphilis (syphilis presenting otic symptoms) typically includes a combination of steroids (e.g., prednisilone) and antibacterial agents (e.g., benzathine penicillin G (BICILLIN LA®), penicillin G procaine, doxycycline, tetracycline, ceftriaxone, azithromycin). Such treatments may be effective in eradicating the spirochete organism. However, Treponemas may remain in the cochlear and vestibular endolymph even after eradication from other sites in the body. Accordingly, long term treatment with penicillins may be required to achieve complete eradication of the spirochete organism from the endolymph fluid. Also, in the case of a severe or advanced case of syphilis, a uricosuric drug, such as probenecid, may be administered in conjunction with the antibacterial agent to increase its efficacy.

Other Microbial Infections Causing Cochleovestibular Disorders

Other microbial infections are known to cause cochleovestibular disorders, including hearing loss. Such infections include rubella, cytomegalovirus, mononucleosis, varicella zoster (chicken pox), pneumonia, *Borrelia* species of bacteria (Lyme disease), and certain fungal infections. Accordingly, controlled release antimicrobial agent formulations disclosed herein are also used for localized treatment of these infections in the ear.

Autoimmune Inner Ear Disease

Autoimmune inner ear disease (AIED) is one of the few reversible causes of sensorineural hearing loss. It is a disorder appearing in both adults and children that often involves a bilateral disturbance of the audio and vestibular functions of the auris interna. In many cases, AIED occurs without systemic autoimmune symptoms, but up to one-third of patients also suffer from a systemic autoimmune illness, such as inflammatory bowel disease, rheumatoid arthritis, Ankylosing spondylitis, Systemic Lupus Erythematosus (SLE), Sjögren's Syndrome, Cogan's disease, ulcerative colitis, Wegener's granulomatosis and scleroderma. Behcet's disease, a multisystem disease, also commonly has audiovestibular problems. A classification scheme for AIED has been developed (Harris and Keithley *Otorhinolaryngology Head and Neck Surgery* (2002) 91, 18-32).

The immune system normally performs a crucial role in protecting the inner ear from invasive pathogens such as bacteria and viruses. However, in AIED the immune system itself begins to damage the delicate inner ear tissues. The inner ear is fully capable of mounting a localized immune response to foreign antigens. When a foreign antigen enters the inner ear, it is first processed by immunocompetent cells which reside in and around the endolymphatic sac. Once the foreign antigen has been processed by these immunocompetent cells, these cells secrete various cytokines which modulate the immune response of the inner ear. One result of this cytokine release is to facilitate the influx of inflammatory cells, which are recruited from the systemic circulation. These systemic inflammatory cells enter the cochlea via diapedesis through the spiral modiolar vein and its tributaries, and begin to participate in antigen uptake and deregulation just as it occurs in other parts of the body. Interleukin 1 (IL-1) plays an important role in modulating the innate (nonspecific) immune response and is a known activator of resting T helper cells and B-cells. T helper cells, once activated by IL-1, produce IL-2. IL-2 secretion results in differentiation of pluripotent T-cells into helper, cytotoxic and suppressor T-cell subtypes. IL-2 also assists T helper cells in the activation of B lymphocytes and probably plays a pivotal role in the immunoregulation of the immune response of the vestibular and cochlear regions. IL-2 is within the perilymph of the auris interna as early as 6 h after antigen challenge with peak levels at 18 h after antigen challenge. The perilymphatic levels of IL-2 then dissipate, and it is no longer present within the perilymph at 120 hours post antigen challenge.

Both IL-1β and tumor necrosis factor-α (TNF-α) may play a key role in the initiation and amplification of the immune response. IL-1β is expressed by the fibrocytes of the spiral ligament in the presence of trauma such as surgical trauma or acoustic trauma in a nonspecific response. TNF-α is expressed either by infiltrating systemic cells or by resident cells contained within the endolymphatic sac in the presence of antigen. TNF-α is released as part of the adaptive (specific) immune response in animal models. When antigen is injected into the auris interna of mice, IL-1β and TNF-α are both expressed and a vigorous immune response occurs. However, when antigen is introduced to the auris interna via the cerebral spinal fluid in the absence of trauma, only TNF-α is expressed and the immune response in minimal. Importantly, cochlear trauma in isolation also results in a minimal immune response. These results suggest that both the nonspecific and specific components of the immune response act in concert in the auris interna to achieve a maximal response.

Thus, if the cochlea is traumatized and an antigen is injected (or in the case of autoimmune disease, the patient has immune cells directed against inner ear antigens), both the nonspecific and the specific immune responses can be activated simultaneously. This results in the concurrent production of IL-1β as well as TNF-α which causes a greatly amplified level of inflammation leading to substantial damage to the auris interna.

Certain evidence suggests that viral infection is a factor in the initiation of the inflammatory response that results in AIED. Various autoimmune conditions are induced or enhanced by a variety of DNA and RNA virus infections. Acute or persistent viral infections induce or enhance autoimmune diseases in animal models as well. Similar antigenic determinants have also been observed on viruses and host components. Oldstone, M. B. A. *J. Autoimmun.* (1989) 2(suppl): 187-194. Further, serological tests have identified viral infection in at least one patient diagnosed with a systemic autoimmune disorder that is often associated with AIED (Cogan's syndrome). Garcia-Berrocal, et al. *O.R.L.* (2008) 70: 16-20.

Accordingly, in some embodiments, controlled release antimicrobial agent compositions and formulations disclosed herein are administered for the treatment of AIED. Particularly, in certain embodiments, formulations disclosed herein comprising antiviral agents are administered for treatment of AIED. In other embodiments, the antimicrobial agent formulations disclosed herein are administered for the treatment of AIED in conjunction with other pharmaceutical agents useful for treating the same conditions or symptoms of the same conditions, including steroids, cytotoxic agents, collagen, gamma globulin infusion, or other immune modulating drugs. Steroids include, e.g., prednisone or decadron. Cytotoxic agents for the treatment of AIED include, e.g., methotrexate, cyclophosphamide, and thalidomide. Plasmapheresis procedures are optionally used. Treatment with oral collagen, gamma globulin infusions, or other immune modulating drugs (e.g. beta-interferon, alpha-interferon or copaxone) is also optionally used in combination with the antimicrobial agent formulations disclosed herein. The additional pharmaceutical agents are optionally administered together with the controlled release formulations disclosed herein, or through other modes of administration, e.g., orally, by injection, topically, nasally or through any other suitable means. The additional pharmaceutical agents are optionally co-administered, or administered at different time periods.

Meniere's Disease

Meniere's disease is characterized by sudden attacks of vertigo, nausea and vomiting that may last for 3 to 24 hours, and may subside gradually. Progressive hearing loss, tinnitus and a sensation of pressure in the ears accompanies the disease through time. The cause of symptoms associated with Meniere's disease is likely an imbalance of inner ear fluid homeostasis, including an increase in production or a decrease in reabsorption of inner ear fluid.

Although the cause of Meniere's disease is unknown, certain evidence suggests a viral etiology for the disease. Specifically, histopathologic analysis of temporal bones in patients with Meniere's disease revealed viral ganglionitis. Also, viral DNA has been observed in the ganglia of patients with Meniere's disease at a higher rate than in healthy patients. Oliveira et al. *ORL* (2008) 70: 42-51. Based on these studies, a pilot study of intratympanic injection of the antiviral agent ganciclovir was conducted, resulting in an improvement of patients suffering from Meniere's disease. Guyot et al. *ORL* (2008) 70: 21-27. Accordingly, controlled release formulations disclosed herein comprising antiviral agents, e.g., ganciclvir, acyclovir, famovir, and valgancyclovir, can be administered to the ear for localized treatment of Meniere's disease.

Other treatments of Meniere's disease are aimed at dealing with the immediate symptoms and prevention of recurrence. Low-sodium diets, avoidance of caffeine, alcohol, and tobacco have been advocated. Medications that temporarily relieve vertigo attacks include antihistamines (e.g., meclizine), and central nervous system agents, including barbiturates and/or benzodiazepines (e.g., lorazepam or diazepam). Other examples of drugs that may be useful in relieving symptoms include muscarinic antagonists, including scopolamine. Nausea and vomiting may be relieved by suppositories containing antipsychotic agents, including the phenothiazine agent prochlorperazine (Compazine®, Buccastem, Stemetil and Phenotil). Thus, other treatments of Meniere's disease are optionally used in combination with the controlled release formulations disclosed herein for the treatment of Meniere's disease.

Surgical procedures have also been used to relieve symptoms of Meniere's disease, including destruction of vestibular function to relieve vertigo symptoms. These procedures aim to either reduce fluid pressure in the inner ear and/or to destroy inner ear balance function. An endolymphatic shunt procedure, which relieves fluid pressure, may be placed in the inner ear to relieve symptoms of vestibular dysfunction. Severing of the vestibular nerve may also be employed, which may control vertigo while preserving hearing.

Another approach to destruction of vestibular function for the treatment of severe Meniere's disease is intratympanic application of an agent that destroys sensory hair cell function in the vestibular system, thereby eradicating inner ear balance function. Various antimicrobial agents are used in the procedure, including aminoglycosides such as gentamicin and streptomycin. The agents are injected through the tympanic membrane using a small needle, a tympanostomy tube with or without a wick, or surgical catheters. Various dosing regimens are used to administer the antimicrobial agents, including a low dose method in which less of the agents are administered over longer periods of time (e.g., one month between injections), and high dose methods in which more of the agents are administered over a shorter time frame (e.g., every week). Although the high dose method is typically more effective, it is more risky, as it may result in hearing loss.

Accordingly, formulations disclosed herein are also useful for administration of antimicrobial agents, e.g., gentamicin and streptomycin, for disabling the vestibular apparatus to treat Meniere's disease. The formulations disclosed herein can be used to maintain a steady release of the active agents inside the tympanic membrane, thereby avoiding the need for multiple injections or the insertion of a tympanostomy tube. Further, by keeping the active agents localized in the vestibular system, the formulations disclosed herein can also be used to administer higher doses of the antimicrobial agents with a decreased risk of hearing loss.

Meniere's Syndrome

Meniere's syndrome, which displays similar symptoms as Meniere's disease, is attributed as a secondary affliction to another disease process, e.g. thyroid disease or inner ear inflammation due to syphilis infection. Meniere's syndrome is thus a collection of secondary effects to various processes that interfere with normal production or resorption of endolymph, including microbial infection. Treatment of patients afflicted with Meniere's syndrome is similar to Meniere's disease.

Vestibular Neuronitis

Vestibular neuronitis is characterized by sudden vertigo attacks, which may present as a single attack of vertigo, a series of attacks, or a persistent condition which diminishes over a matter of weeks. Symptoms typically include nausea, vomiting, and previous upper respiratory tract infections, although there are generally no auditory symptoms. Vestibular neuronitis may also be associated with eye nystagmus, a condition characterized by flickering of the eyes involuntarily toward the affected side. It is caused by inflammation of the vestibular nerve, the nerve that connects the inner ear to the brain, and is likely caused by viral infection. Diagnosis of vestibular neuronitis usually involves tests for nystagmus using electronystamography, a method of electronically recording eye movements. Magnetic resonance imaging may also be performed to determine if other causes may play a role in the vertigo symptoms.

Treatment of vestibular neuronitis typically involves alleviating the symptoms of the condition, primarily vertigo, until the condition clears on its own. Treatment of vertigo is often identical to Meniere's disease, and may include meclizine, lorazepam, prochlorperazine, or scopolamine. Fluids and electrolytes may also be intravenously administered if the vomiting is severe. Corticosteroids, such as prednisilone, are also given if the condition is detected early enough.

Compositions disclosed herein comprising an antiviral agent can be administered for the treatment of vestibular neuronitis. Further, the compositions may be administered with other agents that are typically used to treat symptoms of the condition, including anticholinergics, antihistamines, benzodiazepines, or steroids.

Postural Vertigo

Postural vertigo, otherwise known as positional vertigo, is characterized by sudden violent vertigo that is triggered by certain head positions. This condition may be caused by damaged semicircular canals caused by physical injury to the inner ear, otitis media, ear surgery or blockage of the artery to the inner ear.

Vertigo onset in patients with postural vertigo usually develops when a person lies on one ear or tilts the head back to look up. Vertigo may be accompanied by nystagmus. Treatment of postural vertigo often involves the same treatment as in Meniere's disease. In severe cases of postural vertigo, the vestibular nerve is severed to the affected semicircular canal. Treatment of vertigo is often identical to Meniere's disease, and may include meclizine, lorazepam, prochlorperazine or scopolamine. Fluids and electrolytes may also be intravenously administered if the vomiting is severe.

Sensorineural Hearing Loss

Sensorineural hearing loss occurs when the components of the inner ear or accompanying neural components are affected, and may contain a neural (i.e., the auditory nerve or auditory nerve pathways in the brain are affected) or sensory component. Sensory hearing loss may be hereditary, or it may be caused by acoustic trauma (i.e. very loud noises), a viral infection, drug-induced or Meniere's disease. In some instances, noise induced hearing loss is caused by loud noises, for example, gun fire, loud music or other human-based noise. Neural hearing loss may occur as a result of brain tumors, infections, or various brain and nerve disorders, such as stroke. Some hereditary diseases, such as Refsum's disease (defective accumulation of branched fatty acids), may also cause neural disorders affecting hearing loss. Auditory nerve pathways may be damaged by demyelinating diseases, e.g. idiopathic inflammatory demyelinating disease (including multiple sclerosis), transverse myelitis, Devic's disease, progressive multifocal leukoencephalopathy, Guillain-Barre syndrome, chronic inflammatory demyelinating polyneuropathy and anti-MAG perpheral neuropathy.

The incidence of sudden deafness, or sensorineural hearing loss, occurs in about 1 in 5,000 individuals, and may be caused by viral or bacterial infections, e.g. mumps, measles, influenza, chickenpox, cytomegalovirus, syphilis or infectious mononucleosis, or physical injury to the inner ear organ. In some cases, no cause can be identified. Tinnitus and vertigo may accompany sudden deafness, which subsides gradually. Oral corticosteroids are frequently prescribed to treat sensorineural hearing loss. In some cases, surgical intervention may be necessary.

Hereditary Disorders

Hereditary disorders, including Scheibe, Mondini-Michelle, Waardenburg's, Michel, Alexander's ear deformity, hypertelorism, Jervell-Lange Nielson, Refsum's and Usher's syndromes, are found in approximately 20% of patients with sensorineural hearing loss. Congenital ear malformations may result from defects in the development of the membranous labyrinthine, the osseous labyrinthine, or both. Along with profound hearing loss and vestibular function abnormalities, hereditary deformities may also be associated with other dysfunctions, including development of recurring meningitis, cerebral spinal fluid (CSF) leaks, as well as perilymphatic fistulas. Treatment of chronic infections may be necessitated in hereditary disorder patients.

Pharmaceutical Agents

Provided herein are antimicrobial agent compositions and formulations that treat otic disorders and/or their attendant symptoms, including but not limited to infection, hearing loss, nystagmus, vertigo, tinnitus, inflammation, swelling, and congestion. Otic disorders, including AIED, otitis media, otitis externa, Meniere's disease, Ramsay Hunt syndrome, otosyphilis, hereditary disorders and vestibular neuronitis, have causes and symptoms that are responsive to the pharmaceutical agents disclosed herein, or other pharmaceutical agents. Antimicrobial agents that are not disclosed herein but which are useful for the amelioration or eradication of otic disorders are expressly included and intended within the scope of the embodiments presented. In some embodiments, pharmaceutically active metabolites, salts, polymorphs, prodrugs, analogues, and derivatives of the antimicrobial agents disclosed herein that retain the ability of the parent antimicrobial agents to treat otic disorders are useful in the formulations.

Moreover, pharmaceutical agents which have been previously shown to be excessively toxic, harmful or non-effective during systemic or localized application in other organ systems, for example through toxic metabolites formed after hepatic processing, toxicity of the drug in particular organs, tissues or systems, through high levels needed to achieve efficacy, through the inability to be released through systemic pathways, or through poor PK characteristics, are useful in some embodiments. Accordingly, pharmaceutical agents which have limited or no systemic release, systemic toxicity, poor PK characteristics or combinations thereof are contemplated within the scope of the embodiments disclosed herein.

The antimicrobial agent formulations disclosed herein are optionally targeted directly to otic structures where treatment is needed. For example, one embodiment contemplated is the direct application of the antimicrobial agent formulations disclosed herein onto the round window membrane or the crista fenestrae cochlea of the auris interna, allowing direct access and treatment of the auris interna, or inner ear components. In other embodiments, the antimicrobial agent formulations disclosed herein are applied directly to the oval window. In yet other embodiments, direct access is obtained through microinjection directly into the auris interna, for example, through cochlear microperfusion. Such embodiments also optionally comprise using a drug delivery device, wherein the drug delivery device delivers the antimicrobial agent formulations through a needle and syringe, a pump, a microinjection device or any combination thereof, to the target. In still other embodiments, application of the antimicrobial agent formulation is targeted to the auris media through piercing of the intratympanic membrane and applying the antimicrobial agent formulation directly to the auris media structures affected, including the walls of the tympanic cavity or auditory ossicles. By doing so, the antimicrobial agent formulations disclosed herein are confined to the targeted auris media structure, and will not be lost, for example, through diffusion or leakage through the eustachian tube or pierced tympanic membrane. In some embodiments, antimicrobial agent formulations disclosed herein are delivered to the auris externa in any suitable manner, including by cotton swab, injection or ear drops. Also, in other embodiments, the antimicrobial agent formulations are targeted to specific regions of the auris externa by application with a needle and syringe, a pump, a microinjection device, an in situ forming spongy material or any combination thereof. For example, in the case of treatment of otitis externa, antimicrobial agent formulations disclosed herein are delivered directly to the ear canal, where they are retained, thereby reducing loss of the active agents from the target ear structure by drainage or leakage.

Some pharmaceutical agents, either alone or in combination, are ototoxic. For example, some antibiotics, including erythromycin, gentamicin, streptomycin, dihydrostreptomycin, tobramycin, netilmicin, amikacin, neomycin, kanamycin, etiomycin, vancomycin, metronidizole, capreomycin, are mildly to very ototoxic, and affect the vestibular and cochlear structures differentially. However, in some instances, the combination of an ototoxic drug with an otoprotectant lessens the ototoxic effects of the drug. Moreover, localized application of the potentially ototoxic drug lessens the toxic effects that otherwise occur during systemic administration through the use of lower amounts with maintained efficacy, and/or the use of targeted amounts for a shorter period of time.

In formulating a controlled release antimicrobial agent formulation, it is advised to avoid or combine the appropriate excipients, diluents or carriers to lessen or eliminate potential ototoxic components from the formulation, or to decrease the amount of such excipients, diluents or carriers. The ototoxicity of the pharmaceutical agents, excipients, diluents, carriers, or formulations and compositions disclosed herein can be ascertained using an accepted animal model. See, e.g., Maritini, A., et al. *Ann. N.Y. Acad. Sci.* (1999) 884:85-98. In some embodiments, a controlled release antimicrobial agent formulation disclosed herein optionally includes otoprotective agents, such as antioxidants, alpha lipoic acid, calcium, fosfomycin or iron chelators, or other otoprotectant agents, to counteract potential ototoxic effects that may arise from the use of specific therapeutic agents or excipients, diluents or carriers.

Antimicrobial Agents

Any antimicrobial agent useful for the treatment of otic disorders, e.g., inflammatory diseases or infections of the ear, is suitable for use in the formulations and methods disclosed herein. In some embodiments, the antimicrobial agent is an antibacterial agent, an antifungal agent, an antiviral agent, an antiprotozoal agent, and/or an antiparasitic agent. Antimicrobial agents include agents that act to inhibit or eradicate microbes, including bacteria, fungi, viruses, protozoa, and/or parasites. Specific antimicrobial agents may be used to combat specific microbes. Accordingly, a skilled practitioner would know which antimicrobial agent would be relevant or useful depending on the microbe identified, or the symptoms displayed.

In some embodiments, the antimicrobial agent is a protein, a peptide, an antibody, DNA, a carbohydrate, an inorganic molecule, or an organic molecule. In certain embodiments, the antimicrobial agents are antimicrobial small molecules. Typically, antimicrobial small molecules are of relatively low molecular weight, e.g., less than 1,000, or less than 600-700, or between 300-700 molecular weight.

In some embodiments, the antimicrobial agent is an antibacterial agent. In some embodiments, the antibacterial agent treats infections caused by gram positive bacteria. In some embodiments, the antibacterial agent treats infections caused by gram negative bacteria. In some embodiments, the antibacterial agent treats infections caused by mycobacteria. In some embodiments, the antibacterial agent treats infections caused by giardia.

In some embodiments, the antibacterial agent treats infections by inhibiting bacterial protein synthesis. In some embodiments, the antibacterial agent treats infections by disrupting synthesis of bacterial cell wall. In some embodiments, the antibacterial agent treats infections by changing permeability of bacterial cell membranes. In some embodiments, the antibacterial agent treats infections by disrupting DNA replication in bacteria.

In some embodiments, the antibacterial agent is an antibiotic. In some embodiments, the antibiotic is an aminoglycoside. Examples of aminoglycoside antibiotics include and are not limited to amikacin, gentamicin, kanamycin, neomycin, netilmicin, streptomycin, tobramycin, paromycin or the like. In some embodiments, the antibiotic is an ansamycin. Examples of ansamycins include and are not limited to geldanamycin, herbimycin or the like. In some embodiments, the antibiotic is a carbacephem. Examples of carbecephems include and are not limited to loracarbef or the like. In some embodiments, the antibiotic is a carbapenem. Examples of carbapenems include and are not limited to ertapenem, doripenem, imipenem (cilostatin), meropenem or the like. In some embodiments, the antibiotic is a cephalosporin (including, for example, first, second, third, fourth or fifth generation cephalosporins). Examples of cephalosporins include and are not limited to cefaclor, cefamandole, cefotoxin, cefprozil, cefuroxime, cefixime, cefdinir, cefditoren, cefpodoxime, ceftazidime, ceftibuten, ceftizoxime, ceftriaxone, cefepime, ceftobirprole or the like. In some embodiments, the antibiotic is a glycopeptide. Examples of glycopeptides include and are not limited to vancomycin or the like. In some embodiments, the antibiotic is a macrolide antibiotic. Examples of macrolides include and are not limited to azithromycin, clarithromycin, dirithromycin, erythromycin, roxithromycin, troleandomycin, telithromycin, spectinomycin, or the like. In some embodiments, the antibiotic is a monobactam. Examples of monobactams include and are not limited to aztreonam or the like. In some embodiments, the antibiotic is a penicillin. Examples of pencillins include and are not limited to amoxicillin, ampicillin, azociling, carbenicillin, cloxacillin, dicloxacillin, flucloxacillin, mezlocillin, meticillin, nafcillin, oxacillin, peperacillin, ticarcillin or the like. In some embodiments, the antibiotic is a polypeptide. Examples of polypeptide antibiotics include and are not limited to bacitracin, colistin, polymyxin B or the like. In some embodiments, the antibiotic is a quinolone. Examples of quinolones include and are not limited to ciprofloxacin, enoxacin, gatifloxacin, levofloxacin, lomefloxacin, moxifloxacin, norfloxacin, ofloxacin, trovafloxacin, grepafloxacin, sparfloxacin, AL-15469A, AL-38905 or the like. In some embodiments, the antibiotic is a sulfonamide. Examples of suflonamides include and are not limited to afenide, prontosil, sulfacetamide, sulfamethiazole, sulfanilimide, sulfasalazine, sulfisoxazole, trimethoprim, cotrimoxazole or the like. In some embodiments, the antibiotic is a tetracycline antibiotic. Examples of tetracyclines include are not limited to demeclocycline, doxycycline, minocycline, oxytetracycline, tetraycline or the like. In some embodiments, the antibiotic is an oxazolidinone antibiotic. Examples of oxazolidinone antibiotics include and are not limited to linezolid or the like. In some embodiments, the antibiotic is arsogebanubem chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin, dalfopristin, rifampicin, thamphenicol, tinidazole or the like.

Antibacterial agents include amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilmde, sulfsalazine, sulfsioxazole, trimethoprim, demeclocycline, doxycycline, minocycline, oxtetracycline, tetraycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin, tinidazole, and combinations thereof.

In some embodiments, an antibiotic compatible with the compositions described herein is a broad spectrum antibiotic. In some embodiments, an antibiotic compatible with the compositions described herein is effective in treating infections that are resistant to other classes of antibiotics. For example, in some instances, vancomycin is effective in treating infections caused by methicillin resistant *staphyloccocus aureus* bacteria. In some embodiments, intratympanic administration of an antibiotic composition described herein reduces the risk of development of antibiotic resistance that is seen with systemic treatments.

In specific embodiments, an antibiotic used in compositions or devices described herein is ciprofloxacin (Cipro). In specific embodiments, an antibiotic used in compositions or devices described herein is gentamicin. In specific embodiments, an antibiotic used in compositions or devices described herein is a penicillin. In specific embodiments, an antibiotic used in compositions or devices described herein is streptomycin.

In some embodiments, an antimicrobial agent is a peptide or a lantibiotic including, by way of example, Maximin H5, Dermcidin, Cecropins, andropin, moricin, ceratotoxin and melittin, Magainin, dermaseptin, bombinin, brevinin-1, esculentins and buforin II, CAP18, LL37, abaecin, apidaecins, prophenin, indolicidin, brevinins, protegrin, tachyplesins, defensins, drosomycin, alamethicin, pexiganan or MSI-78, and other MSI peptides like MSI-843 and MSI-594, polyphemusin, Class III and III bacterocins like: colicin, pyocin, klebicin, subtilin, epidermin, herbicolacin, brevicin, halocin, agrocin, alveicin, carnocin, curvaticin, divercin, enterocin, enterolysin, erwiniocin, glycinecin, lactococin, lacticin, leucoccin, mesentericin, pediocin, plantaricin, sakacin, sulfolobicin, vibriocin, warnerinand, nisin or the like.

Antiviral agents include acyclovir, famciclovir and valacyclovir. Other antiviral agents include abacavir, aciclovir, adfovir, amantadine, amprenavir, arbidol, atazanavir, artipla, brivudine, cidofovir, combivir, edoxudine, efavirenz, emtricitabine, enfuvirtide, entecavir, fomvirsen, fosamprenavir, foscarnet, fosfonet, ganciclovir, gardasil, ibacitabine, imunovir, idoxuridine, imiquimod, indinavir, inosine, integrase inhibitors, interferons, including interferon type III, interferon type II, interferon type I, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, tenofovir, tenofovir disoproxil, tipranavir, trifluridine, trizivir, tromantadine, truvada, valganciclovir, vicriviroc, vidarabine, viramidine, zalcitabine, zanamivir, zidovudine, and combinations thereof.

Antifungal agents include amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, clioquinol, and combinations thereof.

Antiparasitic agents include amitraz, amoscanate, avermectin, carbadox, diethylcarbamizine, dimetridazole, diminazene, ivermectin, macrofilaricide, malathion, mitaban, oxamniquine, permethrin, praziquantel, prantel pamoate, selamectin, sodium stibogluconate, thiabendazole, and combinations thereof.

Antimicrobial agents that are not disclosed herein but which are useful for the amelioration or eradication of otic disorders are expressly included and intended within the scope of the embodiments presented.

Anti-Inflammatory Agents

Glucocorticoids or other anti-inflammatory steroids may be used with the formulations disclosed herein. Systemic glucocorticoid administration is the current therapy in use for autoimmune hearing loss. Typical treatment duration lasts for months and the side effects from systemic therapy can be substantial. In some of the early studies on AIED, prednisone combined with cyclophosphamide was an effective therapy. However, the risks associated with cyclophosphamide rendered it a drug of last resort especially in young individuals of child-bearing age. One advantage of the use of a formulation described herein is the greatly reduced systemic exposure to anti-inflammatory glucocorticoid steroids.

In one embodiment is the active pharmaceutical ingredient of the formulation described herein is prednisolone. In another embodiment the active pharmaceutical ingredient of the formulation described herein is dexamethasone. In an additional embodiment, the active pharmaceutical ingredient of the formulation described herein is beclomethasone. In a further embodiment, the active pharmaceutical ingredient of the formulation described herein is selected from 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, or combinations thereof.

Corticosteroids are thought to act by the induction of phospholipase $A_2$ inhibitory proteins, collectively called lipocortins. It is postulated that these proteins control the biosynthesis of potent mediators of inflammation such as prostaglandins and leukotrienes by inhibiting the release of their common precursor arachidonic acid. Arachidonic acid is released from membrane phospholipids by phospholipase $A_2$.

Prednisolone

Prednisolone is a corticosteroid drug with predominantly glucocorticoid and low mineralocorticoid activity. It has about 4-5 times the potency of endogenous cortisol. It is useful for the treatment of a wide range of inflammatory and auto-immune conditions such as asthma, rheumatoid arthritis, Ulcerative Colitis and Crohn's disease, multiple sclerosis, cluster headaches and Systemic Lupus Erythematosus. It can also be used as an immunosuppressive drug for organ transplants and in cases of adrenal insufficiency (Addison's).

Dexamethasone

Dexamethasone is a corticosteroid drug with glucocorticoid activity. It has about 25-30 times the potency of endogenous cortisol. It is used to treat many inflammatory and autoimmune conditions such as rheumatoid arthritis. In some embodiments, a composition or device described herein comprises dexamethasone. In some embodiments, a composition or device comprising dexamethasone is used Beclomethasone Beclomethasone dipropionate, also referred to as beclometasone, is a very potent glucocorticoid steroid drug. In the form of an inhaler, it is used for the prophylaxis of asthma. As a nasal spray, it is used for the treatment of rhinitis (e.g. hayfever) and sinusitis. In some instances it is used by oral pathologists in the treatment of unusually severe canker sores. As a cream or ointment it is used to treat severe inflammatory skin disorders (e.g. eczema) unresponsive to less potent steroids, but is generally avoided in the treatment of psoriasis due to the risk of rebound on withdrawal.

Budesonide

Budesonide is a potent glucocorticoid steroid 60-fold more potent than cortisol. It is indicated for the treatment of asthma (via oral inhaler), non-infectious rhinitis, including hay fever and other allergies (via nasal inhaler). Additionally, it is used for inflammatory bowel disease.

Clobetasol

Clobetasol is a very potent corticosteroid used in topical formulations. It has anti-inflammatory, antipruritic, vasoconstrictive, and immune-modulating properties. It is currently used in the treatment of a variety of hyperproliferative and/or inflammatory dermatoses, including psoriasis and atopic dermatitis.

Dexamethasone, beclomethasone and prednisolone have long-term efficacy with biological half-lifes of 36-72 hours.

In some embodiments, anti-inflammatory agents are anti-TNF agents, TNF-α converting enzyme inhibitors, IKK inhibitors, calcineurin inhibitors, toll-like receptor inhibitors, interleukin inhibitors, or the like. Anti-inflammatory agents that are not disclosed herein but which are useful for the amelioration or eradication of otic disorders are expressly included and intended within the scope of the embodiments presented.

RNAi

In some embodiments, where inhibition or down-regulation of a target is desired RNA interference may be utilized. In some embodiments, the agent that inhibits or down-regulates the target is an siRNA molecule. In certain embodiments, the siRNA molecule inhibits or down-regulates genes encoding one or more mediator of inflammation (e.g., cytokines, IKKs, TACEs, calcineurins, TLRs or the like). In certain instances, the siRNA molecule inhibits the transcription of a target by RNA interference (RNAi). In some embodiments, a double stranded RNA (dsRNA) molecule with sequences complementary to a target is generated (e.g. by PCR). In some embodiments, a 20-25 bp siRNA molecule with sequences complementary to a target is generated. In some embodiments, the 20-25 bp siRNA molecule has 2-5 bp overhangs on the 3' end of each strand, and a 5' phosphate terminus and a 3' hydroxyl terminus. In some embodiments, the 20-25 bp siRNA molecule has blunt ends. For techniques for generating RNA sequences see Molecular Cloning: A Laboratory Manual, second edition (Sambrook et al., 1989) and Molecular Cloning: A Laboratory Manual, third edition (Sambrook and Russel, 2001), jointly referred to herein as "Sambrook"); Current Protocols in Molecular Biology (F. M. Ausubel et al., eds., 1987, including supplements through 2001); Current Protocols in Nucleic Acid Chemistry John Wiley & Sons, Inc., New York, 2000) which are hereby incorporated by reference for such disclosure.

In some embodiments, the dsRNA or siRNA molecule is incorporated into a controlled-release auris-acceptable microsphere or microparticle, hydrogel, liposome, actinic radiation curable gel, solvent-release gel, xerogel, paint, foam, in situ forming spongy material, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, actinic radiation curable gel, solvent-release gel, hydrogel, liposome, or thermoreversible gel is injected through the round window membrane. In some embodiments, the auris-acceptable microsphere, hydrogel, liposome, paint, foam, in situ forming spongy material, actinic radiation curable gel, solvent-release gel, nanocapsule or nanosphere or thermoreversible gel is injected into the cochlea, the organ of Corti, the vestibular labyrinth, or a combination thereof.

In certain instances, after administration of the dsRNA or siRNA molecule, cells at the site of administration (e.g. the cells of cochlea, organ of Corti, and/or the vestibular labyrinth) are transformed with the dsRNA or siRNA molecule. In certain instances following transformation, the dsRNA molecule is cleaved into multiple fragments of about 20-25 bp to yield siRNA molecules. In certain instances, the fragments have about 2 bp overhangs on the 3' end of each strand.

In certain instances, an siRNA molecule is divided into two strands (the guide strand and the anti-guide strand) by an RNA-induced Silencing Complex (RISC). In certain instances, the guide strand is incorporated into the catalytic component of the RISC (i.e. argonaute). In certain instances, the guide strand binds to a complementary target mRNA sequence. In certain instances, the RISC cleaves the target mRNA. In certain instances, the expression of the target gene is down-regulated.

In some embodiments, a sequence complementary to a target is ligated into a vector. In some embodiments, the sequence is placed between two promoters. In some embodiments, the promoters are orientated in opposite directions. In some embodiments, the vector is contacted with a cell. In certain instances, a cell is transformed with the vector. In certain instances following transformation, sense and antisense strands of the sequence are generated. In certain instances, the sense and anti-sense strands hybridize to form a dsRNA molecule which is cleaved into siRNA molecules. In certain instances, the strands hybridize to form an siRNA molecule. In some embodiments, the vector is a plasmid (e.g pSUPER; pSUPER.neo; pSUPER.neo+gfp).

In some embodiments, the vector is incorporated into a controlled-release auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the cochlea, the organ of Corti, the vestibular labyrinth, or a combination thereof.

Antimicrobial Agents and Anti-Inflammatory Agents

Contemplated within the scope of the embodiments presented herein are compositions and devices that comprise an antimicrobial agent in combination with an anti-inflammatory agent. In specific embodiments, a composition or device described herein comprises an antibiotic (e.g., any antibiotic described herein) in combination with an anti-inflammatory agent (e.g., any anti-inflammatory agent described herein). In certain embodiments, a composition or device described herein comprises an antibiotic (e.g., any antibiotic described herein) in combination with a corticosteroid.

In some embodiments, a composition comprising an antimicrobial agent and an anti-inflammatory agent has different release profiles for each of the active agents. For example, in some embodiments, a composition comprising an antibiotic and a corticosteroid provides a sustained release of the antibiotic and an intermediate release of the corticosteroid. In some embodiments, a composition comprising an antibiotic and a corticosteroid provides a sustained release of the antibiotic and an immediate release of the corticosteroid. In some embodiments, a composition comprising an antibiotic and a corticosteroid provides an immediate release of the antibiotic and a sustained release of the corticosteroid. In some embodiments, a composition comprising an antibiotic and a corticosteroid provides an immediate release of the antibiotic and an intermediate release of the corticosteroid.

In other embodiments, a composition comprising an antimicrobial agent and an anti-inflammatory agent has similar release profiles for each of the active agents. For example, in some embodiments, a composition comprising an antibiotic and a corticosteroid provides immediate release of the antibiotic and corticosteroid. In some embodiments, a composition comprising an antibiotic and a corticosteroid provides intermediate release of the antibiotic and corticosteroid. In some embodiments, a composition comprising an antibiotic and a corticosteroid provides a sustained release of the antibiotic and corticosteroid.

In certain embodiments, a composition or device described herein comprises an antibiotic in combination with dexamethasone. In certain embodiments, a composition or device described herein comprises an antibiotic in combination with methylprednisolone or prednisolone. In certain embodiments, a composition or device described herein comprises ciprofloxacin in combination with dexamethasone. In certain embodiments, a composition or device described herein comprises ciprofloxacin in combination with methylprednisolone or prednisolone. In certain embodiments, a composition or device described herein comprises gentamicin in combination with dexamethasone. In certain embodiments, a composition or device described herein comprises gentamicin in combination with methylprednisolone or prednisolone.

In some embodiments, a composition comprising an antibiotic and a corticosteroid contains one or both active agents as micronized active agents. By way of example, in some embodiments, a composition comprising micronized dexamethasone and micronized ciprofloxacin provides extended release of dexamethasone over 3 days and extended release of ciprofloxacin over 10 days. By way of example, in some embodiments, a composition comprising micronized dexamethasone and micronized ciprofloxacin provides extended release of ciprofloxacin over 3 days and extended release of dexamethasone over 10 days.

In some embodiments, pharmaceutically active metabolites, salts, polymorphs, prodrugs, analogues, and derivatives of the antimicrobial agents or anti-inflammatory agents discussed above that retain the ability of the parent agents to treat otic disorders of the ear are also useful and compatible with the formulations disclosed herein.

Combination Therapy

In some embodiments, any composition or device described herein comprises one or more active agents and/or a second therapeutic agent including but not limited to anti-emetic agents, cytotoxic agents, anti-TNF agents, otoprotectants or the like.

Cytotoxic Agents

Any cytotoxic agent useful for the treatment of otic disorders is suitable for use in the formulations and methods disclosed herein. In certain embodiments, the cytotoxic agent is an antimetabolite, an antifolate, an alkylating agent and/or a DNA intercolator. In some embodiments, the cytotoxic agent is a protein, a peptide, an antibody, DNA, a carbohydrate, an inorganic molecule, or an organic molecule. In certain embodiments, the cytotoxic agents are cytotoxic small molecules. Typically, cytotoxic small molecules are of relatively low molecular weight, e.g., less than 1,000, or less than 600-700, or between 300-700 molecular weight. In some embodiments, the cytotoxic small molecules will also have anti-inflammatory properties.

In certain embodiments, the cytotoxic agent is methotrexate (RHEUMATREX®, Amethopterin), cyclophosphamide)(CYTOXAN®, or thalidomide)(THALIDOMID®. All of the compounds have anti-inflammatory properties and can be used in the formulations and compositions disclosed herein for the treatment of inflammatory disorders of the ear, including AIED In some embodiments, cytotoxic agents used in the compositions, formulations, and methods disclosed herein are metabolites, salts, polymorphs, prodrugs, analogues, and derivatives of cytotoxic agents, including methotrexate, cyclophosphamide, and thalidomide. Particularly preferred are metabolites, salts, polymorphs, prodrugs, analogues, and derivatives of cytotoxic agents, e.g., methotrexate, cyclophosphamide, and thalidomide, that retain at least partially the cytotoxicity and anti-inflammatory properties of the parent compounds. In certain embodiments, analogues of thalidomide used in the formulations and compositions disclosed herein are lenalidomide (REVLIMID) and CC-4047 (ACTIMID®).

Cyclophosphamide is a prodrug that undergoes in vivo metabolism when administered systemically. The oxidized metabolite 4-hydroxycyclophosphamide exists in equilibrium with aldophosphamide, and the two compounds serve as the transport forms of the active agent phosphoramide mustard and the degradation byproduct acrolein. Thus, in some embodiments, preferred cyclophosphamide metabolites for incorporation into the formulations and compositions disclosed herein are 4-hydroxycyclophosphamide, aldophosphamide, phosphoramide mustard, and combinations thereof.

Anti-TNF Agents

Contemplated for use in conjunction with the antimicrobial agent formulations disclosed herein are agents that reduce or ameliorate symptoms or effects resulting from an autoimmune disease and/or inflammatory disorder, including AIED or OM. Accordingly, some embodiments incorporate the use of agents which block the effects of TNF-α, including anti-TNF agents. By way of example only, anti-TNF agents include etanercept (ENBREL®), infliximab (REMICADE®), adalimumab (HUMIRA®), and golimumab (CNTO 148) or combinations thereof.

Infliximab and adalimumab are anti-TNF monoclonal antibodies, and etanercept is a fusion protein designed to bind specifically to the TNF protein. All are currently approved for use in the treatment of rheumatoid arthritis. Golimumab, which is currently in Phase 3 clinical trials for rheumatoid arthritis, psoriatic arthritis and ankylosing spondylitis, is a fully-humanized anti-TNF-α IgG1 monoclonal antibody that targets and neutralizes both the soluble and the membrane-bound form of TNF-α.

Other antagonists of TNF, by way of example only, include TNF receptors (pegylated soluble TNF receptor type 1; Amgen); TNF binding factors (Onercept; Serono); TNF antibodies (US Patent App. No. 2005/0123541; US Patent App. No. 2004/0185047); single domain antibodies against the p55 TNF receptor (US Patent App. No. 2008/00088713); soluble TNF receptors (US Patent App. No. 2007/0249538); fusion polypeptides binding to TNF (US Patent App. No. 2007/0128177); TNF-α converting enzyme inhibitors (Skotnicki et al., Annual Reports in Medicinal Chemistry (2003), 38, 153-162); IKK inhibitors (Karin et al., Nature Reviews Drug Discovery (2004), 3, 17-26) and flavone derivatives (US Patent App. No. 2006/0105967), all of which are incorporated by reference for such disclosure.

The use of Onercept, a soluble TNF p55 receptor, was discontinued in 2005. Three phase-III clinical trials reported patients diagnosed with fatal sepsis. A risk to benefit analysis was subsequently performed, resulting in the discontinuation of the clinical trials. As discussed above, the embodiments herein specifically encompass the use of anti-TNF agents that have been previously shown to have limited or no systemic release, systemic toxicity, poor PK characteristics of combinations thereof.

Anti-Emetic Agents/Central Nervous System Agents

Anti-emetic agents are optionally used in combination with the antimicrobial agent formulations disclosed herein. Anti-emetic agents include antihistamines and central nervous agents, including antipsychotic agents, barbiturates, benzodiazepines and phenothiazines. Other anti-emetic agents include the serotonin receptor antagonists, which include dolasetron, granisetron, ondansetron, tropisetron, palonosetron, and combinations thereof; dopamine antagonists, including domperidone, properidol, haloperidol, chlorpromazine, promethazine, prochlorperazine and combinations thereof cannabinoids, including dronabinol, nabilone, sativex, and combinations thereof anticholinergics, including scopolamine; and steroids, including dexamethasone; trimethobenzamine, emetrol, propofol, muscimol, and combinations thereof.

Optionally, central nervous system agents and barbiturates are useful in the treatment of nausea and vomiting, symptoms that often accompany otic disorders. When used, an appropriate barbiturate and/or central nervous system agent is selected to relieve or ameliorate specific symptoms without possible side effects, including ototoxicity. Moreover, as discussed above, targeting of the drugs to the round window membrane of the auris interna reduces possible side effects and toxicity caused by systemic administration of these drugs. Barbiturates, which act as a central nervous system depressant, include allobarbital, alphenal, amobarbital, aprobarbital, barnexaclone, barbital, brallobarbital, butabarbital, butalbital, butallylonal, butobarbital, corvalol, crotylbarbital, cyclobarbital, cyclopal, ethallobarbital, febarbamate, heptabarbital, hexethal, hexobarbital, metharbital, methohexital, methylphenobarbital, narcobarbital, nealbarbital, pentobarbital, phenobarbital, primidone, probarbital, propallylonal, proxibarbital, reposal, secobarbital, sigmodal, sodium thiopental, talbutal, thialbarbital, thiamylal, thiobarbital, thiobutabarbital, tuinal, valofane, vinbarbital, vinylbital, and combinations thereof.

Other central nervous system agents which are optionally used in conjunction with the antimicrobial agent formulations disclosed herein include benzodiazepines or phenothiazines. Useful benzodiazepines include, but are not limited to diazepam, lorazepam, oxazepam, prazepam, alprazolam, bromazepam, chlordiazepoxide, clonazepam, clorazepate, brotizolam, estazolam, flunitrazepam, flurazepam, loprazolam, lormetazepam, midazolam, nimetazepam, nitrazepam, ternazepam, triazolam, and combinations thereof. Examples of phenothiazines include prochlorperazine, chlorpromazine, promazine, triflupromazine, levopromazine, methotrimepramazine, mesoridazine, thiroridazine, fluphenazine, perphenazine, flupentixol, trifluoperazine, and combinations thereof.

Antihistamines, or histamine antagonists, act to inhibit the release or action of histamine. Antihistamines that target the H1 receptor are useful in the alleviation or reduction of nausea and vomiting symptoms that are associated with AIED, other autoimmune disorders, as well as anti-inflammatory disorders. Such antihistamines include, but are not limited to, meclizine, diphenhydramine, loratadine and quetiapine. Other antihistamines include mepyramine, piperoxan, antazoline, carbinoxamine, doxylamine, clemastine, dimenhydrinate, pheniramine, chlorphenamine, chlorpheniramine, dexchlorpheniramine, brompheniramine, triprolidine, cyclizine, chlorcyclizine, hydroxyzine, promethazine, alimemazine, trimeprazine, cyproheptadine, azatadine, ketotifen, oxatomide and combinations thereof.

Platelet Activating Factor Antagonists

Platelet activating factor antagonists are also contemplated for use in combination with the antimicrobial agent formulations disclosed herein. Platelet activating factor antagonists include, by way of example only, kadsurenone, phomactin G, ginsenosides, apafant (4-(2-chlorophenyl)-9- methyl-2[3(4-morpholinyl)-3-propanol-1-yl[6H-thieno[3.2-f[[1.2.4]triazolo]4,3-1]]1.4]diazepine), A-85783, BN-52063, BN-52021, BN-50730 (tetrahedra-4,7,8,10 methyl-1 (chloro-1 phenyl)-6 (methoxy-4 phenyl-carbamoyl)-9 pyrido [4',3'-4,5] thieno [3,2-f] triazolo-1,2,4 [4,3-a] diazepine-1,4), BN 50739, SM-12502, RP-55778, Ro 24-4736, SR27417A, CV-6209, WEB 2086, WEB 2170, 14-deoxyandrographolide, CL 184005, CV-3988, TCV-309, PMS-601, TCV-309 and combinations thereof.

Nitric Oxide Synthase Inhibitors

Nitric oxide synthase (NOS) inhibitors are also contemplated for use in combination with the antimicrobial agent formulations disclosed herein. NOS inhibitors include, by way of example only, aminoguanidine, 1-Amino-2-hydroxyguanidinep-Toluensulfate, guanidinoethyldisulfide (GED), Bromocriptine Mesylate, Dexamethasone, $N^G,N^G$-Dimethyl-L-arginine, Dihydrochloride, Diphenyleneiodonium Chloride, 2-Ethyl-2-thiopseudourea, haloperidol, L-$N^5$-(1-Iminoethyl)ornithine, MEG, S-Methylisothiourea Sulfate (SMT), S-Methyl-L-thiocitrulline, $N^G$-Monoethyl-L-arginine, $N^G$-Monomethyl-D-arginine, NG-Nitro-L-arginine Methyl Ester, L-NIL, $N^G$-Nitro-L-arginine (L-NNA), 7-Nitroindazole, nNOS Inhibitor I, 1,3-PBITU, L-Thiocitrulline, $N^G$-Propyl-L-arginine, SKF-525A, TRIM, $N^G$-nitro-L-arginine methyl ester (L-NAME), MTR-105, L-NMMA, BBS-2, ONO-1714 and combinations thereof.

Other Additional Active Agents

Other pharmaceutical agents that are optionally used in combination with the antimicrobial agent formulations disclosed herein for the treatment of otic disorders, include other agents that have been used to treat the same conditions, including corticosteroids; cytotoxic agents, treatment with collagen, gamma globulin, interferons, and/or copaxone; and combinations thereof. In addition, other pharmaceutical agents are optionally used to treat attendant symptoms of otic disorders disclosed herein, including AIED, otitis media, otitis externa, Meniere's disease, Ramsay Hunt syndrome, otosyphilis, and vestibular neuronitis, such as vomiting, dizziness and general malaise. The additional active agents can be formulated with the antimicrobial agents in the compositions and formulations disclosed herein, or they can be administered separately through alternative modes of delivery.

Concentration of Active Agent

In some embodiments, the compositions described herein have a concentration of active pharmaceutical ingredient between about 0.01% to about 90%, between about 0.01% to about 50%, between about 0.1% to about 70%, between about 0.1% to about 50%, between about 0.1% to about 40%, between about 0.1% to about 30%, between about 0.1% to about 20%, between about 0.1% to about 10%, or between about 0.1% to about 5%, of the active ingredient, or pharmaceutically acceptable prodrug or salt thereof, by weight of the composition. In some embodiments, the compositions described herein have a concentration of active pharmaceutical agent, or pharmaceutically acceptable prodrug or salt thereof, between about 1% to about 50%, between about 5% to about 50%, between about 10% to about 40%, or between about 10% to about 30%, of the active ingredient, or pharmaceutically acceptable prodrug or salt thereof, by weight of the composition. In some embodiments, formulations described herein comprise about 70% by weight of an antimicrobial agent, or pharmaceutically acceptable prodrug or salt thereof, by weight of the formulation. In some embodiments, formulations described herein comprise about 60% by weight of an antimicrobial agent, or pharmaceutically acceptable prodrug or salt thereof, by weight of the formulation. In some embodiments, formulations described herein comprise about 50% by weight of an antimicrobial agent, or pharmaceutically acceptable prodrug or salt thereof, by weight of the formulation. In some embodiments, formulations described herein comprise about 40% by weight of an antimicrobial agent, or pharmaceutically acceptable prodrug or salt thereof, by weight of the formulation. In some embodiments, formulations described herein comprise about 30% by weight, or pharmaceutically acceptable prodrug or salt thereof, of an antimicrobial agent by weight of the formulation. In some embodiments, formulations described herein comprise about 20% by weight of an antimicrobial agent, or pharmaceutically acceptable prodrug or salt thereof, by weight of the formulation. In some embodiments, formulations described herein comprise about 15% by weight of an antimicrobial agent, or pharmaceutically acceptable prodrug or salt thereof, by weight of the formulation. In some embodiments, formulations described herein comprise about 10% by weight of an antimicrobial agent by weight of the formulation. In some embodiments, formulations described herein comprise about 5% by weight of an antimicrobial agent, or pharmaceutically acceptable prodrug or salt thereof, by weight of the formulation. In some embodiments, formulations described herein comprise about 2.5% by weight of an antimicrobial agent, or pharmaceutically acceptable prodrug or salt thereof, by weight of the formulation. In some embodiments, formulations described herein comprise about 1% by weight of an antimicrobial agent, or pharmaceutically acceptable prodrug or salt thereof, by weight of the formulation. In some embodiments, formulations described herein comprise about 0.5% by weight of an antimicrobial agent, or pharmaceutically acceptable prodrug or salt thereof, by weight of the formulation. In some embodiments, formulations described herein comprise about 0.1% by weight of an antimicrobial agent, or pharmaceutically acceptable prodrug or salt thereof, by weight of the formulation. In some embodiments, formulations described herein comprise about 0.01% by weight of an antimicrobial agent, or pharmaceutically acceptable prodrug or salt thereof, by weight of the formulation. In some embodiments, the formulations described herein have a concentration of active pharmaceutical ingredient, or pharmaceutically acceptable prodrug or salt thereof, between about 0.1 to about 70 mg/mL, between about 0.5 mg/mL to about 70 mg/mL, between about 0.5 mg/mL to about 50 mg/mL, between about 0.5 mg/mL to about 20 mg/mL, between about 1 mg to about 70 mg/mL, between about 1 mg to about 50 mg/mL, between about 1 mg/mL and about 20 mg/mL, between about 1 mg/mL to about 10 mg/mL, or between about 1 mg/mL to about 5 mg/mL, of the active agent, or pharmaceutically acceptable prodrug or salt thereof, by volume of the formulation.

Otic Surgery and Implants

In some embodiments, the pharmaceutical formulations, compositions or devices described herein are used in combination with (e.g., implantation, short-term use, long-term use, or removal of) implants (e.g., cochlear implants). As used herein, implants include auris-interna or auris-media medical devices, examples of which include cochlear implants, hearing sparing devices, hearing-improvement devices, short electrodes, tympanostomy tubes, micro-prostheses or piston-like prostheses; needles; stem cell transplants; drug delivery devices; any cell-based therapeutic; or the like. In some instances, the implants are used in conjunction with a patient experiencing hearing loss. In some instances, the hearing loss is present at birth. In some instances, the hearing loss is associated with conditions such as AIED, bacterial meningitis or the like that lead to osteoneogenesis and/or nerve damage with rapid obliteration of cochlear structures and profound hearing loss.

In some instances, an implant is an immune cell or a stem cell transplant in the ear. In some instances, an implant is a small electronic device that has an external portion placed behind the ear, and a second portion that is surgically placed under the skin that helps provide a sense of sound to a person who is profoundly deaf or severely hard-of-hearing. By way of example, such cochlear medical device implants bypass damaged portions of the ear and directly stimulate the auditory nerve. In some instances cochlear implants are used in single sided deafness. In some instances cochlear implants are used for deafness in both ears.

In some embodiments, administration of an antimicrobial composition or device described herein in combination with an otic intervention (e.g., an intratympanic injection, a stapedectomy, a tympanostomy, a medical device implant or a cell-based transplant) delays or prevents collateral damage to auris structures, e.g., irritation, inflammation and/or infection, caused by the external otic intervention (e.g., installation of an external device and/or cells in the ear). In some embodiments, administration of an antimicrobial composition or device described herein in combination with an implant allows for a more effective restoration of hearing loss compared to an implant alone.

In some embodiments, administration of an antimicrobial composition or device described herein reduces damage to cochlear structures caused by underlying conditions (e.g., bacterial meningitis, autoimmune ear disease (AIED)) allowing for successful cochlear device implantation. In some embodiments, administration of a composition or device described herein, in conjunction with otic surgery, medical device implantation and/or cell transplantation, reduces or prevents cell damage and/or inflammation associated with otic surgery, medical device implantation and/or cell transplantation.

In some embodiments, administration of an antimicrobial composition or device described herein (e.g., a composition or device comprising a corticosteriod) in conjunction with a cochlear implant or stem cell transplant has a trophic effect (e.g., promotes healthy growth of cells and/or healing of tissue in the area of an implant or transplant). In some embodiments, a trophic effect is desirable during otic surgery or during intratympanic injection procedures. In some embodiments, a trophic effect is desirable after installation of a medical device or after a cell transplant. In some of such embodiments, the antimicrobial compositions or devices described herein are administered via direct cochlear injection, through a chochleostomy or via deposition on the round window. In some embodiments, a medical device is coated with a composition described herein prior to implantation in the ear.

In some embodiments, administration of an anti-inflammatory or immunosuppressant composition (e.g., a composition comprising an immunosuppresant such as a corticosteroid) reduces inflammation and/or infections associated with otic surgery, implantation of a medical device or a cell transplant. In some instances, perfusion of a surgical area with an antimicrobial formulation described herein and/or an anti-inflammatory formulation described herein reduces or eliminates post-surgical and/or post-implantation complications (e.g., inflammation, cell damage, infection, osteoneogenesis or the like). In some instances, perfusion of a surgical area with a formulation described herein reduces post-surgery or post-implantation recuperation time.

In one aspect, the formulations described herein, and modes of administration thereof, are applicable to methods of direct perfusion of the inner ear compartments. Thus, the formulations described herein are useful in combination with otic interventions. In some embodiments, an otic intervention is an implantation procedure (e.g., implantation of a hearing device in the cochlea). In some embodiments, an otic intervention is a surgical procedure including, by way of non-limiting examples, cochleostomy, labyrinthotomy, mastoidectomy, stapedectomy, stapedotomy, tympanostomy, endolymphatic sacculotomy or the like. In some embodiments, the inner ear compartments are perfused with a formulation described herein prior to otic intervention, during otic intervention, or after otic intervention, or a combination thereof.

In some embodiments, when perfusion is carried out in combination with otic intervention, the antimicrobial compositions are immediate release compositions (e.g., a composition comprising ciprofloxacin). In some of such embodiments, the immediate release formulations described herein are non-thickened compositions and are substantially free of extended release components (e.g., gelling components such as polyoxyethylene-polyoxypropylene copolymers). In some of such embodiments, the compositions contain less than 5% of the extended release components (e.g., gelling components such as polyoxyethylene-polyoxypropylene triblock copolymers) by weight of the formulation. In some of such embodiments, the compositions contain less than 2% of the extended release components (e.g., gelling components such as polyoxyethylene-polyoxypropylene triblock copolymers) by weight of the formulation. In some of such embodiments, the compositions contain less than 1% of the extended release components (e.g., gelling components such as polyoxyethylene-polyoxypropylene triblock copolymers) by weight of the formulation. In some of such embodiments, a composition described herein that is used for perfusion of a surgical area contains substantially no gelling component and is an immediate release composition.

In certain embodiments, a composition described herein is administered before an otic intervention (e.g., before implantation of a medical device or a cell-based therapeutic). In certain embodiments, a composition described herein is administered during an otic intervention (e.g., during implantation of a medical device or a cell-based therapeutic). In other embodiments, a composition described herein is administered after an otic intervention (e.g., after implantation of a medical device or a cell-based therapeutic). In some of such embodiments, a composition described herein that is administered after the otic intervention is an intermediate release or extended release composition (e.g., a composition comprising an antibiotic, a composition comprising an anti-inflammatory agent, a composition comprising a an antibiotic and an anti-inflammatory agent or the like) and contains gelling components as described herein. In some embodiments, an implant (e.g., a tympanostomy tube) is coated with a composition or device described herein prior to insertion in the ear.

Presented below (Table 1) are examples of active agents contemplated for use with the formulations and devices disclosed herein. One or more active agents are used in any of the formulations or devices described herein.

Active Agents (including pharmaceutically acceptable salts, prodrugs of these active agents) for use with the Formulations Disclosed Herein

TABLE 1

| Auris Condition | Therapeutic Agent |
| --- | --- |
| Benign Paroxysmal Positional Vertigo | Diphenhydramine |
| Benign Paroxysmal Positional Vertigo | Lorazepam |
| Benign Paroxysmal Positional Vertigo | Meclizine |
| Benign Paroxysmal Positional Vertigo | Oldansetron |
| Hearing Loss | Estrogen |
| Otitis Media | Ciprofloxacin |
| Vertigo | Gentamicin |
| Hearing Loss | Estrogen and progesterone (E + P) |
| Hearing Loss | Folic acid |
| Hearing Loss | Lactated Ringer's with 0.03% Ofloxacin |
| Hearing Loss | Methotrexate |
| Hearing Loss | N-acetyl cysteine |
| Meniere's Disease | Betahistine |
| Meniere's Disease | Sildenafil |
| Meniere's Disease | conivaptan |
| Middle Ear Effusion | Pneumonococcal vaccine |
| Otitis Externa | Diclofenac sodium; dexote |
| Otitis Externa, Acute | AL-15469A/AL-38905 |
| Otitis Media | Amoxicillin/clavulanate |
| Otitis Media | Dornase alfa |
| Otitis Media | Echinacea purpurea |
| Otitis Media | Faropenem medoxomil |
| Otitis Media | Levofloxacin |
| Otitis Media | PNCRM9 |
| Otitis Media | Pneumococcal vaccine |
| Otitis Media | Telithromycin |
| Otitis Media | Zmax |
| Otitis Media with Effusion | Lansoprazole |
| Otitis Media, Acute | AL-15469A; AL-38905 |
| Otitis Media, Acute | Amoxicillin |
| Otitis Media, Acute | Amoxicillin-clavulanate |
| Otitis Media, Acute | Azithromycin |
| Otitis Media, Acute | Azithromycin SR |
| Otitis Media, Acute | Cefdinir |
| Otitis Media, Acute | Hyland's earache drops |
| Otitis Media, Acute | Montelukast |
| Otitis Media, Acute | Pneumonococcal vaccine |
| Otitis Media, Acute with Typanostomy Tubes | AL-15469A/AL38905 |
| Otitis Media, Chronic | Sulfamethoxazole-trimethoprim |
| Otitis Media, Suppurative | Azithromycin |
| Otitis Media, Suppurative | Telithromycin |
| Otosclerosis | Acetylcysteine |
| Ototoxicity | Aspirin |
| Tinnitus | Acamprosate |
| Tinnitus | Gabapentin |
| Tinnitus | Modafinil |
| Tinnitus | Neramexane |
| Tinnitus | Neramexane mesylate |
| Tinnitus | Piribedil |
| Tinnitus | Vardenafil |
| Tinnitus | Vestipitant + Paroxetine |
| Tinnitus | Vestiplitant |
| Tinnitus | Zinc sulfate |

General Methods of Sterilization

Provided herein are otic compositions that ameliorate or lessen otic disorders described herein. Further provided herein are methods comprising the administration of said otic compositions. In some embodiments, the compositions or devices are sterilized. Included within the embodiments disclosed herein are means and processes for sterilization of a pharmaceutical composition or device disclosed herein for use in humans. The goal is to provide a safe pharmaceutical product, relatively free of infection causing micro-organisms. The U. S. Food and Drug Administration has provided regulatory guidance in the publication "Guidance for Industry: Sterile Drug Products Produced by Aseptic Processing" available at: http://www.fda.gov/cder/guidance/5882fnl.htm, which is incorporated herein by reference in its entirety.

As used herein, sterilization means a process used to destroy or remove microorganisms that are present in a product or packaging. Any suitable method available for sterilization of objects and compositions is used. Available methods for the inactivation of microorganisms include, but are not limited to, the application of extreme heat, lethal chemicals, or gamma radiation. In some embodiments is a process for the preparation of an otic therapeutic formulation comprising subjecting the formulation to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington: The Science and Practice of Pharmacy published by Lippincott, Williams & Wilkins, and is incorporated by reference with respect to this subject matter.

Sterilization by Heat

Many methods are available for sterilization by the application of extreme heat. One method is through the use of a saturated steam autoclave. In this method, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety and economy in the sterilization process.

Dry heat sterilization is a method which is used to kill microorganisms and perform depyrogenation at elevated temperatures. This process takes place in an apparatus suitable for heating HEPA-filtered microorganism-free air to temperatures of at least 130-180° C. for the sterilization process and to temperatures of at least 230-250° C. for the depyrogenation process. Water to reconstitute concentrated or powdered formulations is also sterilized by autoclave. In some embodiments, the formulations described herein comprise micronized antimicrobial agents (e.g., micronized ciprofloxacin powder) that are sterilized by dry heating, e.g., heating for about 7-11 hours at internal powder temperatures of 130-140° C., or for 1-2 hours at internal temperatures of 150-180° C.

Chemical Sterilization

Chemical sterilization methods are an alternative for products that do not withstand the extremes of heat sterilization. In this method, a variety of gases and vapors with germicidal properties, such as ethylene oxide, chlorine dioxide, formaldehyde or ozone are used as the anti-apoptotic agents. The germicidal activity of ethylene oxide, for example, arises from its ability to serve as a reactive alkylating agent. Thus, the sterilization process requires the ethylene oxide vapors to make direct contact with the product to be sterilized.

Radiation Sterilization

One advantage of radiation sterilization is the ability to sterilize many types of products without heat degradation or other damage. The radiation commonly employed is beta radiation or alternatively, gamma radiation from a $^{60}$Co source. The penetrating ability of gamma radiation allows its use in the sterilization of many product types, including solutions, compositions and heterogeneous mixtures. The germicidal effects of irradiation arise from the interaction of gamma radiation with biological macromolecules. This interaction generates charged species and free radicals. Subsequent chemical reactions, such as rearrangements and cross-linking processes, result in the loss of normal function for these biological macromolecules. The formulations described herein are also optionally sterilized using beta irradiation.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or polytetrafluoroethylene (PTFE) and have pore sizes ranging from 0.1 to 0.22 µm. Solutions of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3. Washington, D.C.: Health Industry Manufacturers Association, 1981) and involve challenging the membrane filter with a known quantity (ca. $10^7$/cm$^2$) of unusually small microorganisms, such as Brevundimonas diminuta (ATCC 19146).

Pharmaceutical compositions are optionally sterilized by passing through membrane filters. Formulations comprising nanoparticles (U.S. Pat. No. 6,139,870) or multilamellar vesicles (Richard et al., International Journal of Pharmaceutics (2006), 312(1-2):144-50) are amenable to sterilization by filtration through 0.22 µm filters without destroying their organized structure.

In some embodiments, the methods disclosed herein comprise sterilizing the formulation (or components thereof) by means of filtration sterilization. In another embodiment the auris-acceptable otic therapeutic agent formulation comprises a particle wherein the particle formulation is suitable for filtration sterilization. In a further embodiment said particle formulation comprises particles of less than 300 nm in size, of less than 200 nm in size, of less than 100 nm in size. In another embodiment the auris-acceptable formulation comprises a particle formulation wherein the sterility of the particle is ensured by sterile filtration of the precursor component solutions. In another embodiment the auris-acceptable formulation comprises a particle formulation wherein the sterility of the particle formulation is ensured by low temperature sterile filtration. In a further embodiment, low temperature sterile filtration is carried out at a temperature between 0 and 30° C., between 0 and 20° C., between 0 and 10° C., between 10 and 20° C., or between 20 and 30° C.

In another embodiment is a process for the preparation of an auris-acceptable particle formulation comprising: filtering the aqueous solution containing the particle formulation at low temperature through a sterilization filter; lyophilizing the sterile solution; and reconstituting the particle formulation with sterile water prior to administration. In some embodiments, a formulation described herein is manufactured as a suspension in a single vial formulation containing the micronized active pharmaceutical ingredient. A single vial formulation is prepared by aseptically mixing a sterile poloxamer solution with sterile micronized active ingredient (e.g., ciprofloxacin) and transferring the formulation to sterile pharmaceutical containers. In some embodiments, a single vial containing a formulation described herein as a suspension is resuspended before dispensing and/or administration.

In specific embodiments, filtration and/or filling procedures are carried out at about 5° C. below the gel temperature (Tgel) of a formulation described herein and with viscosity below a theoretical value of 100 cP to allow for filtration in a reasonable time using a peristaltic pump.

In another embodiment the auris-acceptable otic therapeutic agent formulation comprises a nanoparticle formulation wherein the nanoparticle formulation is suitable for filtration sterilization. In a further embodiment the nanoparticle formulation comprises nanoparticles of less than 300 nm in size, of less than 200 nm in size, or of less than 100 nm in size. In another embodiment the auris-acceptable formulation comprises a microsphere formulation wherein the sterility of the microsphere is ensured by sterile filtration of the precursor organic solution and aqueous solutions. In another embodiment the auris-acceptable formulation comprises a thermoreversible gel formulation wherein the sterility of the gel formulation is ensured by low temperature sterile filtration. In a further embodiment, the low temperature sterile filtration occurs at a temperature between 0 and 30° C., or between 0 and 20° C., or between 0 and 10° C., or between 10 and 20° C., or between 20 and 30° C. In another embodiment is a process for the preparation of an auris-acceptable thermoreversible gel formulation comprising: filtering the aqueous solution containing the thermoreversible gel components at low temperature through a sterilization filter; lyophilizing the sterile solution; and reconstituting the thermoreversible gel formulation with sterile water prior to administration.

In certain embodiments, the active ingredients are dissolved in a suitable vehicle (e.g. a buffer) and sterilized separately (e.g. by heat treatment, filtration, gamma radiation). In some instances, the active ingredients are sterilized separately in a dry state. In some instances, the active ingredients are sterilized as a suspension or as a colloidal suspension. The remaining excipients (e.g., fluid gel components present in auris formulations) are sterilized in a separate step by a suitable method (e.g. filtration and/or irradiation of a cooled mixture of excipients); the two solutions that are separately sterilized are then mixed aseptically to provide a final auris formulation. In some instances, the final aseptic mixing is performed just prior to administration of a formulation described herein.

In some instances, conventionally used methods of sterilization (e.g., heat treatment (e.g., in an autoclave), gamma irradiation, filtration) lead to irreversible degradation of polymeric components (e.g., thermosetting, gelling or mucoadhesive polymer components) and/or the active agent in the formulation. In some instances, sterilization of an auris formulation by filtration through membranes (e.g., 0.2 µM membranes) is not possible if the formulation comprises thixotropic polymers that gel during the process of filtration.

Accordingly, provided herein are methods for sterilization of auris formulations that prevent degradation of polymeric components (e.g., thermosetting and/or gelling and/or mucoadhesive polymer components) and/or the active agent during the process of sterilization. In some embodiments, degradation of the active agent (e.g., any therapeutic otic agent described herein) is reduced or eliminated through the use of specific pH ranges for buffer components and specific proportions of gelling agents in the formulations. In some embodiments, the choice of an appropriate gelling agent and/or thermosetting polymer allows for sterilization of formulations described herein by filtration. In some embodiments, the use of an appropriate thermosetting polymer and an appropriate copolymer (e.g., a gelling agent) in combination with a specific pH range for the formulation allows for high temperature sterilization of formulations described with substantially no degradation of the therapeutic agent or the polymeric excipients. An advantage of the methods of sterilization provided herein is that, in certain instances, the formulations are subjected to terminal sterilization via autoclaving without any loss of the active agent and/or excipients and/or polymeric components during the sterilization step and are rendered substantially free of microbes and/or pyrogens.

Microorganisms

Provided herein are auris-acceptable compositions or devices that ameliorate or lessen otic disorders described herein. Further provided herein are methods comprising the administration of said otic compositions. In some embodiments, the compositions or devices are substantially free of microorganisms. Acceptable bioburden or sterility levels are based on applicable standards that define therapeutically acceptable compositions, including but not limited to United States Pharmacopeia Chapters <1111> et seq. For example, acceptable sterility (e.g., bioburden) levels include about 10 colony forming units (cfu) per gram of formulation, about 50 cfu per gram of formulation, about 100 cfu per gram of formulation, about 500 cfu per gram of formulation or about 1000 cfu per gram of formulation. In some embodiments, acceptable bioburden levels or sterility for formulations include less than 10 cfu/mL, less that 50 cfu/mL, less than 500 cfu/mL or less than 1000 cfu/mL microbial agents. In addition, acceptable bioburden levels or sterility include the exclusion of specified objectionable microbiological agents. By way of example, specified objectionable microbiological agents include but are not limited to *Escherichia coli* (*E. coli*), *Salmonella* sp., *Pseudomonas aeruginosa* (*P. aeruginosa*) and/or other specific microbial agents.

Sterility of the auris-acceptable otic therapeutic agent formulation is confirmed through a sterility assurance program in accordance with United States Pharmacopeia Chapters <61>, <62> and <71>. A key component of the sterility assurance quality control, quality assurance and validation process is the method of sterility testing. Sterility testing, by way of example only, is performed by two methods. The first is direct inoculation wherein a sample of the composition to be tested is added to growth medium and incubated for a period of time up to 21 days. Turbidity of the growth medium indicates contamination. Drawbacks to this method include the small sampling size of bulk materials which reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the entire bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

Testing for *E. coli* and *Salmonella* includes the use of lactose broths incubated at 30-35° C. for 24-72 hours, incubation in MacConkey and/or EMB agars for 18-24 hours, and/or the use of Rappaport medium. Testing for the detection of *P. aeruginosa* includes the use of NAC agar. United States Pharmacopeia Chapter <62> further enumerates testing procedures for specified objectionable microorganisms.

In certain embodiments, any controlled release formulation described herein has less than about 60 colony forming units (CFU), less than about 50 colony forming units, less than about 40 colony forming units, or less than about 30 colony forming units of microbial agents per gram of formulation. In certain embodiments, the otic formulations described herein are formulated to be isotonic with the endolymph and/or the perilymph.

Endotoxins

Provided herein are otic compositions that ameliorate or lessen otic disorders described herein. Further provided herein are methods comprising the administration of said otic compositions. In some embodiments, the compositions or devices are substantially free of endotoxins. An additional aspect of the sterilization process is the removal of by-products from the killing of microorganisms (hereinafter, "Product"). The process of depyrogenation removes pyrogens from the sample. Pyrogens are endotoxins or exotoxins which induce an immune response. An example of an endotoxin is the lipopolysaccharide (LPS) molecule found in the cell wall of gram-negative bacteria. While sterilization procedures such as autoclaving or treatment with ethylene oxide kill the bacteria, the LPS residue induces a proinflammatory immune response, such as septic shock. Because the molecular size of endotoxins can vary widely, the presence of endotoxins is expressed in "endotoxin units" (EU). One EU is equivalent to 100 picograms of *E. coli* LPS. Humans can develop a response to as little as 5 EU/kg of body weight. The bioburden (e.g., microbial limit) and/or sterility (e.g., endotoxin level) is expressed in any units as recognized in the art. In certain embodiments, otic compositions described herein contain lower endotoxin levels (e.g. <4 EU/kg of body weight of a subject) when compared to conventionally acceptable endotoxin levels (e.g., 5 EU/kg of body weight of a subject). In some embodiments, the auris-acceptable otic therapeutic agent formulation has less than about 5 EU/kg of body weight of a subject. In other embodiments, the auris-acceptable otic therapeutic agent formulation has less than about 4 EU/kg of body weight of a subject. In additional embodiments, the auris-acceptable otic therapeutic agent formulation has less than about 3 EU/kg of body weight of a subject. In additional embodiments, the auris-acceptable otic therapeutic agent formulation has less than about 2 EU/kg of body weight of a subject.

In some embodiments, the auris-acceptable otic therapeutic agent formulation or device has less than about 5 EU/kg of formulation. In other embodiments, the auris-acceptable otic therapeutic agent formulation has less than about 4 EU/kg of formulation. In additional embodiments, the auris-acceptable otic therapeutic agent formulation has less than about 3 EU/kg of formulation. In some embodiments, the auris-acceptable otic therapeutic agent formulation has less than about 5 EU/kg Product. In other embodiments, the auris-acceptable otic therapeutic agent formulation has less than about 1 EU/kg Product. In additional embodiments, the auris-acceptable otic therapeutic agent formulation has less than about 0.2 EU/kg Product. In some embodiments, the auris-acceptable otic therapeutic agent formulation has less than about 5 EU/g of unit or Product. In other embodiments, the auris-acceptable otic therapeutic agent formulation has less than about 4 EU/g of unit or Product. In additional embodiments, the auris-acceptable otic therapeutic agent formulation has less than about 3 EU/g of unit or Product. In some embodiments, the auris-acceptable otic therapeutic agent formulation has less than about 5 EU/mg of unit or Product. In other embodiments, the auris-acceptable otic therapeutic agent formulation has less than about 4 EU/mg of unit or Product. In additional embodiments, the auris-acceptable otic therapeutic agent formulation has less than about 3 EU/mg of unit or Product. In certain embodiments, otic compositions described herein contain from about 1 to about 5 EU/mL of formulation. In certain embodiments, otic compositions described herein contain from about 2 to about 5 EU/mL of formulation, from about 3 to about 5 EU/mL of formulation, or from about 4 to about 5 EU/mL of formulation.

In certain embodiments, otic compositions or devices described herein contain lower endotoxin levels (e.g. <0.5 EU/mL of formulation) when compared to conventionally acceptable endotoxin levels (e.g., 0.5 EU/mL of formulation). In some embodiments, the auris-acceptable otic therapeutic agent formulation or device has less than about 0.5 EU/mL of formulation. In other embodiments, the auris-acceptable otic therapeutic agent formulation has less than about 0.4 EU/mL of formulation. In additional embodiments, the auris-acceptable otic therapeutic agent formulation has less than about 0.2 EU/mL of formulation.

Pyrogen detection, by way of example only, is performed by several methods. Suitable tests for sterility include tests described in United States Pharmacopoeia (USP)<71> Sterility Tests (23rd edition, 1995). The rabbit pyrogen test and the Limulus amebocyte lysate test are both specified in the United States Pharmacopeia Chapters <85> and <151> (USP23/NF 18, Biological Tests, The United States Pharmacopeial Convention, Rockville, Md., 1995). Alternative pyrogen assays have been developed based upon the monocyte activation-cytokine assay. Uniform cell lines suitable for quality control applications have been developed and have demonstrated the ability to detect pyrogenicity in samples that have passed the rabbit pyrogen test and the Limulus amebocyte lysate test (Taktak et al, J. Pharm. Pharmacol. (1990), 43:578-82). In an additional embodiment, the auris-acceptable otic therapeutic agent formulation is subject to depyrogenation. In a further embodiment, the process for the manufacture of the auris-acceptable otic therapeutic agent formulation comprises testing the formulation for pyrogenicity. In certain embodiments, the formulations described herein are substantially free of pyrogens.

pH and Practical Osmolarity

In some embodiments, an otic composition or device disclosed herein is formulated to provide an ionic balance that is compatible with inner ear fluids (e.g., endolymph and/or perilymph).

In certain instances, the ionic composition of the endolymph and perilymph regulate the electrochemical impulses of hair cells and thus hearing. In certain instances, changes in the conduction of electrochemical impulses along otic hair cells results in hearing loss. In certain instances, changes in the ionic balance of the endolymph or perilymph results in complete hearing loss. In certain instances, changes in the ionic balance of the endolymph or perilymph results in partial hearing loss. In certain instances, changes in the ionic balance of the endolymph or perilymph results in permanent hearing loss. In certain instances, changes in the ionic balance of the endolymph or perilymph results in temporary hearing loss.

In some embodiments, a composition or device disclosed herein is formulated in order to not disrupt the ionic balance of the endolymph. In some embodiments, a composition or device disclosed herein has an ionic balance that is the same as or substantially the same as the endolymph. In some embodiments, a composition or device disclosed herein does not does not disrupt the ionic balance of the endolymph so as to result in parital or complete hearing loss. In some embodiments, a composition or device disclosed herein does not does not disrupt the ionic balance of the endolymph so as to result in temporary or permanent hearing loss.

In some embodiments, a composition or device disclosed herein does not substantially disrupt the ionic balance of the perilymph. In some embodiments, a composition or device disclosed herein has an ionic balance that is the same as or substantially the same as the perilymph. In some embodiments, a composition or device disclosed herein does not result in parital or complete hearing loss as the composition or device does not disrupt the ionic balance of the perilymph. In some embodiments, a composition or device disclosed herein does not result in temporary or permanent hearing loss as the composition or device does not disrupt the ionic balance of the perilymph.

As used herein, "practical osmolarity/osmolality" or "deliverable osmolarity/osmolality" means the osmolarity/osmolality of a composition or device as determined by measuring the osmolarity/osmolality of the active agent and all excipients except the gelling and/or the thickening agent (e.g., polyoxyethylene-polyooxypropylene copolymers, carboxymethylcellulose or the like). The practical osmolarity of a composition or device disclosed herein is measured by a suitable method, e.g., a freezing point depression method as described in Viegas et. al., Int. J. Pharm., 1998, 160, 157-162. In some instances, the practical osmolarity of a composition or device disclosed herein is measured by vapor pressure osmometry (e.g., vapor pressure depression method) that allows for determination of the osmolarity of a composition or device at higher temperatures. In some instances, vapor pressure depression method allows for determination of the osmolarity of a composition or device comprising a gelling agent (e.g., a thermoreversible polymer) at a higher temperature wherein the gelling agent is in the form of a gel.

In some embodiments, the osmolarity at a target site of action (e.g., the perilymph) is about the same as the delivered osmolarity (i.e., osmolarity of materials that cross or penetrate the round window membrane) of a composition or device described herein. In some embodiments, a composition or device described herein has a deliverable osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L.

The practical osmolality of an otic composition or device disclosed herein is from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, a composition or device described herein has a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L.

The main cation present in the endolymph is potassium. In addition the endolymph has a high concentration of positively charged amino acids. The main cation present in the perilymph is sodium. In certain instances, the ionic composition of the endolymph and perilymph regulate the electrochemical impulses of hair cells. In certain instances, any change in the ionic balance of the endolymph or perilymph results in a loss of hearing due to changes in the conduction of electrochemical impulses along otic hair cells. In some embodiments, a composition disclosed herein does not disrupt the ionic balance of the perilymph. In some embodiments, a composition disclosed herein has an ionic balance that is the same as or substantially the same as the perilymph. In some embodiments, a composition disclosed herein does not disrupt the ionic balance of the endolymph. In some embodiments, a composition disclosed herein has an ionic balance that is the same as or substantially the same as the endolymph. In some embodiments, an otic formulation described herein is formulated to provide an ionic balance that is compatible with inner ear fluids (e.g., endolymph and/or perilymph).

The endolymph and the perilymph have a pH that is close to the physiological pH of blood. The endolymph has a pH range of about 7.2-7.9; the perilymph has a pH range of about 7.2-7.4. The in situ pH of the proximal endolymph is about 7.4 while the pH of distal endolymph is about 7.9.

In some embodiments, the pH of a composition described herein is adjusted (e.g., by use of a buffer) to an endolymph-compatible pH range of about 5.5 to 9.0. In specific embodiments, the pH of a composition described herein is adjusted to a perilymph-suitable pH range of about 5.5 to about 9.0. In some embodiments, the pH of a composition described herein is adjusted to a perilymph-suitable range of about 5.5 to about 8.0, about 6 to about 8.0 or about 6.6 to about 8.0. In some embodiments, the pH of a composition described herein is adjusted to a perilymph-suitable pH range of about 7.0-7.6.

In some embodiments, useful formulations also include one or more pH adjusting agents or buffering agents. Suitable pH adjusting agents or buffers include, but are not limited to acetate, bicarbonate, ammonium chloride, citrate, phosphate, pharmaceutically acceptable salts thereof and combinations or mixtures thereof.

In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the body's natural buffering system.

In one embodiment, diluents are also used to stabilize compounds because they can provide a more stable environment. Salts dissolved in buffered solutions (which also can provide pH control or maintenance) are utilized as diluents in the art, including, but not limited to a phosphate buffered saline solution.

In some embodiments, any gel formulation described herein has a pH that allows for sterilization (e.g, by filtration or aseptic mixing or heat treatment and/or autoclaving (e.g., terminal sterilization) of a gel formulation without degradation of the pharmaceutical agent (e.g., antimicrobial agent) or the polymers comprising the gel. In order to reduce hydrolysis and/or degradation of the otic agent and/or the gel polymer during sterilization, the buffer pH is designed to maintain pH of the formulation in the 7-8 range during the process of sterilization (e.g., high temperature autoclaving).

In specific embodiments, any gel formulation described herein has a pH that allows for terminal sterilization (e.g., by heat treatment and/or autoclaving) of a gel formulation without degradation of the pharmaceutical agent (e.g., antimicrobial agent) or the polymers comprising the gel. For example, in order to reduce hydrolysis and/or degradation of the otic agent and/or the gel polymer during autoclaving, the buffer pH is designed to maintain pH of the formulation in the 7-8 range at elevated temperatures. Any appropriate buffer is used depending on the otic agent used in the formulation. In some instances, since $pK_a$ of TRIS decreases as temperature increases at approximately −0.03/° C. and $pK_a$ of PBS increases as temperature increases at approximately 0.003/° C., autoclaving at 250° F. (121° C.) results in a significant downward pH shift (i.e. more acidic) in the TRIS buffer whereas a relatively much less upward pH shift in the PBS buffer and therefore much increased hydrolysis and/or degradation of an otic agent in TRIS than in PBS. Degradation of an otic agent is reduced by the use of an appropriate combination of a buffer and polymeric additives (e.g. CMC) as described herein.

In some embodiments, a formulation pH of between about 5.0 and about 9.0, between about 5.5 and about 8.5, between about 6.0 and about 7.6, between about 7 and about 7.8, between about 7.0 and about 7.6, between about 7.2 and 7.6, or between about 7.2 and about 7.4 is suitable for sterilization (e.g, by filtration or aseptic mixing or heat treatment and/or autoclaving (e.g., terminal sterilization)) of auris formulations described herein. In specific embodiments a formulation pH of about 6.0, about 6.5, about 7.0, about 7.1, about 7.2, about 7.3, about 7.4, about 7.5, or about 7.6 is suitable for sterilization (e.g, by filtration or aseptic mixing or heat treatment and/or autoclaving (e.g., terminal sterilization)) of any composition described herein.

In some embodiments, the formulations have a pH as described herein, and include a thickening agent (e.g, a viscosity enhancing agent) such as, by way of non-limiting example, a cellulose based thickening agent described herein. In some instances, the addition of a secondary polymer (e.g., a thickening agent) and a pH of formulation as described herein, allows for sterilization of a formulation described herein without any substantial degradation of the otic agent and/or the polymer components in the otic formulation. In some embodiments, the ratio of a thermoreversible poloxamer to a thickening agent in a formulation that has a pH as described herein, is about 40:1, about 35:1, about 30:1, about 25:1, about 20:1, about 15:1 about 10:1, or about 5:1. For example, in certain embodiments, a sustained and/or extended release formulation described herein comprises a combination of poloxamer 407 (pluronic F127) and carboxymethylcellulose (CMC) in a ratio of about 40:1, about 35:1, about 30:1, about 25:1, about 20:1, about 15:1, about 10:1 or about 5:1.

In some embodiments, the amount of thermoreversible polymer in any formulation described herein is about 10%, about 15%, about 20%, about 25%, about 30%, about 35% or about 40% of the total weight of the formulation. In some embodiments, the amount of thermoreversible polymer in any formulation described herein is about 10%, about 11%, about 12%, about 13%, about 14%, about 15%, about 16%, about 17%, about 18%, about 19%, about 20%, about 21%, about 22%, about 23%, about 24% or about 25% of the total weight of the formulation. In some embodiments, the amount of thermoreversible polymer (e.g., pluronic F127) in any formulation described herein is about 7.5% of the total weight of the formulation. In some embodiments, the amount of thermoreversible polymer (e.g., pluronic F127) in any formulation described herein is about 10% of the total weight of the formulation. In some embodiments, the amount of thermoreversible polymer (e.g., pluronic F127) in any formulation described herein is about 11% of the total weight of the formulation. In some embodiments, the amount of thermoreversible polymer (e.g., pluronic F127) in any formulation described herein is about 12% of the total weight of the formulation. In some embodiments, the amount of thermoreversible polymer (e.g., pluronic F127) in any formulation described herein is about 13% of the total weight of the formulation. In some embodiments, the amount of thermoreversible polymer (e.g., pluronic F127) in any formulation described herein is about 14% of the total weight of the formulation. In some embodiments, the amount of thermoreversible polymer (e.g., pluronic F127) in any formulation described herein is about 15% of the total weight of the formulation. In some embodiments, the amount of thermoreversible polymer (e.g., pluronic F127) in any formulation described herein is about 16% of the total weight of the formulation. In some embodiments, the amount of thermoreversible polymer (e.g., pluronic F127) in any formulation described herein is about 17% of the total weight of the formulation. In some embodiments, the amount of thermoreversible polymer (e.g., pluronic F127) in any formulation described herein is about 18% of the total weight of the formulation. In some embodiments, the amount of thermoreversible polymer (e.g., pluronic F127) in any formulation described herein is about 19% of the total weight of the formulation. In some embodiments, the amount of thermoreversible polymer (e.g., pluronic F127) in any formulation described herein is about 20% of the total weight of the formulation. In some embodiments, the amount of thermoreversible polymer (e.g., pluronic F127) in any formulation described herein is about 21% of the total weight of the formulation. In some embodiments, the amount of thermoreversible polymer (e.g., pluronic F127) in any formulation described herein is about 23% of the total weight of the formulation. In some embodiments, the amount of thermoreversible polymer (e.g., pluronic F127) in any formulation described herein is about 25% of the total weight of the formulation. In some embodiments, the amount of thickening agent (e.g., a gelling agent) in any formulation described herein is about 1%, about 5%, about 10%, or about 15% of the total weight of the formulation. In some embodiments, the amount of thickening agent (e.g., a gelling agent) in any formulation described herein is about 0.5%, about 1%, about 1.5%, about 2%, about 2.5%, about 3%, about 3.5%, about 4%, about 4.5%, or about 5% of the total weight of the formulation.

In some embodiments, the pharmaceutical formulations described herein are stable with respect to pH over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations described herein are stable with respect to pH over a period of at least about 1 week. Also described herein are formulations that are stable with respect to pH over a period of at least about 1 month.

Tonicity Agents

In general, the endolymph has a higher osmolality than the perilymph. For example, the endolymph has an osmolality of about 304 mOsm/kg $H_2O$ while the perilymph has an osmolality of about 294 mOsm/kg $H_2O$. In certain embodiments, tonicity agents are added to the formulations described herein in an amount as to provide a practical osmolality of an otic formulation of about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 350 mOsm/kg or from about 280 mOsm/kg to about 320 mOsm/kg. In some embodiments, the formulations described herein have a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 280 mOsm/L to about 320 mOsm/L or about 250 mOsm/L to about 320 mOsm/L.

In some embodiments, the deliverable osmolarity of any formulation described herein is designed to be isotonic with the targeted otic structure (e.g., endolymph, perilymph or the like). In specific embodiments, auris compositions described herein are formulated to provide a delivered perilymph-suitable osmolarity at the target site of action of about 250 to about 320 mOsm/L; and preferably about 270 to about 320 mOsm/L. In specific embodiments, auris compositions described herein are formulated to provide a delivered perilymph-suitable osmolality at the target site of action of about 250 to about 320 mOsm/kg $H_2O$; or an osmolality of about 270 to about 320 mOsm/kg $H_2O$. In specific embodiments, the deliverable osmolarity/osmolality of the formulations (i.e., the osmolarity/osmolality of the formulation in the absence of gelling or thickening agents (e.g., thermoreversible gel polymers) is adjusted, for example, by the use of appropriate salt concentrations (e.g., concentration of potassium or sodium salts) or the use of tonicity agents which renders the formulations endolymph-compatible and/or perilymph-compatible (i.e. isotonic with the endolymph and/or perilymph) upon delivery at the target site. The osmolarity of a formulation comprising a thermoreversible gel polymer is an unreliable measure due to the association of varying amounts of water with the monomeric units of the polymer. The practical osmolarity of a formulation (i.e., osmolarity in the absence of a gelling or thickening agent (e.g. a thermoreversible gel polymer) is a reliable measure and is measured by any suitable method (e.g., freezing point depression method, vapor depression method). In some instances, the formulations described herein provide a deliverable osmolarity (e.g., at a target site (e.g., perilymph) that causes minimal disturbance to the environment of the inner ear and causes minimum discomfort (e.g., vertigo and/or nausea) to a mammal upon administration.

In some embodiments, any formulation described herein is isotonic with the perilymph and/or endolymph. Isotonic formulations are provided by the addition of a tonicity agent. Suitable tonicity agents include, but are not limited to any pharmaceutically acceptable sugar, salt or any combinations or mixtures thereof, such as, but not limited to dextrose, glycerin, mannitol, sorbitol, sodium chloride, and other electrolytes. In some embodiments, tonicity agents are non-ototoxic.

Useful auris compositions include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the formulations described herein have a pH and/or practical osmolarity as described herein, and have a concentration of active pharmaceutical ingredient between about 1 µM and about 10 µM, between about 1 mM and about 100 mM, between about 0.1 mM and about 100 mM, between about 0.1 mM and about 100 nM. In some embodiments, the formulations described herein have a pH and/or practical osmolarity as described herein, and have a concentration of active pharmaceutical ingredient between about 0.01%-about 20%, between about 0.01%-about 10%, between about 0.01%-about 7.5%, between about 0.01%-6%, between about 0.01-5%, between about 0.1-about 10%, or between about 0.1-about 6% of the active ingredient by weight of the formulation. In some embodiments, the formulations described herein have a pH and/or practical osmolarity as described herein, and have a concentration of active pharmaceutical ingredient between about 0.1 and about 70 mg, between about 1 mg and about 70 mg/mL, between about 1 mg and about 50 mg/mL, between about 1 mg/mL and about 20 mg/mL, between about 1 mg/mL to about 10 mg/mL, between about 1 mg/mL to about 5 mg/mL, or between about 0.5 mg/mL to about 5 mg/mL of the active agent by volume of the formulation. In some embodiments, the formulations described herein have a pH and/or practical osmolarity as described herein, and have a concentration of active pharmaceutical ingredient between about 1 µg/mL and about 500 µg/mL, between about 1 µg/mL and about 250 µg/mL, between about 1 µg and about 100 µg/mL, between about 1 µg/mL and about 50 µg/mL, or between about 1 µg/mL and about 20 µg/mL of the active agent by volume of the formulation.

Particle Size

Size reduction is used to increase surface area and/or modulate formulation dissolution properties. It is also used to maintain a consistent average particle size distribution (PSD) (e.g., micrometer-sized particles, nanometer-sized particles or the like) for any formulation described herein. In some embodiments, any formulation described herein comprises multiparticulates, i.e., a plurality of particle sizes (e.g., micronized particles, nano-sized particles, non-sized particles, colloidal particles); i.e, the formulation is a multiparticulate formulation. In some embodiments, any formulation described herein comprises one or more multiparticulate (e.g., micronized) therapeutic agents. Micronization is a process of reducing the average diameter of particles of a solid material. Micronized particles are from about micrometer-sized in diameter to about nanometer-sized in diameter. In some embodiments, the average diameter of particles in a micronized solid is from about 0.5 µm to about 500 µm. In some embodiments, the average diameter of particles in a micronized solid is from about 1 µm to about 200 µm. In some embodiments, the average diameter of particles in a micronized solid is from about 2 µm to about 100 µm. In some embodiments, the average diameter of particles in a micronized solid is from about 3 µm to about 50 µm. In some embodiments, a particulate micronized solid comprises particle sizes of less than about 5 microns, less than about 20 microns and/or less than about 100 microns. In some embodiments, the use of particulates (e.g., micronized particles) of antimicrobial agent allows for extended and/or sustained release of the antimicrobial agent from any formulation described herein compared to a formulation comprising non-multiparticulate (e.g., non-micronized) antimicrobial agent. In some instances, formulations containing multiparticulate (e.g. micronized) antimicrobial agent are ejected from a 1 mL syringe adapted with a 27G needle without any plugging or clogging.

In some instances, any particle in any formulation described herein is a coated particle (e.g., a coated micronized particle, nano-particle) and/or a microsphere and/or a liposomal particle. Particle size reduction techniques include, by way of example, grinding, milling (e.g., air-attrition milling (jet milling), ball milling), coacervation, complex coacervation, high pressure homogenization, spray drying and/or supercritical fluid crystallization. In some instances, particles are sized by mechanical impact (e.g., by hammer mills, ball mill and/or pin mills). In some instances, particles are sized via fluid energy (e.g., by spiral jet mills, loop jet mills, and/or fluidized bed jet mills). In some embodiments formulations described herein comprise crystalline particles and/or isotropic particles. In some embodiments, formulations described herein comprise amorphous particles and/or anisotropic particles. In some embodiments, formulations described herein comprise therapeutic agent particles wherein the therapeutic agent is a free base, or a salt, or a prodrug of a therapeutic agent, or any combination thereof.

In some embodiments, a formulation described herein comprises one or more antimicrobial agents wherein the antimicrobial agent comprises nanoparticulates. In some embodiments, a formulation described herein comprises antimicrobial agent beads (e.g., vancomycin beads) that are optionally coated with controlled release excipients. In some embodiments, a formulation described herein comprises an antimicrobial agent that is granulated and/or reduced in size and coated with controlled release excipients; the granulated coated antimicrobial agent particulates are then optionally micronized and/or formulated in any of the compositions described herein.

In some instances, a combination of an antimicrobial agent as a neutral molecule, free acid or free base and/or a salt of the antimicrobial agent is used to prepare pulsed release otic agent formulations using the procedures described herein. In some formulations, a combination of a micronized antimicrobial agent (and/or salt or prodrug thereof) and coated particles (e.g., nanoparticles, liposomes, microspheres) is used to prepare pulsed release otic agent formulations using any procedure described herein. Alternatively, a pulsed release profile is achieved by solubilizing up to 20% of the delivered dose of the antimicrobial agent (e.g., micronized antimicrobial agent, free base, free acid or salt or prodrug thereof; multiparticulate antimicrobial agent, free base, free acid or salt or prodrug thereof) with the aid of cyclodextrins, surfactants (e.g., poloxamers (407, 338, 188), tween (80, 60, 20, 81), PEG-hydrogenated castor oil, cosolvents like N-methyl-2-Pyrrolidone or the like and preparing pulsed release formulations using any procedure described herein.

In specific embodiments, any auris-compatible formulation described herein comprises one or more micronized pharmaceutical agents (e.g., antimicrobial agents). In some of such embodiments, a micronized pharmaceutical agent comprises micronized particles, coated (e.g., with an extended release coat) micronized particles, or a combination thereof. In some of such embodiments, a micronized pharmaceutical agent comprising micronized particles, coated micronized particles, or a combination thereof, comprises an antimicrobial agent as a neutral molecule, a free acid, a free base, a salt, a prodrug or any combination thereof. In certain embodiments, a pharmaceutical composition described herein comprises an antimicrobial agent as a micronized powder. In certain embodiments, a pharmaceutical composition described herein comprises an antimicrobial agent in the form of a micronized antimicrobial agent powder.

The multiparticulates and/or micronized antimicrobial agents described herein are delivered to an auris structure (e.g., inner ear) by means of any type of matrix including solid, liquid or gel matrices. In some embodiments, the multiparticulates and/or micronized antimicrobial agents described herein are delivered to an auris structure (e.g., inner ear) by means of any type of matrix including solid, liquid or gel matrices via intratympanic injection.

Tunable Release Characteristics

The release of active agent from any formulation, composition or device described herein is optionally tunable to the desired release characteristics. In some embodiments, a composition described herein is a solution that is substantially free of gelling components. In such instances, the composition provides essentially immediate release of an active agent. In some of such embodiments, the composition is useful in perfusion of otic structures, e.g., during surgery.

In some embodiments, a composition described herein is a solution that is substantially free of gelling components and comprises micronized otic agent (e.g., a corticosteroid, an antimicrobial agent or the like). In some of such embodiments, the composition provides release of an active agent from about 2 days to about 4 days.

In some embodiments, a composition described herein comprises a gelling agent (e.g., poloxamer 407) and provides release of an active agent over a period of from about 1 day to about 3 days. In some embodiments, a composition described herein comprises a gelling agent (e.g., poloxamer 407) and provides release of an active agent over a period of from about 1 day to about 5 days. In some embodiments, a composition described herein comprises a gelling agent (e.g., poloxamer 407) and provides release of an active agent over a period of from about 2 days to about 7 days.

In some embodiments, a composition described herein comprises a gelling agent (e.g., poloxamer 407) in combination with micronized otic agent and provides extended sustained release over a longer period of time. In some embodiments, a composition described herein comprises about 14-17% of a gelling agent (e.g., poloxamer 407) and micronized otic agent, and provides extended sustained release over a period of from about 1 week to about 3 weeks. In some embodiments, a composition described herein comprises about 18-21% of a gelling agent (e.g., poloxamer 407) and micronized otic agent, and provides extended sustained release over a period of from about 3 weeks to about 6 weeks.

Accordingly, the amount of gelling agent in a composition, and the particle size of an otic agent are tunable to the desired release profile of an otic agent from the composition.

As described herein, compositions comprising micronized otic agents provide extended release over a longer period of time compared to compositions comprising non-micronized otic agents. In some instances, the micronized otic agent provides a steady supply (e.g., +/−20%) of active agent via slow degradation and serves as a depot for the active agent; such a depot effect increases residence time of the otic agent in the ear. In specific embodiments, selection of an appropriate particle size of the active agent (e.g., micronized active agent) in combination with the amount of gelling agent in the composition provides tunable extended release characteristics that allow for release of an active agent over a period of hours, days, weeks or months.

In some embodiments, the viscosity of any formulation described herein is designed to provide a suitable rate of release from an auris compatible gel. In some embodiments, the concentration of a thickening agent (e.g., gelling components such as polyoxyethylene-polyoxypropylene copolymers) allows for a tunable mean dissolution time (MDT). The MDT is inversely proportional to the release rate of an active agent from a composition or device described herein. Experimentally, the released otic agent is optionally fitted to the Korsmeyer-Peppas equation $$\frac{Q}{Q_\alpha} = kt^n + b$$

where Q is the amount of otic agent released at time t, $Q\alpha$ is the overall released amount of otic agent, k is a release constant of the nth order, n is a dimensionless number related to the dissolution mechanism and b is the axis intercept, characterizing the initial burst release mechanism wherein n=1 characterizes an erosion controlled mechanism. The mean dissolution time (MDT) is the sum of different periods of time the drug molecules stay in the matrix before release, divided by the total number of molecules and is optionally calculated by:

$$MDT = \frac{nk^{-1/n}}{n+1}$$

For example, a linear relationship between the mean dissolution time (MDT) of a composition or device and the concentration of the gelling agent (e.g., poloxamer) indicates that the otic agent is released due to the erosion of the polymer gel (e.g., poloxamer) and not via diffusion. In another example, a non-linear relationship indicates release of otic agent via a combination of diffusion and/or polymer gel degradation. In another example, a faster gel elimination time course of a composition or device (a faster release of active agent) indicates lower mean dissolution time (MDT). The concentration of gelling components and/or active agent in a composition are tested to determine suitable parameters for MDT. In some embodiments, injection volumes are also tested to determine suitable parameters for preclinical and clinical studies. The gel strength and concentration of the active agent affects release kinetics of an otic agent from the composition. At low poloxamer concentration, elimination rate is accelerated (MDT is lower). An increase in otic agent concentration in the composition or device prolongs residence time and/or MDT of the otic agent in the ear.

In some embodiments, the MDT for poloxamer from a composition or device described herein is at least 6 hours. In some embodiments, the MDT for poloxamer from a composition or device described herein is at least 10 hours.

In some embodiments, the MDT for an active agent from a composition or device described herein is from about 30 hours to about 48 hours. In some embodiments, the MDT for an active agent from a composition or device described herein is from about 30 hours to about 96 hours. In some embodiments, the MDT for an active agent from a composition or device described herein is from about 30 hours to about 1 week. In some embodiments, the MDT for a composition or device described herein is from about 1 week to about 6 weeks.

In some embodiments, the mean residence time (MRT) for an active agent in a composition or device described herein is from about 20 hours to about 48 hours. In some embodiments, the MRT for an active agent from a composition or device described herein is from about 20 hours to about 96 hours. In some embodiments, the MRT for an active agent from a composition or device described herein is from about 20 hours to about 1 week.

In some embodiments, the MRT for an active agent is about 20 hours. In some embodiments, the MRT for an active agent is about 30 hours. In some embodiments, the MRT for an active agent is about 40 hours. In some embodiments, the MRT for an active agent is about 50 hours. In some embodiments, the MRT for an active agent is about 60 hours. In some embodiments, the MRT for an active agent is about 70 hours. In some embodiments, the MRT for an active agent is about 80 hours. In some embodiments, the MRT for an active agent is about 90 hours. In some embodiments, the MRT for an active agent is about 1 week. In some embodiments, the MRT for an active agent is about 90 hours. In some embodiments, the MRT for a composition or device described herein is from about 1 week to about 6 weeks. In some embodiments, the MRT for an active agent is about 1 week. In some embodiments, the MRT for an active agent is about 2 weeks. In some embodiments, the MRT for an active agent is about 3 weeks. In some embodiments, the MRT for an active agent is about 4 weeks. In some embodiments, the MRT for an active agent is about 5 weeks. The half life of an otic agent and mean residence time of the otic agent are determined for each formulation by measurement of concentration of the otic agent in the perilymph using procedures described herein.

In certain embodiments, any controlled release otic formulation described herein increases the exposure of an otic agent and increases the Area Under the Curve (AUC) in otic fluids (e.g., endolymph and/or perilymph) by about 30%, about 40%, about 50%, about 60%, about 70%, about 80% or about 90% compared to a formulation that is not a controlled release otic formulation. In certain embodiments, any controlled release otic formulation described herein increases the exposure time of an otic agent and decreases the Cmax in otic fluids (e.g., endolymph and/or perilymph) by about 40%, about 30%, about 20%, or about 10%, compared to a formulation that is not a controlled release otic formulation. In certain embodiments, any controlled release otic formulation described herein alters (e.g. reduces) the ratio of Cmax to Cmin compared to a formulation that is not a controlled release otic formulation. In certain embodiments, any controlled release otic formulation described herein increases the exposure of an otic agent and increases the length of time that the concentration of an otic agent is above Cmin by about 30%, about 40%, about 50%, about 60%, about 70%, about 80% or about 90% compared to a formulation that is not a controlled release otic formulation. In certain instances, controlled release formulations described herein delay the time to Cmax. In certain instances, the controlled steady release of a drug prolongs the time the concentration of the drug will stay above the Cmin. In some embodiments, auris compositions described herein prolong the residence time of a drug in the inner ear and provide a stable drug exposure profile. In some instances, an increase in concentration of an active agent in the composition saturates the clearance process and allows for a more rapid and stable steady state to be reached.

Figure 5:
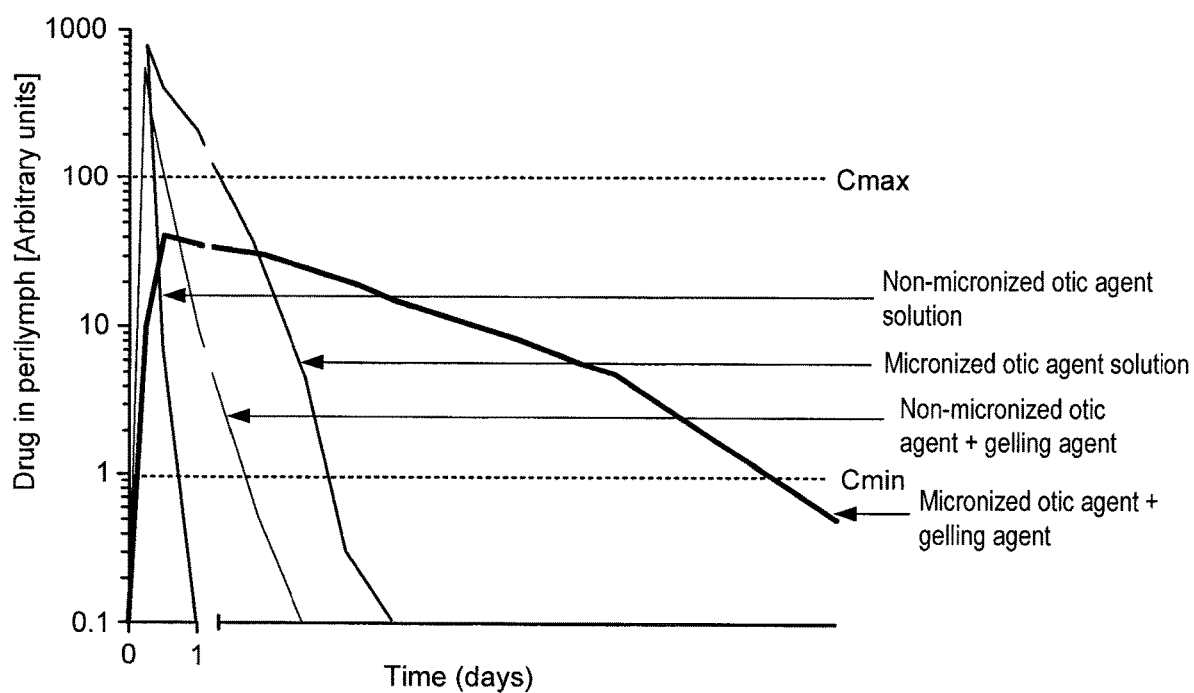
FIG. 5 shows predicted tunable release of an active agent from four compositions.

In certain instances, once drug exposure (e.g., concentration in the endolymph or perilymph) of a drug reaches steady state, the concentration of the drug in the endolymph or perilymph stays at or about the therapeutic dose for an extended period of time (e.g., one day, 2 days, 3 days, 4 days, 5 days, 6 days, or 1 week, 3 weeks, 6 weeks, 2 months). In some embodiments, the steady state concentration of active agent released from a controlled release formulation described herein is about 5 to about 20 times the steady state concentration of an active agent released from a formulation that is not a controlled release formulation. In some embodiments, the steady state concentration of active agent released from a controlled release formulation described herein is about 20 to about 50 times the steady state concentration of an active agent released from a formulation that is not a controlled release formulation. FIG. 5 shows predicted tunable release of an active agent from four compositions.

Pharmaceutical Formulations

Provided herein are pharmaceutical compositions or devices that include at least one antimicrobial agent and a pharmaceutically acceptable diluent(s), excipient(s), or carrier(s). In some embodiments, the pharmaceutical compositions include other medicinal or pharmaceutical agents, carriers, adjuvants, such as preserving, stabilizing, wetting or emulsifying agents, solution promoters, salts for regulating the osmotic pressure, and/or buffers. In other embodiments, the pharmaceutical compositions also contain other therapeutic substances.

In some embodiments, the compositions or devices described herein include a dye to help enhance the visualization of the gel when applied. In some embodiments, dyes that are compatible with the auris-acceptable compositions or devices described herein include Evans blue (e.g., 0.5% of the total weight of an otic formulation), Methylene blue (e.g., 1% of the total weight of an otic formulation), Isosulfan blue (e.g., 1% of the total weight of an otic formulation), Trypan blue (e.g., 0.15% of the total weight of an otic formulation), and/or indocyanine green (e.g., 25 mg/vial). Other common dyes, e.g, FD&C red 40, FD&C red 3, FD&C yellow 5, FD&C yellow 6, FD&C blue 1, FD&C blue2, FD&C green 3, fluorescence dyes (e.g., Fluorescein isothiocyanate, rhodamine, Alexa Fluors, DyLight Fluors) and/or dyes that are visualizable in conjunction with non-invasive imaging techniques such as MRI, CAT scans, PET scans or the like. Gadolinium-based MIl dyes, iodine-base dyes, barium-based dyes or the like are also contemplated for use with any otic formulation described herein. Other dyes that are compatible with any formulation or composition described herein are listed in the Sigma-Aldrich catalog under dyes (which is included herein by reference for such disclosure).

In some embodiments, mechanical or imaging devices are used to monitor or survey the hearing, balance or other auris disorder. For example, magnetic resonance imaging (MRI) devices are specifically contemplated within the scope of the embodiments, wherein the MRI devices (for example, 3 Tesla MIl devices) are capable of evaluating Meniere Disease progression, and subsequent treatment with the pharmaceutical formulations disclosed herein. Gadolinium-based dyes, iodine-base dyes, barium-based dyes or the like are also contemplated for use with any auris-compatible composition or device described herein and/or with any mechanical or imaging devices described herein. In certain embodiments, gadolinium hydrate is used in combination with MM and/or any pharmaceutical composition or device described herein to evaluate disease severity (e.g., size of endolymphatic hydrops), formulation penetration into the inner ear, and/or therapeutic effectiveness of the pharmaceutical formulations/devices in the otic diseases described herein (e.g., Meniere's disease).

Any pharmaceutical composition or device described herein is administered by locating the composition or device in contact with the crista fenestrae cochlea, the round window, the tympanic cavity, the tympanic membrane, the auris media or the auris externa.

In one specific embodiment of the auris-acceptable controlled release antimicrobial agent pharmaceutical formulations described herein, the antimicrobial agent is provided in a gel matrix, also referred to herein as "auris acceptable gel formulations," "auris interna-acceptable gel formulations," "auris media-acceptable gel formulations," "auris externa-acceptable gel formulations", "auris gel formulations" or variations thereof. All of the components of the gel formulation must be compatible with the targeted auris structure. Further, the gel formulations provide controlled release of the antimicrobial agent to the desired site within the targeted auris structure; in some embodiments, the gel formulation also has an immediate or rapid release component for delivery of the antimicrobial agent to the desired target site. In other embodiments, the gel formulation has a sustained release component for delivery of the antimicrobial agent. In some embodiments, the gel formulation comprises a multiparticulate (e.g., micronized) antimicrobial agent. In some embodiments, the auris gel formulations are biodegradeable. In other embodiments, the auris gel formulations include a mucoadhesive excipient to allow adhesion to the external mucous layer of the round window membrane. In yet other embodiments, the auris gel formulations include a penetration enhancer excipient.

In further embodiments, the auris gel formulation contains a viscosity enhancing agent sufficient to provide a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise. In some embodiments, the auris gel formulation contains a viscosity enhancing agent sufficient to provide a viscosity of between about 50,0000 and 1,000,000 centipoise.

In some embodiments, the compositions or devices described herein are low viscosity compositions or devices at body temperature. In some embodiments, low viscosity compositions or devices contain from about 1% to about 10% of a viscosity enhancing agent (e.g., gelling components such as polyoxyethylene-polyoxypropylene copolymers). In some embodiments, low viscosity compositions or devices contain from about 2% to about 10% of a viscosity enhancing agent (e.g., gelling components such as polyoxyethylene-polyoxypropylene copolymers). In some embodiments, low viscosity compositions or devices contain from about 5% to about 10% of a viscosity enhancing agent (e.g., gelling components such as polyoxyethylene-polyoxypropylene copolymers). In some embodiments, low viscosity compositions or devices are substantially free of a viscosity enhancing agent (e.g., gelling components such as polyoxyethylene-polyoxypropylene copolymers). In some embodiments, a low viscosity antimicrobial composition or device described herein provides an apparent viscosity of from about 100 cP to about 10,000 cP. In some embodiments, a low viscosity antimicrobial composition or device described herein provides an apparent viscosity of from about 500 cP to about 10,000 cP. In some embodiments, a low viscosity antimicrobial composition or device described herein provides an apparent viscosity of from about 1000 cP to about 10,000 cP. In some of such embodiments, a low viscosity antimicrobial composition or device is administered in combination with an external otic intervention, e.g., a surgical procedure including but not limited to middle ear surgery, inner ear surgery, typanostomy, cochleostomy, labyrinthotomy, mastoidectomy, stapedectomy, stapedotomy, endolymphatic sacculotomy or the like. In some of such embodiments, a low viscosity antimicrobial composition or device is administered during an otic intervention. In other such embodiments, a low viscosity antimicrobial composition or device is administered before the otic intervention.

In some embodiments, the compositions or devices described herein are high viscosity compositions or devices at body temperature. In some embodiments, high viscosity compositions or devices contain from about 10% to about 25% of a viscosity enhancing agent (e.g., gelling components such as polyoxyethylene-polyoxypropylene copolymers). In some embodiments, high viscosity compositions or devices contain from about 14% to about 22% of a viscosity enhancing agent (e.g., gelling components such as polyoxyethylene-polyoxypropylene copolymers). In some embodiments, high viscosity compositions or devices contain from about 15% to about 21% of a viscosity enhancing agent (e.g., gelling components such as polyoxyethylene-polyoxypropylene copolymers). In some embodiments, a high viscosity antimicrobial composition or device described herein provides an apparent viscosity of from about 100,000 cP to about 1,000,000 cP. In some embodiments, a high viscosity antimicrobial composition or device described herein provides an apparent viscosity of from about 150,000 cP to about 500,000 cP. In some embodiments, a high viscosity antimicrobial composition or device described herein provides an apparent viscosity of from about 250,000 cP to about 500,000 cP. In some of such embodiments, a high viscosity composition or device is a liquid at room temperature and gels at about between room temperature and body temperature (including an individual with a serious fever, e.g., up to about 42° C.). In some embodiments, an antimicrobial high viscosity composition or device is administered as monotherapy for treatment of an otic disease or condition described herein. In some embodiments, an antimicrobial high viscosity composition or device is administered in combination with an external otic intervention, e.g., a surgical procedure including but not limited to middle ear surgery, inner ear surgery, typanostomy, cochleostomy, labyrinthotomy, mastoidectomy, stapedectomy, stapedotomy, endolymphatic sacculotomy or the like. In some of such embodiments, a high viscosity antimicrobial composition or device is administered after the otic intervention. In other such embodiments, a high viscosity antimicrobial composition or device is administered before the otic intervention.

In other embodiments, the auris interna pharmaceutical formulations described herein further provide an auris-acceptable hydrogel; in yet other embodiments, the auris pharmaceutical formulations provide an auris-acceptable microsphere or microparticle; in still other embodiments, the auris pharmaceutical formulations provide an auris-acceptable liposome. In some embodiments, the auris pharmaceutical formulations provide an auris-acceptable foam; in yet other embodiments, the auris pharmaceutical formulations provide an auris-acceptable paint; in still further embodiments, the auris pharmaceutical formulations provide an auris-acceptable in situ forming spongy material. In some embodiments, the auris pharmaceutical formulations provide an auris-acceptable solvent release gel. In some embodiments, the auris pharmaceutical formulations provide an actinic radiation curable gel. Further embodiments include a thermoreversible gel in the auris pharmaceutical formulation, such that upon preparation of the gel at room temperature or below, the formulation is a fluid, but upon application of the gel into or near the auris interna and/or auris media target site, including the tympanic cavity, round window membrane or the crista fenestrae cochleae, the auris-pharmaceutical formulation stiffens or hardens into a gel-like substance.

In further or alternative embodiments, the auris gel formulations are capable of being administered on or near the round window membrane via intratympanic injection. In other embodiments, the auris gel formulations are administered on or near the round window or the crista fenestrae cochleae through entry via a post-auricular incision and surgical manipulation into or near the round window or the crista fenestrae cochleae area. Alternatively, the auris gel formulation is applied via syringe and needle, wherein the needle is inserted through the tympanic membrane and guided to the area of the round window or crista fenestrae cochleae. The auris gel formulations are then deposited on or near the round window or crista fenestrae cochleae for localized treatment of autoimmune otic disorders. In other embodiments, the auris gel formulations are applied via microcathethers implanted into the patient, and in yet further embodiments the formulations are administered via a pump device onto or near the round window membrane. In still further embodiments, the auris gel formulations are applied at or near the round window membrane via a microinjection device. In yet other embodiments, the auris gel formulations are applied in the tympanic cavity. In some embodiments, the auris gel formulations are applied on the tympanic membrane. In still other embodiments, the auris gel formulations are applied onto or in the auditory canal.

In further specific embodiments, any pharmaceutical composition or device described herein comprises a multi-particulate antimicrobial agent in a liquid matrix (e.g., a liquid composition for intratympanic injection, or otic drops). In certain embodiments, any pharmaceutical composition described herein comprises a multiparticulate antimicrobial agent in a solid matrix.

Controlled Release Formulations

In general, controlled release drug formulations impart control over the release of drug with respect to site of release and time of release within the body. As discussed herein, controlled release refers to immediate release, delayed release, sustained release, extended release, variable release, pulsatile release and bi-modal release. Many advantages are offered by controlled release. First, controlled release of a pharmaceutical agent allows less frequent dosing and thus minimizes repeated treatment. Second, controlled release treatment results in more efficient drug utilization and less of the compound remains as a residue. Third, controlled release offers the possibility of localized drug delivery by placement of a delivery device or formulation at the site of disease. Still further, controlled release offers the opportunity to administer and release two or more different drugs, each having a unique release profile, or to release the same drug at different rates or for different durations, by means of a single dosage unit.

Accordingly, one aspect of the embodiments disclosed herein is to provide a controlled release antimicrobial agent auris-acceptable composition or device for the treatment of autoimmune disorders, infections and/or inflammatory disorders. The controlled release aspect of the compositions and/or formulations and/or devices disclosed herein is imparted through a variety of agents, including but not limited to excipients, agents or materials that are acceptable for use in the auris interna or other otic structure. By way of example only, such excipients, agents or materials include an auris-acceptable polymer, an auris-acceptable viscosity enhancing agent, an auris-acceptable gel, an auris-acceptable paint, an auris-acceptable foam, an auris-acceptable xerogel, an auris-acceptable microsphere or microparticle, an auris-acceptable hydrogel, an auris-acceptable in situ forming spongy material, an auris-acceptable actinic radiation curable gel, an auris-acceptable solvent release gel, an auris-acceptable liposome, an auris-acceptable nanocapsule or nanosphere, an auris-acceptable thermoreversible gel, or combinations thereof.

Auris-Acceptable Gels

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions or devices disclosed herein is pseudo plastic, plastic, thixotropic, or dilatant.

In one embodiment the enhanced viscosity auris-acceptable formulation described herein is not a liquid at room temperature. In certain embodiments, the enhanced viscosity formulation is characterized by a phase transition between room temperature and body temperature (including an individual with a serious fever, e.g., up to about 42° C.). In some embodiments, the phase transition occurs at 1° C. below body temperature, at 2° C. below body temperature, at 3° C. below body temperature, at 4° C. below body temperature, at 6° C. below body temperature, at 8° C. below body temperature, or at 10° C. below body temperature. In some embodiments, the phase transition occurs at about 15° C. below body temperature, at about 20° C. below body temperature or at about 25° C. below body temperature. In specific embodiments, the gelation temperature (Tgel) of a formulation described herein is about 20° C., about 25° C., or about 30° C. In certain embodiments, the gelation temperature (Tgel) of a formulation described herein is about 35° C., or about 40° C. In one embodiment, administration of any formulation described herein at about body temperature reduces or inhibits vertigo associated with intratympanic administration of otic formulations. Included within the definition of body temperature is the body temperature of a healthy individual, or an unhealthy individual, including an individual with a fever (up to ~42° C.). In some embodiments, the pharmaceutical compositions or devices described herein are liquids at about room temperature and are administered at or about room temperature, reducing or ameliorating side effects such as, for example, vertigo.

Polymers composed of polyoxypropylene and polyoxyethylene form thermoreversible gels when incorporated into aqueous solutions. These polymers have the ability to change from the liquid state to the gel state at temperatures close to body temperature, therefore allowing useful formulations that are applied to the targeted auris structure(s). The liquid state-to-gel state phase transition is dependent on the polymer concentration and the ingredients in the solution.

Poloxamer 407 (PF-127) is a nonionic surfactant composed of polyoxyethylene-polyoxypropylene copolymers. Other poloxamers include 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. The polymer can be further purified by suitable methods that will enhance gelation properties of the polymer. It contains approximately 70% ethylene oxide, which accounts for its hydrophilicity. It is one of the series of poloxamer ABA block copolymers, whose members share the chemical formula shown below.

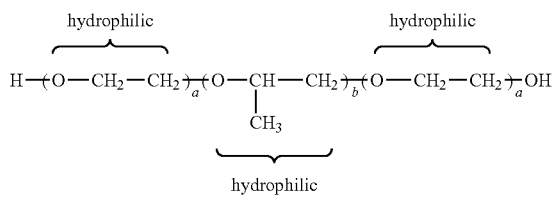

PF-127 is of particular interest since concentrated solutions (>20% w/w) of the copolymer are transformed from low viscosity transparent solutions to solid gels on heating to body temperature. This phenomenon, therefore, suggests that when placed in contact with the body, the gel preparation will form a semi-solid structure and a sustained release depot. Furthermore, PF-127 has good solubilizing capacity, low toxicity and is, therefore, considered a good medium for drug delivery systems.

In an alternative embodiment, the thermogel is a PEG-PLGA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting coplymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PGLA copolymer of 50:50 poly(DL-lactide-co-glycolide) and is 10% w/w of PEG and has a molecular weight of about 6000.

ReGel® is a tradename of MacroMed Incorporated for a class of low molecular weight, biodegradable block copolymers having reverse thermal gelation properties as described in U.S. Pat. Nos. 6,004,573, 6,117,949, 6,201,072, and 6,287,588. It also includes biodegradable polymeric drug carriers disclosed in pending U.S. patent application Ser. Nos. 09/906,041, 09/559,799 and 10/919,603. The biodegradable drug carrier comprises ABA-type or BAB-type triblock copolymers or mixtures thereof, wherein the A-blocks are relatively hydrophobic and comprise biodegradable polyesters or poly(orthoester)s, and the B-blocks are relatively hydrophilic and comprise polyethylene glycol (PEG), said copolymers having a hydrophobic content of between 50.1 to 83% by weight and a hydrophilic content of between 17 to 49.9% by weight, and an overall block copolymer molecular weight of between 2000 and 8000 Daltons. The drug carriers exhibit water solubility at temperatures below normal mammalian body temperatures and undergo reversible thermal gelation to then exist as a gel at temperatures equal to physiological mammalian body temperatures. The biodegradable, hydrophobic A polymer block comprises a polyester or poly(ortho ester), in which the polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-butyrolactone, γ-hydroxybutyric acid, δ-valerolactone, δ-hydroxyvaleric acid, hydroxybutyric acids, malic acid, and copolymers thereof and having an average molecular weight of between about 600 and 3000 Daltons. The hydrophilic B-block segment is preferably polyethylene glycol (PEG) having an average molecular weight of between about 500 and 2200 Daltons.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermoreversible gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermoreversible gel polymer. The antimicrobial agent and various additives such as buffers, salts, and preservatives are subsequently added and dissolved. In some instances the antimicrobial agent and/or other pharmaceutically active agent is suspended if it is insoluble in water. The pH is modulated by the addition of appropriate buffering agents. round window membrane mucoadhesive characteristics are optionally imparted to a thermoreversible gel by incorporation of round window membrane mucoadhesive carbomers, such as Carbopol® 934P, to the composition (Majithiya et al, AAPS PharmSciTech (2006), 7(3), p. E1; EP0551626, both of which is incorporated herein by reference for such disclosure).

In one embodiment are auris-acceptable pharmaceutical gel formulations which do not require the use of an added viscosity enhancing agent. Such gel formulations incorporate at least one pharmaceutically acceptable buffer. In one aspect is a gel formulation comprising an antimicrobial agent and a pharmaceutically acceptable buffer. In another embodiment, the pharmaceutically acceptable excipient or carrier is a gelling agent.

In other embodiments, useful antimicrobial agent auris-acceptable pharmaceutical formulations also include one or more pH adjusting agents or buffering agents to provide an endolymph or perilymph suitable pH. Suitable pH adjusting agents or buffers include, but are not limited to acetate, bicarbonate, ammonium chloride, citrate, phosphate, pharmaceutically acceptable salts thereof and combinations or mixtures thereof. Such pH adjusting agents and buffers are included in an amount required to maintain pH of the composition between a pH of about 5 and about 9, in one embodiment a pH between about 6.5 to about 7.5, and in yet another embodiment at a pH of about 6.5, 6.6, 6.7, 6.8, 6.9, 7.0, 7.1, 7.2, 7.3, 7.4, 7.5. In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the auris media or auris interna's natural buffering system, or does not interfere with the natural pH of the endolymph or perilymph: depending on where in the cochlea the antimicrobial agent formulation is targeted. In some embodiments, from about 10 μM to about 200 mM concentration of a buffer is present in the gel formulation. In certain embodiments, from about a 5 mM to about a 200 mM concentration of a buffer is present. In certain embodiments, from about a 20 mM to about a 100 mM concentration of a buffer is present. In one embodiment is a buffer such as acetate or citrate at slightly acidic pH. In one embodiment the buffer is a sodium acetate buffer having a pH of about 4.5 to about 6.5. In one embodiment the buffer is a sodium citrate buffer having a pH of about 5.0 to about 8.0, or about 5.5 to about 7.0.

In an alternative embodiment, the buffer used is tris (hydroxymethyl)aminomethane, bicarbonate, carbonate or phosphate at slightly basic pH. In one embodiment, the buffer is a sodium bicarbonate buffer having a pH of about 6.5 to about 8.5, or about 7.0 to about 8.0. In another embodiment the buffer is a sodium phosphate dibasic buffer having a pH of about 6.0 to about 9.0.

Also described herein are controlled release formulations or devices comprising an antimicrobial agent and a viscosity enhancing agent. Suitable viscosity-enhancing agents include by way of example only, gelling agents and suspending agents. In one embodiment, the enhanced viscosity formulation does not include a buffer. In other embodiments, the enhanced viscosity formulation includes a pharmaceutically acceptable buffer. Sodium chloride or other tonicity agents are optionally used to adjust tonicity, if necessary.

By way of example only, the auris-acceptable viscosity agent include hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted auris structure include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly (methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), Splenda® (dextrose, maltodextrin and sucralose) or combinations thereof. In specific embodiments, the viscosity-enhancing excipient is a combination of MCC and CMC. In another embodiment, the viscosity-enhancing agent is a combination of carboxymethylated chitosan, or chitin, and alginate. The combination of chitin and alginate with the antimicrobial agents disclosed herein acts as a controlled release formulation, restricting the diffusion of the antimicrobial agents from the formulation. Moreover, the combination of carboxymethylated chitosan and alginate is optionally used to assist in increasing the permeability of the antimicrobial agents through the round window membrane.

In some embodiments is an enhanced viscosity formulation, comprising from about 0.1 mM and about 100 mM of an antimicrobial agent, a pharmaceutically acceptable viscosity agent, and water for injection, the concentration of the viscosity agent in the water being sufficient to provide a enhanced viscosity formulation with a final viscosity from about 100 to about 100,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 1,000,000 cP. In other embodiments, when an even more viscous medium is desired, the biocompatible gel comprises at least about 35%, at least about 45%, at least about 55%, at least about 65%, at least about 70%, at least about 75%, or even at least about 80% or so by weight of the antimicrobial agent. In highly concentrated samples, the biocompatible enhanced viscosity formulation comprises at least about 25%, at least about 35%, at least about 45%, at least about 55%, at least about 65%, at least about 75%, at least about 85%, at least about 90% or at least about 95% or more by weight of the antimicrobial agent.

In some embodiments, the viscosity of the gel formulations presented herein are measured by any means described. For example, in some embodiments, an LVDV-II+CP Cone Plate Viscometer and a Cone Spindle CPE-40 is used to calculate the viscosity of the gel formulation described herein. In other embodiments, a Brookfield (spindle and cup) viscometer is used to calculate the viscosity of the gel formulation described herein. In some embodiments, the viscosity ranges referred to herein are measured at room temperature. In other embodiments, the viscosity ranges referred to herein are measured at body temperature (e.g., at the average body temperature of a healthy human).

In one embodiment, the pharmaceutically acceptable enhanced viscosity auris-acceptable formulation comprises at least one antimicrobial agent and at least one gelling agent. Suitable gelling agents for use in preparation of the gel formulation include, but are not limited to, celluloses, cellulose derivatives, cellulose ethers (e.g., carboxymethylcellulose, ethylcellulose, hydroxyethyl cellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. In some other embodiments, hydroxypropylmethylcellulose (Methocel®) is utilized as the gelling agent. In certain embodiments, the viscosity enhancing agents described herein are also utilized as the gelling agent for the gel formulations presented herein.

In some embodiments, the otic therapeutic agents disclosed herein are dispensed as an auris-acceptable paint. As used herein, paints (also known as film formers) are solutions comprised of a solvent, a monomer or polymer, an active agent, and optionally one or more pharmaceutically-acceptable excipients. After application to a tissue, the solvent evaporates leaving behind a thin coating comprised of the monomers or polymers, and the active agent. The coating protects active agents and maintains them in an immobilized state at the site of application. This decreases the amount of active agent which may be lost and correspondingly increases the amount delivered to the subject. By way of non-limiting example, paints include collodions (e.g. Flexible Collodion, USP), and solutions comprising saccharide siloxane copolymers and a cross-linking agent. Collodions are ethyl ether/ethanol solutions containing pyroxylin (a nitrocellulose). After application, the ethyl ether/ethanol solution evaporates leaving behind a thin film of pyroxylin. In solutions comprising saccharide siloxane copolymers, the saccharide siloxane copolymers form the coating after evaporation of the solvent initiates the cross-linking of the saccharide siloxane copolymers. For additional disclosures regarding paints, see *Remington: The Science and Practice of Pharmacy* which is hereby incorporated with respect to this subject matter. The paints contemplated for use herein, are flexible such that they do not interfere with the propagation of pressure waves through the ear. Further, the paints may be applied as a liquid (i.e. solution, suspension, or emulsion), a semisolid (i.e. a gel, foam, paste, or jelly) or an aerosol.

In some embodiments, the otic therapeutic agents disclosed herein are dispensed as a controlled-release foam. Examples of suitable foamable carriers for use in the compositions disclosed herein include, but are not limited to, alginate and derivatives thereof, carboxymethylcellulose and derivatives thereof, collagen, polysaccharides, including, for example, dextran, dextran derivatives, pectin, starch, modified starches such as starches having additional carboxyl and/or carboxamide groups and/or having hydrophilic side-chains, cellulose and derivatives thereof, agar and derivatives thereof, such as agar stabilised with polyacrylamide, polyethylene oxides, glycol methacrylates, gelatin, gums such as xanthum, guar, karaya, gellan, arabic, tragacanth and locust bean gum, or combinations thereof. Also suitable are the salts of the aforementioned carriers, for example, sodium alginate. The formulation optionally further comprises a foaming agent, which promotes the formation of the foam, including a surfactant or external propellant. Examples of suitable foaming agents include cetrimide, lecithin, soaps, silicones and the like. Commercially available surfactants such as Tween® are also suitable.

In some embodiments, other gel formulations are useful depending upon the particular antimicrobial agent, other pharmaceutical agent or excipients/additives used, and as such are considered to fall within the scope of the present disclosure. For example, other commercially-available glycerin-based gels, glycerin-derived compounds, conjugated, or crosslinked gels, matrices, hydrogels, and polymers, as well as gelatins and their derivatives, alginates, and alginate-based gels, and even various native and synthetic hydrogel and hydrogel-derived compounds are all expected to be useful in the antimicrobial agent formulations described herein. In some embodiments, auris-acceptable gels include, but are not limited to, alginate hydrogels SAF®-Gel (ConvaTec, Princeton, N.J.), Duoderm® Hydroactive Gel (ConvaTec), Nu-Gel® (Johnson & Johnson Medical, Arlington, Tex.); Carrasyn® (V) Acemannan Hydrogel (Carrington Laboratories, Inc., Irving, Tex.); glycerin gels Elta® Hydrogel (Swiss-American Products, Inc., Dallas, Tex.) and K-Y® Sterile (Johnson & Johnson). In further embodiments, biodegradable biocompatible gels also represent compounds present in auris-acceptable formulations disclosed and described herein.

In some formulations developed for administration to a mammal, and for compositions formulated for human administration, the auris-acceptable gel comprises substantially all of the weight of the composition. In other embodiments, the auris-acceptable gel comprises as much as about 98% or about 99% of the composition by weight. This is desirous when a substantially non-fluid, or substantially viscous formulation is needed. In a further embodiment, when slightly less viscous, or slightly more fluid auris-acceptable pharmaceutical gel formulations are desired, the biocompatible gel portion of the formulation comprises at least about 50% by weight, at least about 60% by weight, at least about 70% by weight, or even at least about 80% or 90% by weight of the compound. All intermediate integers within these ranges are contemplated to fall within the scope of this disclosure, and in some alternative embodiments, even more fluid (and consequently less viscous) auris-acceptable gel compositions are formulated, such as for example, those in which the gel or matrix component of the mixture comprises not more than about 50% by weight, not more than about 40% by weight, not more than about 30% by weight, or even those than comprise not more than about 15% or about 20% by weight of the composition.

Auris-Acceptable Suspending Agents

In one embodiment, at least one antimicrobial agent is included in a pharmaceutically acceptable enhanced viscosity formulation wherein the formulation further comprises at least one suspending agent, wherein the suspending agent assists in imparting controlled release characteristics to the formulation. In some embodiments, suspending agents also serve to increase the viscosity of the auris-acceptable antimicrobial agent formulations and compositions.

Suspending agents include, by way of example only, compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), sodium carboxymethylcellulose, methylcellulose, hydroxypropylmethylcellulose (hypromellose), hydroxymethylcellulose acetate stearate, polysorbate-80, hydroxyethyl cellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like. In some embodiments, useful aqueous suspensions also contain one or more polymers as suspending agents. Useful polymers include water-soluble polymers such as cellulosic polymers, e.g., hydroxypropyl methylcellulose, and water-insoluble polymers such as cross-linked carboxyl-containing polymers.

In one embodiment, the present disclosure provides auris-acceptable gel compositions comprising a therapeutically effective amount of an antimicrobial agent in a hydroxyethyl cellulose gel. Hydroxyethyl cellulose (HEC) is obtained as a dry powder which is reconstituted in water or an aqueous buffer solution to give the desired viscosity (generally about 200 cps to about 30,000 cps, corresponding to about 0.2 to about 10% HEC). In one embodiment the concentration of HEC is between about 1% and about 15%, about 1% and about 2%, or about 1.5% to about 2%.

In other embodiments, the auris-acceptable formulations, including gel formulations and viscosity-enhanced formulations, further include excipients, other medicinal or pharmaceutical agents, carriers, adjuvants, such as preserving, stabilizing, wetting or emulsifying agents, solution promoters, salts, solubilizers, an antifoaming agent, an antioxidant, a dispersing agent, a wetting agent, a surfactant, and combinations thereof.

Auris-Acceptable Actinic Radiation Curable Gel

In other embodiments, the gel is an actinic radiation curable gel, such that following administration to or near the targeted auris structure, use of actinic radiation (or light, including UV light, visible light, or infrared light) the desired gel properties are formed. By way of example only, fiber optics are used to provide the actinic radiation so as to form the desired gel properties. In some embodiments, the fiber optics and the gel administration device form a single unit. In other embodiments, the fiber optics and the gel administration device are provided separately.

Auris-Acceptable Solvent Release Gel

In some embodiments, the gel is a solvent release gel such that the desired gel properties are formed after administration to or near the targeted auris structure, that is, as the solvent in the injected gel formulation diffuses out the gel, a gel having the desired gel properties is formed. For example, a formulation that comprises sucrose acetate isobutyrate, a pharmaceutically acceptable solvent, one or more additives, and the antimicrobial agent is administered at or near the round window membrane: diffusion of the solvent out of the injected formulation provides a depot having the desired gel properties. For example, use of a water soluble solvent provides a high viscosity depot when the solvent diffuses rapidly out of the injected formulation. On the other hand, use of a hydrophobic solvent (e.g., benzyl benzoate) provides a less viscous depot. One example of an auris-acceptable solvent release gel formulation is the SABER™ Delivery System marketed by DURECT Corporation.

Auris-Acceptable In Situ Forming Spongy Material

Also contemplated within the scope of the embodiments is the use of a spongy material, formed in situ in the auris interna or auris media. In some embodiments, the spongy material is formed from hyaluronic acid or its derivatives. The spongy material is impregnated with a desired antimicrobial agent and placed within the auris media so as to provide controlled release of the antimicrobial agent within the auris media, or in contact with the round window membrane so as to provide controlled release of the antimicrobial agent into the auris interna. In some embodiments, the spongy material is biodegradable.

Round Window Membrane Mucoadhesives

Also contemplated within the scope of the embodiments is the addition of a round window membrane mucoadhesive with the antimicrobial agent formulations and compositions and devices disclosed herein. The term 'mucoadhesion' is used for materials that bind to the mucin layer of a biological membrane, such as the external membrane of the 3-layered round window membrane. To serve as round window membrane mucoadhesive polymers, the polymers possess some general physiochemical features such as predominantly anionic hydrophilicity with numerous hydrogen bond forming groups, suitable surface property for wetting mucus/mucosal tissue surfaces or sufficient flexibility to penetrate the mucus network.

Round window membrane mucoadhesive agents that are used with the auris-acceptable formulations include, but are not limited to, at least one soluble polyvinylpyrrolidone polymer (PVP); a water-swellable, but water-insoluble, fibrous, cross-linked carboxy-functional polymer; a cross-linked poly(acrylic acid) (e.g. Carbopol® 947P); a carbomer homopolymer; a carbomer copolymer; a hydrophilic polysaccharide gum, maltodextrin, a cross-linked alginate gum gel, a water-dispersible polycarboxylated vinyl polymer, at least two particulate components selected from the group consisting of titanium dioxide, silicon dioxide, and clay, or a mixture thereof. The round window membrane mucoadhesive agent is optionally used in combination with an auris-acceptable viscosity increasing excipient, or used alone to increase the interaction of the composition with the mucosal layer target otic component. In one non-limiting example, the mucoadhesive agent is maltodextrin. In some embodiments, the mucoadhesive agent is an alginate gum. When used, the round window membrane mucoadhesive character imparted to the composition is at a level that is sufficient to deliver an effective amount of the antimicrobial agent composition to, for example, the mucosal layer of round window membrane or the crista fenestrae cochleae in an amount that coats the mucosal membrane, and thereafter deliver the composition to the affected areas, including by way of example only, the vestibular and/or cochlear structures of the auris interna. When used, the mucoadhesive characteristics of the compositions provided herein are determined, and using this information (along with the other teachings provided herein), the appropriate amounts are determined. One method for determining sufficient mucoadhesiveness includes monitoring changes in the interaction of the composition with a mucosal layer, including but not limited to measuring changes in residence or retention time of the composition in the absence and presence of the mucoadhesive excipient.

Mucoadhesive agents have been described, for example, in U.S. Pat. Nos. 6,638,521, 6,562,363, 6,509,028, 6,348,502, 6,319,513, 6,306,789, 5,814,330, and 4,900,552, each of which is hereby incorporated by reference for such disclosure.

In another non-limiting example, a mucoadhesive agent is, for example, at least two particulate components selected from titanium dioxide, silicon dioxide, and clay, wherein the composition is not further diluted with any liquid prior to administration and the level of silicon dioxide, if present, is from about 3% to about 15%, by weight of the composition. Silicon dioxide, if present, includes fumed silicon dioxide, precipitated silicon dioxide, coacervated silicon dioxide, gel silicon dioxide, and mixtures thereof. Clay, if present, includes kaolin minerals, serpentine minerals, smectites, illite or a mixture thereof. For example, clay includes laponite, bentonite, hectorite, saponite, montmorillonites or a mixture thereof.

In one non-limiting example, the round window membrane mucoadhesive agent is maltodextrin. Maltodextrin is a carbohydrate produced by the hydrolysis of starch that is optionally derived from corn, potato, wheat or other plant products. Maltodextrin is optionally used either alone or in combination with other round window membrane mucoadhesive agents to impart mucoadhesive characteristics on the compositions disclosed herein. In one embodiment, a combination of maltodextrin and a carbopol polymer are used to increase the round window membrane mucoadhesive characteristics of the compositions or devices disclosed herein.

In another embodiment, the round window membrane mucoadhesive agent is an alkyl-glycoside and/or a saccharide alkyl ester. As used herein, an "alkyl-glycoside" means a compound comprising any hydrophilic saccharide (e.g. sucrose, maltose, or glucose) linked to a hydrophobic alkyl. In some embodiments, the round window membrane mucoadhesive agent is an alkyl-glycoside wherein the alkyl-glycoside comprises a sugar linked to a hydrophobic alkyl (e.g., an alkyl comprising about 6 to about 25 carbon atoms) by an amide linkage, an amine linkage, a carbamate linkage, an ether linkage, a thioether linkage, an ester linkage, a thioester linkage, a glycosidic linkage, a thioglycosidic linkage, and/or a ureide linkage. In some embodiments, the round window membrane mucoadhesive agent is a hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-maltoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-glucoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-sucroside; hexyl-, heptyl-, octyl-, dodecyl-, tridecyl-, and tetradecyl-β-D-thiomaltoside; dodecyl maltoside; heptyl- or octyl-1-thio-α- or β-D-glucopyranoside; alkyl thiosucroses; alkyl maltotriosides; long chain aliphatic carbonic acid amides of sucrose β-aminoalkyl ethers; derivatives of palatinose or isomaltamine linked by an amide linkage to an alkyl chain and derivatives of isomaltamine linked by urea to an alkyl chain; long chain aliphatic carbonic acid ureides of sucrose β-amino-alkyl ethers and long chain aliphatic carbonic acid amides of sucrose β-amino-alkyl ethers. In some embodiments, the round window membrane mucoadhesive agent is an alkyl-glycoside wherein the alkyl glycoside is maltose, sucrose, glucose, or a combination thereof linked by a glycosidic linkage to an alkyl chain of 9-16 carbon atoms (e.g., nonyl-, decyl-, dodecyl- and tetradecyl sucroside; nonyl-, decyl-, dodecyl- and tetradecyl glucoside; and nonyl-, decyl-, dodecyl- and tetradecyl maltoside). In some embodiments, the round window membrane mucoadhesive agent is an alkyl-glycoside wherein the alkyl glycoside is dodecyl-maltoside, tridecylmaltoside, and tetradecylmaltoside.

In some embodiments, the round window membrane mucoadhesive agent is an alkyl-glycoside wherein the alkyl-glycoside is a disaccharide with at least one glucose. In some embodiments, the auris acceptable penetration enhancer is a surfactant comprising α-D-glucopyranosyl-β-glycopyranoside, n-Dodecyl-4-O-α-D-glucopyranosyl-β-glycopyranoside, and/or n-tetradecyl-4-O-α-D-glucopyranosyl-β-glycopyranoside. In some embodiments, the round window membrane mucoadhesive agent is an alkyl-glycoside wherein the alkyl-glycoside has a critical miscelle concentration (CMC) of less than about 1 mM in pure water or in aqueous solutions. In some embodiments, the round window membrane mucoadhesive agent is an alkyl-glycoside wherein an oxygen atom within the alkyl-glycoside is substituted with a sulfur atom. In some embodiments, the round window membrane mucoadhesive agent is an alkyl-glycoside wherein the alkylglycoside is the β anomer. In some embodiments, the round window membrane mucoadhesive agent is an alkyl-glycoside wherein the alkylglycoside comprises 90%, 91%, 92%, 93%, 94%, 95%, 96%, 97%, 98%, 99%, 99.1%, 99.5%, or 99.9% of the β anomer.

Auris-Acceptable Controlled Release Particles

Antimicrobial agents and/or other pharmaceutical agents disclosed herein are optionally incorporated within controlled release particles, lipid complexes, liposomes, nanoparticles, microparticles, microspheres, coacervates, nanocapsules or other agents which enhance or facilitate the localized delivery of the antimicrobial agent. In some embodiments, a single enhanced viscosity formulation is used, in which at least one antimicrobial agent is present, while in other embodiments, a pharmaceutical formulation that comprises a mixture of two or more distinct enhanced viscosity formulations is used, in which at least one antimicrobial agent is present. In some embodiments, combinations of sols, gels and/or biocompatible matrices is also employed to provide desirable characteristics of the controlled release antimicrobial agent compositions or formulations. In certain embodiments, the controlled release antimicrobial agent formulations or compositions are cross-linked by one or more agents to alter or improve the properties of the composition.

Examples of microspheres relevant to the pharmaceutical formulations disclosed herein include: Luzzi, L. A., J. Pharm. Psy. 59:1367 (1970); U.S. Pat. No. 4,530,840; Lewis, D. H., "Controlled Release of Bioactive Agents from Lactides/Glycolide Polymers" in Biodegradable Polymers as Drug Delivery Systems, Chasin, M. and Langer, R., eds., Marcel Decker (1990); U.S. Pat. No. 4,675,189; Beck et al., "Poly(lactic acid) and Poly(lactic acid-co-glycolic acid) Contraceptive Delivery Systems," in Long Acting Steroid Contraception, Mishell, D. R., ed., Raven Press (1983); U.S. Pat. Nos. 4,758,435; 3,773,919; 4,474,572. Examples of protein therapeutics formulated as microspheres include: U.S. Pat. Nos. 6,458,387; 6,268,053; 6,090,925; 5,981,719; and 5,578,709, and are herein incorporated by reference for such disclosure.

Microspheres usually have a spherical shape, although irregularly-shaped microparticles are possible. Microspheres may vary in size, ranging from submicron to 1000 micron diameters. Microspheres suitable for use with the auris-acceptable formulations disclosed herein are submicron to 250 micron diameter microspheres, allowing administration by injection with a standard gauge needle. The auris-acceptable microspheres are prepared by any method which produces microspheres in a size range acceptable for use in an injectable composition. Injection is optionally accomplished with standard gauge needles used for administering liquid compositions.

Suitable examples of polymeric matrix materials for use in the auris-acceptable controlled release particles herein include poly(glycolic acid), poly-d,l-lactic acid, poly-1-lactic acid, copolymers of the foregoing, poly(aliphatic carboxylic acids), copolyoxalates, polycaprolactone, polydioxonene, poly(orthocarbonates), poly(acetals), poly(lactic acid-caprolactone), polyorthoesters, poly(glycolic acid-caprolactone), polydioxonene, polyanhydrides, polyphosphazines, and natural polymers including albumin, casein, and some waxes, such as, glycerol mono- and distearate, and the like. Various commercially available poly (lactide-co-glycolide) materials (PLGA) are optionally used in the method disclosed herein. For example, poly (d,l-lactic-co-glycolic acid) is commercially available from Boehringer-Ingelheim as RESOMER RG 503 H. This product has a mole percent composition of 50% lactide and 50% glycolide. These copolymers are available in a wide range of molecular weights and ratios of lactic acid to glycolic acid. One embodiment includes the use of the polymer poly(d,l-lactide-co-glycolide). The molar ratio of lactide to glycolide in such a copolymer includes the range of from about 95:5 to about 50:50.

The molecular weight of the polymeric matrix material is of some importance. The molecular weight should be high enough so that it forms satisfactory polymer coatings, i.e., the polymer should be a good film former. Usually, a satisfactory molecular weight is in the range of 5,000 to 500,000 daltons. The molecular weight of a polymer is also important from the point of view that molecular weight influences the biodegradation rate of the polymer. For a diffusional mechanism of drug release, the polymer should remain intact until all of the drug is released from the microparticles and then degrade. The drug is also released from the microparticles as the polymeric excipient bioerodes. By an appropriate selection of polymeric materials a microsphere formulation is made such that the resulting microspheres exhibit both diffusional release and biodegradation release properties. This is useful in affording multiphasic release patterns.

A variety of methods are known by which compounds are encapsulated in microspheres. In these methods, the antimicrobial agent is generally dispersed or emulsified, using stirrers, agitators, or other dynamic mixing techniques, in a solvent containing a wall-forming material. Solvent is then removed from the microspheres, and thereafter the microsphere product is obtained.

In one embodiment, controlled release antimicrobial agent formulations are made through the incorporation of the antimicrobial agents and/or other pharmaceutical agents into ethylene-vinyl acetate copolymer matrices. (See U.S. Pat. No. 6,083,534, incorporated herein for such disclosure). In another embodiment, antimicrobial agents are incorporated into poly (lactic-glycolic acid) or poly-L-lactic acid microspheres. Id. In yet another embodiment, the antimicrobial agents are encapsulated into alginate microspheres. (See U.S. Pat. No. 6,036,978, incorporated herein for such disclosure). Biocompatible methacrylate-based polymers to encapsulate the antimicrobial agent compounds or compositions are optionally used in the formulations and methods disclosed herein. A wide range of methacrylate-based polymer systems are commercially available, such as the EUDRAGIT polymers marketed by Evonik. One useful aspect of methacrylate polymers is that the properties of the formulation are varied by incorporating various co-polymers. For example, poly(acrylic acid-co-methylmethacrylate) microparticles exhibit enhanced mucoadhesion properties as the carboxylic acid groups in the poly(acrylic acid) form hydrogen bonds with mucin (Park et al, Pharm. Res. (1987) 4(6):457-464). Variation of the ratio between acrylic acid and methylmethacrylate monomers serves to modulate the properties of the co-polymer. Methacrylate-based microparticles have also been used in protein therapeutic formulations (Naha et al, Journal of Microencapsulation 4 Feb. 2008 (online publication)). In one embodiment, the enhanced viscosity auris-acceptable formulations described herein comprises antimicrobial agent microspheres wherein the microspheres are formed from a methacrylate polymer or copolymer. In an additional embodiment, the enhanced viscosity formulation described herein comprises antimicrobial agent microspheres wherein the microspheres are mucoadhesive. Other controlled release systems, including incorporation or deposit of polymeric materials or matrices onto solid or hollow spheres containing antimicrobial agents, are also explicitly contemplated within the embodiments disclosed herein. The types of controlled release systems available without significantly losing activity of the antimicrobial agent are determined using the teachings, examples, and principles disclosed herein An example of a conventional microencapsulation process for pharmaceutical preparations is shown in U.S. Pat. No. 3,737,337, incorporated herein by reference for such disclosure. The antimicrobial agent substances to be encapsulated or embedded are dissolved or dispersed in the organic solution of the polymer (phase A), using conventional mixers, including (in the preparation of dispersion) vibrators and high-speed stirrers, etc. The dispersion of phase (A), containing the core material in solution or in suspension, is carried out in the aqueous phase (B), again using conventional mixers, such as high-speed mixers, vibration mixers, or even spray nozzles, in which case the particle size of the microspheres will be determined not only by the concentration of phase (A), but also by the emulsate or microsphere size. With conventional techniques for the microencapsulation of antimicrobial agents, the microspheres form when the solvent containing an active agent and a polymer is emulsified or dispersed in an immiscible solution by stirring, agitating, vibrating, or some other dynamic mixing technique, often for a relatively long period of time.

Methods for the construction of microspheres are also described in U.S. Pat. Nos. 4,389,330, and 4,530,840, incorporated herein by reference for such disclosure. The desired antimicrobial agent is dissolved or dispersed in an appropriate solvent. To the agent-containing medium is added the polymeric matrix material in an amount relative to the active ingredient which gives a product of the desired loading of active agent. Optionally, all of the ingredients of the antimicrobial agent microsphere product can be blended in the solvent medium together. Suitable solvents for the agent and the polymeric matrix material include organic solvents such as acetone, halogenated hydrocarbons such as chloroform, methylene chloride and the like, aromatic hydrocarbon compounds, halogenated aromatic hydrocarbon compounds, cyclic ethers, alcohols, ethyl acetate and the like.

The mixture of ingredients in the solvent is emulsified in a continuous-phase processing medium; the continuous-phase medium being such that a dispersion of microdroplets containing the indicated ingredients is formed in the continuous-phase medium. Naturally, the continuous-phase processing medium and the organic solvent must be immiscible, and includes water although nonaqueous media such as xylene and toluene and synthetic oils and natural oils are optionally used. Optionally, a surfactant is added to the continuous-phase processing medium to prevent the microparticles from agglomerating and to control the size of the solvent microdroplets in the emulsion. A preferred surfactant-dispersing medium combination is a 1 to 10 wt. % poly (vinyl alcohol) in water mixture. The dispersion is formed by mechanical agitation of the mixed materials. An emulsion is optionally formed by adding small drops of the active agent-wall forming material solution to the continuous phase processing medium. The temperature during the formation of the emulsion is not especially critical but influences the size and quality of the microspheres and the solubility of the drug in the continuous phase. It is desirable to have as little of the agent in the continuous phase as possible. Moreover, depending on the solvent and continuous-phase processing medium employed, the temperature must not be too low or the solvent and processing medium will solidify or the processing medium will become too viscous for practical purposes, or too high that the processing medium will evaporate, or that the liquid processing medium will not be maintained. Moreover, the temperature of the medium cannot be so high that the stability of the particular agent being incorporated in the microspheres is adversely affected. Accordingly, the dispersion process is conducted at any temperature which maintains stable operating conditions, which preferred temperature being about 15° C. to 60° C., depending upon the drug and excipient selected.

The dispersion which is formed is a stable emulsion and from this dispersion the organic solvent immiscible fluid is optionally partially removed in the first step of the solvent removal process. The solvent is removed by techniques such as heating, the application of a reduced pressure or a combination of both. The temperature employed to evaporate solvent from the microdroplets is not critical, but should not be that high that it degrades the antimicrobial agent employed in the preparation of a given microparticle, nor should it be so high as to evaporate solvent at such a rapid rate to cause defects in the wall forming material. Generally, from 5 to 75%, of the solvent is removed in the first solvent removal step.

After the first stage, the dispersed microparticles in the solvent immiscible fluid medium are isolated from the fluid medium by any convenient means of separation. Thus, for example, the fluid is decanted from the microsphere or the microsphere suspension is filtered. Still other, various combinations of separation techniques are used if desired.

Following the isolation of the microspheres from the continuous-phase processing medium, the remainder of the solvent in the microspheres is removed by extraction. In this step, the microspheres are suspended in the same continuous-phase processing medium used in step one, with or without surfactant, or in another liquid. The extraction medium removes the solvent from the microspheres and yet does not dissolve the microspheres. During the extraction, the extraction medium with dissolved solvent is optionally removed and replaced with fresh extraction medium. This is best done on a continual basis. The rate of extraction medium replenishment of a given process is a variable which is determined at the time the process is performed and, therefore, no precise limits for the rate must be predetermined. After the majority of the solvent has been removed from the microspheres, the microspheres are dried by exposure to air or by other conventional drying techniques such as vacuum drying, drying over a desiccant, or the like. This process is very efficient in encapsulating the antimicrobial agent since core loadings of up to 80 wt. %, preferably up to 60 wt. % are obtained.

Alternatively, controlled release microspheres containing an antimicrobial agent is prepared through the use of static mixers. Static or motionless mixers consist of a conduit or tube in which is received a number of static mixing agents. Static mixers provide homogeneous mixing in a relatively short length of conduit, and in a relatively short period of time. With static mixers, the fluid moves through the mixer, rather than some part of the mixer, such as a blade, moving through the fluid.

A static mixer is optionally used to create an emulsion. When using a static mixer to form an emulsion, several factors determine emulsion particle size, including the density and viscosity of the various solutions or phases to be mixed, volume ratio of the phases, interfacial tension between the phases, static mixer parameters (conduit diameter; length of mixing element; number of mixing elements), and linear velocity through the static mixer. Temperature is a variable because it affects density, viscosity, and interfacial tension. The controlling variables are linear velocity, sheer rate, and pressure drop per unit length of static mixer.

In order to create microspheres containing an antimicrobial agent using a static mixer process, an organic phase and an aqueous phase are combined. The organic and aqueous phases are largely or substantially immiscible, with the aqueous phase constituting the continuous phase of the emulsion. The organic phase includes an antimicrobial agent as well as a wall-forming polymer or polymeric matrix material. The organic phase is prepared by dissolving an antimicrobial agent in an organic or other suitable solvent, or by forming a dispersion or an emulsion containing the antimicrobial agent. The organic phase and the aqueous phase are pumped so that the two phases flow simultaneously through a static mixer, thereby forming an emulsion which comprises microspheres containing the antimicrobial agent encapsulated in the polymeric matrix material. The organic and aqueous phases are pumped through the static mixer into a large volume of quench liquid to extract or remove the organic solvent. Organic solvent is optionally removed from the microspheres while they are washing or being stirred in the quench liquid. After the microspheres are washed in a quench liquid, they are isolated, as through a sieve, and dried.

In one embodiment, microspheres are prepared using a static mixer. The process is not limited to the solvent extraction technique discussed above, but is used with other encapsulation techniques. For example, the process is optionally used with a phase separation encapsulation technique. To do so, an organic phase is prepared that comprises an antimicrobial agent suspended or dispersed in a polymer solution. The non-solvent second phase is free from solvents for the polymer and active agent. A preferred non-solvent second phase is silicone oil. The organic phase and the non-solvent phase are pumped through a static mixer into a non-solvent quench liquid, such as heptane. The semi-solid particles are quenched for complete hardening and washing. The process of microencapsulation includes spray drying, solvent evaporation, a combination of evaporation and extraction, and melt extrusion.

In another embodiment, the microencapsulation process involves the use of a static mixer with a single solvent. This process is described in detail in U.S. application Ser. No. 08/338,805, herein incorporated by reference for such disclosure. An alternative process involves the use of a static mixer with co-solvents. In this process, biodegradable microspheres comprising a biodegradable polymeric binder and an antimicrobial agent are prepared, which comprises a blend of at least two substantially non-toxic solvents, free of halogenated hydrocarbons to dissolve both the agent and the polymer. The solvent blend containing the dissolved agent and polymer is dispersed in an aqueous solution to form droplets. The resulting emulsion is then added to an aqueous extraction medium preferably containing at least one of the solvents of the blend, whereby the rate of extraction of each solvent is controlled, whereupon the biodegradable microspheres containing the pharmaceutically active agent are formed. This process has the advantage that less extraction medium is required because the solubility of one solvent in water is substantially independent of the other and solvent selection is increased, especially with solvents that are particularly difficult to extract.

Nanoparticles are also contemplated for use with the antimicrobial agents disclosed herein. Nanoparticles are material structures of about 100 nm or less in size. One use of nanoparticles in pharmaceutical formulations is the formation of suspensions as the interaction of the particle surface with solvent is strong enough to overcome differences in density. Nanoparticle suspensions are sterilized as the nanoparticles are small enough to be subjected to sterilizing filtration (see, e.g., U.S. Pat. No. 6,139,870, herein incorporated by reference for such disclosure). Nanoparticles comprise at least one hydrophobic, water-insoluble and water-indispersible polymer or copolymer emulsified in a solution or aqueous dispersion of surfactants, phospholipids or fatty acids. The antimicrobial agent is optionally introduced with the polymer or the copolymer into the nanoparticles.

Lipid nanocapsules as controlled release structures, as well for penetrating the round window membrane and reaching auris interna and/or auris media targets, is also contemplated herein. Lipid nanocapsules are optionally formed by emulsifying capric and caprylic acid triglycerides (Labrafac WL 1349; avg. mw 512), soybean lecithin (LIPOID® S75-3; 69% phosphatidylcholine and other phospholipids), surfactant (for example, Solutol HS15), a mixture of polyethylene glycol 660 hydroxystearate and free polyethylene glycol 660; NaCl and water. The mixture is stirred at room temperature to obtain an oil emulsion in water. After progressive heating at a rate of 4° C./min under magnetic stirring, a short interval of transparency should occur close to 70° C., and the inverted phase (water droplets in oil) obtained at 85° C. Three cycles of cooling and heating is then applied between 85° C. and 60° C. at the rate of 4° C./min, and a fast dilution in cold water at a temperature close to 0° C. to produce a suspension of nanocapsules. To encapsulate the antimicrobial agents, the agent is optionally added just prior to the dilution with cold water.

Antimicrobial agents are also inserted into the lipid nanocapsules by incubation for 90 minutes with an aqueous micellar solution of the auris active agent. The suspension is then vortexed every 15 minutes, and then quenched in an ice bath for 1 minute.

Suitable auris-acceptable surfactants are, by way of example, cholic acid or taurocholic acid salts. Taurocholic acid, the conjugate formed from cholic acid and taurine, is a fully metabolizable sulfonic acid surfactant. An analog of taurocholic acid, tauroursodeoxycholic acid (TUDCA), is a naturally occurring bile acid and is a conjugate of taurine and ursodeoxycholic acid (UDCA). Other naturally occurring anionic (e.g., galactocerebroside sulfate), neutral (e.g., lactosylceramide) or zwitterionic surfactants (e.g., sphingomyelin, phosphatidyl choline, palmitoyl carnitine) are optionally used to prepare nanoparticles.

The auris-acceptable phospholipids are chosen, by way of example, from natural, synthetic or semi-synthetic phospholipids; lecithins (phosphatidylcholine) such as, for example, purified egg or soya lecithins (lecithin E100, lecithin E80 and phospholipons, for example phospholipon 90), phosphatidylethanolamine, phosphatidylserine, phosphatidylinositol, phosphatidylglycerol, dipalmitoylphosphatidylcholine, dipalmitoylglycerophosphatidylcholine, dimyristoylphosphatidylcholine, di stearoylphosphatidylcholine and phosphatidic acid or mixtures thereof are used more particularly.

Fatty acids for use with the auris-acceptable formulations are chosen from, by way of example, lauric acid, mysristic acid, palmitic acid, stearic acid, isostearic acid, arachidic acid, behenic acid, oleic acid, myristoleic acid, palmitoleic acid, linoleic acid, alpha-linoleic acid, arachidonic acid, eicosapentaenoic acid, erucic acid, docosahexaenoic acid, and the like.

Suitable auris-acceptable surfactants are selected from known organic and inorganic pharmaceutical excipients. Such excipients include various polymers, low molecular weight oligomers, natural products, and surfactants. Preferred surface modifiers include nonionic and ionic surfactants. Two or more surface modifiers are used in combination.

Representative examples of auris-acceptable surfactants include cetyl pyridinium chloride, gelatin, casein, lecithin (phosphatides), dextran, glycerol, gum acacia, cholesterol, tragacanth, stearic acid, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters; dodecyl trimethyl ammonium bromide, polyoxyethylenestearates, colloidal silicon dioxide, phosphates, sodium dodecylsulfate, carboxymethylcellulose calcium, hydroxypropyl cellulose (HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetaamethylbutyl)-phenol polymer with ethylene oxide and formaldehyde (also known as tyloxapol, superione, and triton), poloxamers, poloxamnines, a charged phospholipid such as dimyristoyl phophatidyl glycerol, dioctylsulfosuccinate (DOSS); Tetronic® 1508, dialkylesters of sodium sulfosuccinic acid, Duponol P, Tritons X-200, Crodestas F-110, p-isononylphenoxypoly-(glycidol), Crodestas SL-40 (Croda, Inc.); and SA9OHCO, which is $C_{18}H_{37}CH_2(CON(CH_3)-CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucarmide; n-octyl-β-D-glucopyranoside; octyl β-D-thioglucopyranoside;

and the like. Most of these surfactants are known pharmaceutical excipients and are described in detail in the Handbook of Pharmaceutical Excipients, published jointly by the American Pharmaceutical Association and The Pharmaceutical Society of Great Britain (The Pharmaceutical Press, 1986), specifically incorporated by reference for such disclosure.

The hydrophobic, water-insoluble and water-indispersible polymer or copolymer may be chosen from biocompatible and biodegradable polymers, for example lactic or glycolic acid polymers and copolymers thereof, or polylactic/polyethylene (or polypropylene) oxide copolymers, preferably with molecular weights of between 1000 and 200,000, polyhydroxybutyric acid polymers, polylactones of fatty acids containing at least 12 carbon atoms, or polyanhydrides.

The nanoparticles may be obtained by coacervation, or by the technique of evaporation of solvent, from an aqueous dispersion or solution of phospholipids and of an oleic acid salt into which is added an immiscible organic phase comprising the active principle and the hydrophobic, water-insoluble and water-indispersible polymer or copolymer. The mixture is pre-emulsified and then subjected to homogenization and evaporation of the organic solvent to obtain an aqueous suspension of very small-sized nanoparticles.

A variety of methods are optionally employed to fabricate the antimicrobial agent nanoparticles that are within the scope of the embodiments. These methods include vaporization methods, such as free jet expansion, laser vaporization, spark erosion, electro explosion and chemical vapor deposition; physical methods involving mechanical attrition (e.g., "pearlmilling" technology, Elan Nanosystems), super critical CO2 and interfacial deposition following solvent displacement. In one embodiment, the solvent displacement method is used. The size of nanoparticles produced by this method is sensitive to the concentration of polymer in the organic solvent; the rate of mixing; and to the surfactant employed in the process. Continuous flow mixers provide the necessary turbulence to ensure small particle size. One type of continuous flow mixing device that is optionally used to prepare nanoparticles has been described (Hansen et al J Phys Chem 92, 2189-96, 1988). In other embodiments, ultrasonic devices, flow through homogenizers or supercritical CO2 devices may be used to prepare nanoparticles.

If suitable nanoparticle homogeneity is not obtained on direct synthesis, then size-exclusion chromatography is used to produce highly uniform drug-containing particles that are freed of other components involved in their fabrication. Size-exclusion chromatography (SEC) techniques, such as gel-filtration chromatography, is used to separate particle-bound antimicrobial agent or other pharmaceutical compound from free antimicrobial agent or other pharmaceutical compound, or to select a suitable size range of antimicrobial agent-containing nanoparticles. Various SEC media, such as Superdex 200, Superose 6, Sephacryl 1000 are commercially available and are employed for the size-based fractionation of such mixtures. Additionally, nanoparticles are optionally purified by centrifugation, membrane filtration and by use of other molecular sieving devices, crosslinked gels/materials and membranes.

Auris-Acceptable Cyclodextrin and Other Stabilizing Formulations

In a specific embodiment, the auris-acceptable formulations alternatively comprises a cyclodextrin. Cyclodextrins are cyclic oligosaccharides containing 6, 7, or 8 glucopyranose units, referred to as α-cyclodextrin, β-cyclodextrin, or γ-cyclodextrin respectively. Cyclodextrins have a hydrophilic exterior, which enhances water-soluble, and a hydrophobic interior which forms a cavity. In an aqueous environment, hydrophobic portions of other molecules often enter the hydrophobic cavity of cyclodextrin to form inclusion compounds. Additionally, cyclodextrins are also capable of other types of nonbonding interactions with molecules that are not inside the hydrophobic cavity. Cyclodextrins have three free hydroxyl groups for each glucopyranose unit, or 18 hydroxyl groups on α-cyclodextrin, 21 hydroxyl groups on β-cyclodextrin, and 24 hydroxyl groups on γ-cyclodextrin. One or more of these hydroxyl groups can be reacted with any of a number of reagents to form a large variety of cyclodextrin derivatives, including hydroxypropyl ethers, sulfonates, and sulfoalkylethers. Shown below is the structure of β-cyclodextrin and the hydroxypropyl-β-cyclodextrin (HPβCD).

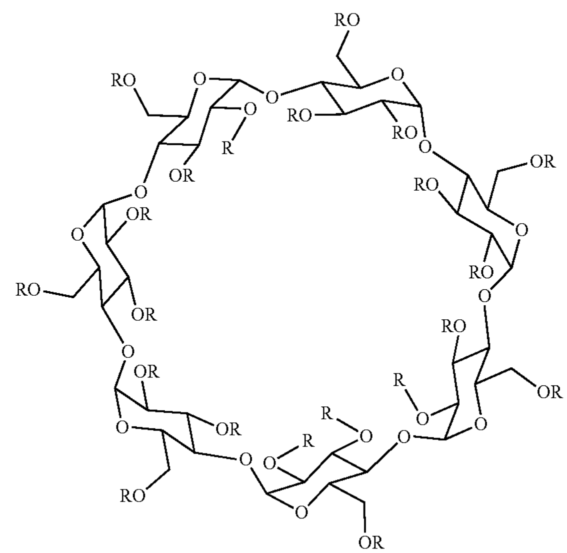

R = H
β-cyclodextrin
R = $CH_2CH(OH)CH_3$
hydroxypropyl β-cyclodextrin

In some embodiments, the use of cyclodextrins in the pharmaceutical compositions described herein improves the solubility of the drug. Inclusion compounds are involved in many cases of enhanced solubility; however other interactions between cyclodextrins and insoluble compounds also improves solubility. Hydroxypropyl-β-cyclodextrin (HPβCD) is commercially available as a pyrogen free product. It is a nonhygroscopic white powder that readily dissolves in water. HPβCD is thermally stable and does not degrade at neutral pH. Thus, cyclodextrins improve the solubility of a therapeutic agent in a composition or formulation. Accordingly, in some embodiments, cyclodextrins are included to increase the solubility of the auris-acceptable antimicrobial agents within the formulations described herein. In other embodiments, cyclodextrins in addition serve as controlled release excipients within the formulations described herein.

By way of example only, cyclodextrin derivatives for use include α-cyclodextrin, β-cyclodextrin, γ-cyclodextrin, hydroxyethyl β-cyclodextrin, hydroxypropyl γ-cyclodextrin, sulfated β-cyclodextrin, sulfated α-cyclodextrin, sulfobutyl ether β-cyclodextrin.

The concentration of the cyclodextrin used in the compositions and methods disclosed herein varies according to the physiochemical properties, pharmacokinetic properties, side effect or adverse events, formulation considerations, or other factors associated with the therapeutically active agent, or a salt or prodrug thereof, or with the properties of other excipients in the composition. Thus, in certain circumstances, the concentration or amount of cyclodextrin used in accordance with the compositions and methods disclosed herein will vary, depending on the need. When used, the amount of cyclodextrins needed to increase solubility of the antimicrobial agent and/or function as a controlled release excipient in any of the formulations described herein is selected using the principles, examples, and teachings described herein.

Other stabilizers that are useful in the auris-acceptable formulations disclosed herein include, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. In further embodiments, the chosen stabilizer changes the hydrophobicity of the formulation (e.g., oleic acid, waxes), or improves the mixing of various components in the formulation (e.g., ethanol), controls the moisture level in the formula (e.g., PVP or polyvinyl pyrrolidone), controls the mobility of the phase (substances with melting points higher than room temperature such as long chain fatty acids, alcohols, esters, ethers, amides etc. or mixtures thereof; waxes), and/or improves the compatibility of the formula with encapsulating materials (e.g., oleic acid or wax). In another embodiment some of these stabilizers are used as solvents/co-solvents (e.g., ethanol). In other embodiments, stabilizers are present in sufficient amounts to inhibit the degradation of the antimicrobial agent. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

Additional useful antimicrobial agent auris-acceptable formulations include one or more anti-aggregation additives to enhance stability of antimicrobial agent formulations by reducing the rate of protein aggregation. The anti-aggregation additive selected depends upon the nature of the conditions to which the antimicrobial agents, for example antimicrobial agent antibodies are exposed. For example, certain formulations undergoing agitation and thermal stress require a different anti-aggregation additive than a formulation undergoing lyophilization and reconstitution. Useful anti-aggregation additives include, by way of example only, urea, guanidinium chloride, simple amino acids such as glycine or arginine, sugars, polyalcohols, polysorbates, polymers such as polyethylene glycol and dextrans, alkyl saccharides, such as alkyl glycoside, and surfactants.

Other useful formulations optionally include one or more auris-acceptable antioxidants to enhance chemical stability where required. Suitable antioxidants include, by way of example only, ascorbic acid, methionine, sodium thiosulfate and sodium metabisulfite. In one embodiment, antioxidants are selected from metal chelating agents, thiol containing compounds and other general stabilizing agents.

Still other useful compositions include one or more auris-acceptable surfactants to enhance physical stability or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In some embodiments, the auris-acceptable pharmaceutical formulations described herein are stable with respect to compound degradation over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 3 months, at least about 4 months, at least about 5 months, or at least about 6 months. In other embodiments, the formulations described herein are stable with respect to compound degradation over a period of at least about 1 week. Also described herein are formulations that are stable with respect to compound degradation over a period of at least about 1 month.

In other embodiments, an additional surfactant (co-surfactant) and/or buffering agent is combined with one or more of the pharmaceutically acceptable vehicles previously described herein so that the surfactant and/or buffering agent maintains the product at an optimal pH for stability. Suitable co-surfactants include, but are not limited to: a) natural and synthetic lipophilic agents, e.g., phospholipids, cholesterol, and cholesterol fatty acid esters and derivatives thereof; b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij ° 700, ascorbyl-6-palmitate, stearylamine, sodium lauryl sulfate, polyoxethyleneglycerol triiricinoleate, and any combinations or mixtures thereof; c) anionic surfactants include, but are not limited to, calcium carboxymethylcellulose, sodium carboxymethylcellulose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof; and d) cationic surfactants such as cetyltrimethylammonium bromide, and lauryldimethylbenzyl-ammonium chloride.

In a further embodiment, when one or more co-surfactants are utilized in the auris-acceptable formulations of the present disclosure, they are combined, e.g., with a pharmaceutically acceptable vehicle and is present in the final formulation, e.g., in an amount ranging from about 0.1% to about 20%, from about 0.5% to about 10%.

In one embodiment, the surfactant has an HLB value of 0 to 20. In additional embodiments, the surfactant has an HLB value of 0 to 3, of 4 to 6, of 7 to 9, of 8 to 18, of 13 to 15, of 10 to 18.

In one embodiment, diluents are also used to stabilize the antimicrobial agent or other pharmaceutical compounds because they provide a more stable environment. Salts dissolved in buffered solutions (which also can provide pH control or maintenance) are utilized as diluents, including, but not limited to a phosphate buffered saline solution. In other embodiments, the gel formulation is isotonic with the endolymph or the perilymph: depending on the portion of the cochlea that the antimicrobial agent formulation is targeted. Isotonic formulations are provided by the addition of a tonicity agent. Suitable tonicity agents include, but are not limited to any pharmaceutically acceptable sugar, salt or any combinations or mixtures thereof, such as, but not limited to dextrose and sodium chloride. In further embodiments, the tonicity agents are present in an amount from about 100 mOsm/kg to about 500 mOsm/kg. In some embodiments, the tonicity agent is present in an amount from about 200 mOsm/kg to about 400 mOsm/kg, from about 280 mOsm/kg to about 320 mOsm/kg. The amount of tonicity agents will depend on the target structure of the pharmaceutical formulation, as described herein.

Useful tonicity compositions also include one or more salts in an amount required to bring osmolality of the composition into an acceptable range for the perilymph or the endolymph. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the auris-acceptable gel formulations disclosed herein alternatively or additionally contains preservatives to prevent microbial growth. Suitable auris-acceptable preservatives for use in the enhanced viscosity formulations described herein include, but are not limited to benzoic acid, boric acid, p-hydroxybenzoates, alcohols, quarternary compounds, stabilized chlorine dioxide, mercurials, such as merfen and thiomersal, mixtures of the foregoing and the like.

In a further embodiment, the preservative is, by way of example only, an antimicrobial agent, within the auris-acceptable formulations presented herein. In one embodiment, the formulation includes a preservative such as by way of example only, methyl paraben, sodium bisulfite, sodium thiosulfate, ascorbate, chorobutanol, thimerosal, parabens, benzyl alcohol, phenylethanol and others. In another embodiment, the methyl paraben is at a concentration of about 0.05% to about 1.0%, about 0.1% to about 0.2%. In a further embodiment, the gel is prepared by mixing water, methylparaben, hydroxyethylcellulose and sodium citrate. In a further embodiment, the gel is prepared by mixing water, methylparaben, hydroxyethylcellulose and sodium acetate. In a further embodiment, the mixture is sterilized by autoclaving at 120° C. for about 20 minutes, and tested for pH, methylparaben concentration and viscosity before mixing with the appropriate amount of the antimicrobial agent disclosed herein.

Suitable auris-acceptable water soluble preservatives which are employed in the drug delivery vehicle include sodium bisulfite, sodium thiosulfate, ascorbate, chorobutanol, thimerosal, parabens, benzyl alcohol, Butylated hydroxytoluene (BHT), phenylethanol and others. These agents are present, generally, in amounts of about 0.001% to about 5% by weight or, in the amount of about 0.01 to about 2% by weight. In some embodiments, auris-compatible formulations described herein are free of preservatives.

Round Window Membrane Penetration Enhancers

In another embodiment, the formulation further comprises one or more round window membrane penetration enhancers. Penetration across the round window membrane is enhanced by the presence of round window membrane penetration enhancers. Round window membrane penetration enhancers are chemical entities that facilitate transport of coadministered substances across the round window membrane. Round window membrane penetration enhancers are grouped according to chemical structure. Surfactants, both ionic and non-ionic, such as sodium lauryl sulfate, sodium laurate, polyoxyethylene-20-cetyl ether, laureth-9, sodium dodecylsulfate, dioctyl sodium sulfosuccinate, polyoxyethylene-9-lauryl ether (PLE), Tween® 80, nonylphenoxypolyethylene (NP-POE), polysorbates and the like, function as round window membrane penetration enhancers. Bile salts (such as sodium glycocholate, sodium deoxycholate, sodium taurocholate, sodium taurodihydrofusidate, sodium glycodihydrofusidate and the like), fatty acids and derivatives (such as oleic acid, caprylic acid, mono- and di-glycerides, lauric acids, acylcholines, caprylic acids, acylcarnitines, sodium caprates and the like), chelating agents (such as EDTA, citric acid, salicylates and the like), sulfoxides (such as dimethyl sulfoxide (DMSO), decylmethyl sulfoxide and the like), and alcohols (such as ethanol, isopropanol, glycerol, propanediol and the like) also function as round window membrane penetration enhancers.

In some embodiments, the auris acceptable penetration enhancer is a surfactant comprising an alkyl-glycoside wherein the alkyl glycoside is tetradecyl-β-D-maltoside. In some embodiments, the auris acceptable penetration enhancer is a surfactant comprising an alkyl-glycoside wherein the alkyl glycoside is dodecyl-maltoside. In certain instances, the penetration enhancing agent is a hyaluronidase. In certain instances, a hyaluronidase is a human or bovine hyaluronidase. In some instances, a hyaluronidase is a human hyaluronidase (e.g., hyaluronidase found in human sperm, PH20 (Halozyme), Hyelenex® (Baxter International, Inc.)). In some instances, a hyaluronidase is a bovine hyaluronidase (e.g., bovine testicular hyaluronidase, Amphadase® (Amphastar Pharmaceuticals), Hydase® (PrimaPharm, Inc). In some instances, a hyluronidase is an ovine hyaluronidase, Vitrase® (ISTA Pharmaceuticals). In certain instances, a hyaluronidase described herein is a recombinant hyaluronidase. In some instances, a hyaluronidase described herein is a humanized recombinant hyaluronidase. In some instances, a hyaluronidase described herein is a pegylated hyaluronidase (e.g., PEGPH20 (Halozyme)). In addition, the peptide-like penetration enhancers described in U.S. Pat. Nos. 7,151,191, 6,221,367 and 5,714, 167, herein incorporated by references for such disclosure, are contemplated as an additional embodiment. These penetration enhancers are amino-acid and peptide derivatives and enable drug absorption by passive transcellular diffusion without affecting the integrity of membranes or intercellular tight junctions.

Round Window Membrane Permeable Liposomes

Liposomes or lipid particles may also be employed to encapsulate the antimicrobial agent formulations or compositions. Phospholipids that are gently dispersed in an aqueous medium form multilayer vesicles with areas of entrapped aqueous media separating the lipid layers. Sonication, or turbulent agitation, of these multilayer vesicles results in the formation of single layer vesicles, commonly referred to as liposomes, with sizes of about 10-1000 nm. These liposomes have many advantages as antimicrobial agents or other pharmaceutical agent carriers. They are biologically inert, biodegradable, non-toxic and non-antigenic. Liposomes are formed in various sizes and with varying compositions and surface properties. Additionally, they are able to entrap a wide variety of agents and release the agent at the site of liposome collapse.

Suitable phospholipids for use in auris-acceptable liposomes here are, for example, phosphatidyl cholines, ethanolamines and serines, sphingomyelins, cardiolipins, plasmalogens, phosphatidic acids and cerebrosides, in particular those which are soluble together with the antimicrobial agents herein in non-toxic, pharmaceutically acceptable organic solvents. Preferred phospholipids are, for example, phosphatidyl choline, phosphatidyl ethanolmine, phosphatidyl serine, phosphatidyl inositol, lysophosphatidyl choline, phosphatidyl glycerol and the like, and mixtures thereof especially lecithin, e.g. soya lecithin. The amount of phospholipid used in the present formulation range from about 10 to about 30%, preferably from about 15 to about 25% and in particular is about 20%.

Lipophilic additives may be employed advantageously to modify selectively the characteristics of the liposomes. Examples of such additives include by way of example only, stearylamine, phosphatidic acid, tocopherol, cholesterol, cholesterol hemisuccinate and lanolin extracts. The amount of lipophilic additive used range from 0.5 to 8%, preferably from 1.5 to 4% and in particular is about 2%. Generally, the ratio of the amount of lipophilic additive to the amount of phospholipid ranges from about 1:8 to about 1:12 and in particular is about 1:10. Said phospholipid, lipophilic additive and the antimicrobial agent and other pharmaceutical compounds are employed in conjunction with a non-toxic, pharmaceutically acceptable organic solvent system which dissolve said ingredients. Said solvent system not only must dissolve the antimicrobial agent completely, but it also has to allow the formulation of stable single bilayered liposomes. The solvent system comprises dimethylisosorbide and tetraglycol (glycofurol, tetrahydrofurfuryl alcohol polyethylene glycol ether) in an amount of about 8 to about 30%. In said solvent system, the ratio of the amount of dimethylisosorbide to the amount of tetraglycol range from about 2:1 to about 1:3, in particular from about 1:1 to about 1:2.5 and preferably is about 1:2. The amount of tetraglycol in the final composition thus vary from 5 to 20%, in particular from 5 to 15% and preferably is approximately 10%. The amount of dimethylisosorbide in the final composition thus range from 3 to 10%, in particular from 3 to 7% and preferably is approximately 5%.

The term "organic component" as used hereinafter refers to mixtures comprising said phospholipid, lipophilic additives and organic solvents. The antimicrobial agent may be dissolved in the organic component, or other means to maintain full activity of the agent. The amount of antimicrobial agent in the final formulation may range from 0.1 to 5.0%. In addition, other ingredients such as antioxidants may be added to the organic component. Examples include tocopherol, butylated hydroxyanisole, butylated hydroxytoluene, ascorbyl palmitate, ascorbyl oleate and the like.

Liposomal formulations are alternatively prepared, for antimicrobial agents or other pharmaceutical agents that are moderately heat-resistant, by (a) heating the phospholipid and the organic solvent system to about 60-80° C. in a vessel, dissolving the active ingredient, then adding any additional formulating agents, and stirring the mixture until complete dissolution is obtained; (b) heating the aqueous solution to 90-95° C. in a second vessel and dissolving the preservatives therein, allowing the mixture to cool and then adding the remainder of the auxiliary formulating agents and the remainder of the water, and stirring the mixture until complete dissolution is obtained; thus preparing the aqueous component; (c) transferring the organic phase directly into the aqueous component, while homogenizing the combination with a high performance mixing apparatus, for example, a high-shear mixer; and (d) adding a viscosity enhancing agent to the resulting mixture while further homogenizing. The aqueous component is optionally placed in a suitable vessel which is equipped with a homogenizer and homogenization is effected by creating turbulence during the injection of the organic component. Any mixing means or homogenizer which exerts high shear forces on the mixture may be employed. Generally, a mixer capable of speeds from about 1,500 to 20,000 rpm, in particular from about 3,000 to about 6,000 rpm may be employed. Suitable viscosity enhancing agents for use in process step (d) are for example, xanthan gum, hydroxypropyl cellulose, hydroxypropyl methylcellulose or mixtures thereof. The amount of viscosity enhancing agent depends on the nature and the concentration of the other ingredients and in general ranges from about 0.5 to 2.0%, or approximately 1.5%. In order to prevent degradation of the materials used during the preparation of the liposomal formulation, it is advantageous to purge all solutions with an inert gas such as nitrogen or argon, and to conduct all steps under an inert atmosphere. Liposomes prepared by the above described method usually contain most of the active ingredient bound in the lipid bilayer and separation of the liposomes from unencapsulated material is not required.

In other embodiments, the auris-acceptable formulations, including gel formulations and viscosity-enhanced formulations, further include excipients, other medicinal or pharmaceutical agents, carriers, adjuvants, such as preserving, stabilizing, wetting or emulsifying agents, solution promoters, salts, solubilizers, an antifoaming agent, an antioxidant, a dispersing agent, a wetting agent, a surfactant, and combinations thereof.

Suitable carriers for use in an auris-acceptable formulation described herein include, but are not limited to, any pharmaceutically acceptable solvent compatible with the targeted auris structure's physiological environment. In other embodiments, the base is a combination of a pharmaceutically acceptable surfactant and solvent.

In some embodiments, other excipients include, sodium stearyl fumarate, diethanolamine cetyl sulfate, isostearate, polyethoxylated castor oil, nonoxyl 10, octoxynol 9, sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithin pharmaceutical acceptable salts thereof and combinations or mixtures thereof.

In other embodiments, the carrier is a polysorbate. Polysorbates are nonionic surfactants of sorbitan esters. Polysorbates useful in the present disclosure include, but are not limited to polysorbate 20, polysorbate 40, polysorbate 60, polysorbate 80 (Tween 80) and any combinations or mixtures thereof. In further embodiments, polysorbate 80 is utilized as the pharmaceutically acceptable carrier.

In one embodiment, water-soluble glycerin-based auris-acceptable enhanced viscosity formulations utilized in the preparation of pharmaceutical delivery vehicles comprise at least one antimicrobial agent containing at least about 0.1% of the water-soluble glycerin compound or more. In some embodiments, the percentage of antimicrobial agent is varied between about 1% and about 95%, between about 5% and about 80%, between about 10% and about 60% or more of the weight or volume of the total pharmaceutical formulation. In some embodiments, the amount of the compound(s) in each therapeutically useful antimicrobial agent formulation is prepared in such a way that a suitable dosage will be obtained in any given unit dose of the compound. Factors such as solubility, bioavailability, biological half-life, route of administration, product shelf life, as well as other pharmacological considerations are contemplated herein.

If desired, the auris-acceptable pharmaceutical gels also contain co-solvents, preservatives, cosolvents, ionic strength and osmolality adjustors and other excipients in addition to buffering agents. Suitable auris-acceptable water soluble buffering agents are alkali or alkaline earth metal carbonates, phosphates, bicarbonates, citrates, borates, acetates, succinates and the like, such as sodium phosphate, citrate, borate, acetate, bicarbonate, carbonate and tromethamine (TRIS). These agents are present in amounts sufficient to maintain the pH of the system at 7.4±0.2 and preferably, 7.4. As such, the buffering agent is as much as 5% on a weight basis of the total composition.

Cosolvents are used to enhance antimicrobial agent solubility, however, some antimicrobial agents or other pharmaceutical compounds are insoluble. These are often suspended in the polymer vehicle with the aid of suitable suspending or viscosity enhancing agents.

Examples of therapeutically acceptable otic formulations:

effects that may arise from the use of specific therapeutic agents or excipients, diluents or carriers.

Modes of Treatment

Dosing Methods and Schedules

Drugs delivered to the inner ear have been administered systemically via oral, intravenous or intramuscular routes. However, systemic administration for pathologies local to the inner ear increases the likelihood of systemic toxicities and adverse side effects and creates a non-productive distribution of drug in which high levels of drug are found in the serum and correspondingly lower levels are found at the inner ear.

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the antimicrobial agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In one embodiment the delivery system is a syringe and needle apparatus that is capable of piercing the tympanic membrane and directly accessing the round window membrane or crista fenestrae cochleae of the auris interna. In some embodiments, the needle on the syringe is wider than a 18 gauge needle. In another embodiment, the needle gauge is from 18 gauge to 31 gauge. In a further embodiment, the needle gauge is from 25 gauge to 30 gauge. Depending upon the thickness or viscosity of the antimicrobial agent com-

| Example Formulation | Example Characteristics |
|---|---|
| Chitosan glycerophosphate (CGP) | tunable degradation of matrix in vitro<br>tunable TACE inhibitor release in vitro: e.g., ~50% of drug released after 24 hrs<br>biodegradable<br>compatible with drug delivery to the inner ear<br>suitable for macromolecules and hydrophobic drugs |
| PEG-PLGA-PEG triblock polymers | tunable high stability: e.g., maintains mechanical integrity >1 month in vitro<br>tunable fast release of hydrophilic drugs: e.g., ~50% of drug released after 24 hrs, and remainder released over ~5 days<br>tunable slow release of hydrophobic drugs: e.g., ~80% released after 8 weeks<br>biodegradable<br>subcutaneous injection of solution: e.g., gel forms within seconds and is intact after 1 month |
| PEO-PPO-PEO triblock copolymers (e.g., Pluronic or Poloxameres) (e.g., F127) | Tunable sol-gel transition temperature: e.g., decreases with increasing F127 concentration |
| Chitosan glycerophosphate with drug-loaded liposomes | CGP formulation tolerates liposomes: e.g., up to 15 uM/ml liposomes.<br>liposomes tunably reduce drug release time (e.g., up to 2 weeks in vitro).<br>increase in liposome diameter optionally reduces drug release kinetics (e.g., liposome size between 100 and 300 nm)<br>release parameters are controlled by changing composition of liposomes |

The formulations disclosed herein alternatively encompass an otoprotectant agent in addition to the at least one active agent and/or excipients, including but not limited to such agents as antioxidants, alpha lipoic acid, calcium, fosfomycin or iron chelators, to counteract potential ototoxic positions or formulations, the gauge level of the syringe or hypodermic needle may be varied accordingly. In another embodiment, the internal diameter of the needle can be increased by reducing the wall thickness of the needle (commonly referred as thin wall or extra thin wall needles)

to reduce the possibility of needle clogging while maintaining an adequate needle gauge.

In another embodiment, the needle is a hypodermic needle used for instant delivery of the gel formulation. The hypodermic needle may be a single use needle or a disposable needle. In some embodiments, a syringe may be used for delivery of the pharmaceutically acceptable gel-based antimicrobial agent-containing compositions as disclosed herein wherein the syringe has a press-fit (Luer) or twist-on (Luer-lock) fitting. In one embodiment, the syringe is a hypodermic syringe. In another embodiment, the syringe is made of plastic or glass. In yet another embodiment, the hypodermic syringe is a single use syringe. In a further embodiment, the glass syringe is capable of being sterilized. In yet a further embodiment, the sterilization occurs through an autoclave. In another embodiment, the syringe comprises a cylindrical syringe body wherein the gel formulation is stored before use. In other embodiments, the syringe comprises a cylindrical syringe body wherein the antimicrobial agent pharmaceutically acceptable gel-based compositions as disclosed herein is stored before use which conveniently allows for mixing with a suitable pharmaceutically acceptable buffer. In other embodiments, the syringe may contain other excipients, stabilizers, suspending agents, diluents or a combination thereof to stabilize or otherwise stably store the antimicrobial agent or other pharmaceutical compounds contained therein.

In some embodiments, the syringe comprises a cylindrical syringe body wherein the body is compartmentalized in that each compartment is able to store at least one component of the auris-acceptable antimicrobial agent gel formulation. In a further embodiment, the syringe having a compartmentalized body allows for mixing of the components prior to injection into the auris media or auris interna. In other embodiments, the delivery system comprises multiple syringes, each syringe of the multiple syringes contains at least one component of the gel formulation such that each component is pre-mixed prior to injection or is mixed subsequent to injection. In a further embodiment, the syringes disclosed herein comprise at least one reservoir wherein the at least one reservoir comprises an antimicrobial agent, or a pharmaceutically acceptable buffer, or a viscosity enhancing agent, such as a gelling agent or a combination thereof. Commercially available injection devices are optionally employed in their simplest form as ready-to-use plastic syringes with a syringe barrel, needle assembly with a needle, plunger with a plunger rod, and holding flange, to perform an intratympanic injection.

In some embodiments, the delivery device is an apparatus designed for administration of therapeutic agents to the middle and/or inner ear. By way of example only: GYRUS Medical Gmbh offers micro-otoscopes for visualization of and drug delivery to the round window niche; Arenberg has described a medical treatment device to deliver fluids to inner ear structures in U.S. Pat. Nos. 5,421,818; 5,474,529; and 5,476,446, each of which is incorporated by reference herein for such disclosure. U.S. patent application Ser. No. 08/874,208, which is incorporated herein by reference for such disclosure, describes a surgical method for implanting a fluid transfer conduit to deliver therapeutic agents to the inner ear. U.S. Patent Application Publication 2007/0167918, which is incorporated herein by reference for such disclosure, further describes a combined otic aspirator and medication dispenser for intratympanic fluid sampling and medicament application.

The auris-acceptable compositions or formulations containing the antimicrobial agent compound(s) described herein are administered for prophylactic and/or therapeutic treatments. In therapeutic applications, the antimicrobial agent compositions are administered to a patient already suffering from an autoimmune disease, condition or disorder, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician.

Frequency of Administration

In some embodiments, a composition disclosed herein is administered to an individual in need thereof once. In some embodiments, a composition disclosed herein is administered to an individual in need thereof more than once. In some embodiments, a first administration of a composition disclosed herein is followed by a second administration of a composition disclosed herein. In some embodiments, a first administration of a composition disclosed herein is followed by a second and third administration of a composition disclosed herein. In some embodiments, a first administration of a composition disclosed herein is followed by a second, third, and fourth administration of a composition disclosed herein. In some embodiments, a first administration of a composition disclosed herein is followed by a second, third, fourth, and fifth administration of a composition disclosed herein. In some embodiments, a first administration of a composition disclosed herein is followed by a drug holiday.

The number of times a composition is administered to an individual in need thereof depends on the discretion of a medical professional, the disorder, the severity of the disorder, and the individuals's response to the formulation. In some embodiments, a composition disclosed herein is administered once to an individual in need thereof with a mild acute condition. In some embodiments, a composition disclosed herein is administered more than once to an individual in need thereof with a moderate or severe acute condition. In the case wherein the patient's condition does not improve, upon the doctor's discretion the administration of an antimicrobial may be administered chronically, that is, for an extended period of time, including throughout the duration of the patient's life in order to ameliorate or otherwise control or limit the symptoms of the patient's disease or condition.

In the case wherein the patient's condition does not improve, upon the doctor's discretion the administration of the antimicrobial agent compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the antimicrobial agent compounds may be given continuously; alternatively, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's otic conditions has occurred, a maintenance antimicrobial agent dose is administered if necessary. Subsequently, the dosage or the frequency of administration, or both, is optionally reduced, as a function of the symptoms, to a level at which the improved disease, disorder or condition is retained. In certain embodiments, patients require intermittent treatment on a long-term basis upon any recurrence of symptoms.

The amount of antimicrobial agent that will correspond to such an amount will vary depending upon factors such as the particular compound, disease condition and its severity, according to the particular circumstances surrounding the case, including, e.g., the specific antimicrobial agent being administered, the route of administration, the autoimmune condition being treated, the target area being treated, and the subject or host being treated. In general, however, doses employed for adult human treatment will typically be in the range of 0.02-50 mg per administration, preferably 1-15 mg per administration. The desired dose is presented in a single dose or as divided doses administered simultaneously (or over a short period of time) or at appropriate intervals.

In some embodiments, the initial administration is a particular antimicrobial agent and the subsequent administration a different formulation or antimicrobial agent.

Pharmacokinetics of Controlled Release Formulations

In one embodiment, the formulations disclosed herein additionally provides an immediate release of an antimicrobial agent from the composition, or within 1 minute, or within 5 minutes, or within 10 minutes, or within 15 minutes, or within 30 minutes, or within 60 minutes or within 90 minutes. In other embodiments, a therapeutically effective amount of at least one antimicrobial agent is released from the composition immediately, or within 1 minute, or within 5 minutes, or within 10 minutes, or within 15 minutes, or within 30 minutes, or within 60 minutes or within 90 minutes. In certain embodiments the composition comprises an auris-pharmaceutically acceptable gel formulation providing immediate release of at least one antimicrobial agent. Additional embodiments of the formulation may also include an agent that enhances the viscosity of the formulations included herein.

In other or further embodiments, the formulation provides an extended release formulation of at least one antimicrobial agent. In certain embodiments, diffusion of at least one antimicrobial agent from the formulation occurs for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year. In other embodiments, a therapeutically effective amount of at least one antimicrobial agent is released from the formulation for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year.

In other embodiments, the formulation provides both an immediate release and an extended release formulation of an antimicrobial agent. In yet other embodiments, the formulation contains a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations. In a further embodiment the formulation provides an immediate release of a first antimicrobial agent and an extended release of a second antimicrobial agent or other therapeutic agent. In yet other embodiments, the formulation provides an immediate release and extended release formulation of at least one antimicrobial agent, and at least one therapeutic agent. In some embodiments, the formulation provides a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations of a first antimicrobial agent and second therapeutic agent, respectively.

In a specific embodiment the formulation provides a therapeutically effective amount of at least one antimicrobial agent at the site of disease with essentially no systemic exposure. In an additional embodiment the formulation provides a therapeutically effective amount of at least one antimicrobial agent at the site of disease with essentially no detectable systemic exposure. In other embodiments, the formulation provides a therapeutically effective amount of at least one antimicrobial agent at the site of disease with little or no detectable systemic exposure.

The combination of immediate release, delayed release and/or extended release antimicrobial agent compositions or formulations may be combined with other pharmaceutical agents, as well as the excipients, diluents, stabilizers, tonicity agents and other components disclosed herein. As such, depending upon the antimicrobial agent used, the thickness or viscosity desired, or the mode of delivery chosen, alternative aspects of the embodiments disclosed herein are combined with the immediate release, delayed release and/or extended release embodiments accordingly.

In certain embodiments, the pharmacokinetics of the antimicrobial agent formulations described herein are determined by injecting the formulation on or near the round window membrane of a test animal (including by way of example, a guinea pig or a chinchilla). At a determined period of time (e.g., 6 hours, 12 hours, 1 day, 2 days, 3 days, 4 days, 5 days, 6 days, and 7 days for testing the pharmacokinetics of a formulation over a 1 week period), the test animal is euthanized and a 5 mL sample of the perilymph fluid is tested. The inner ear removed and tested for the presence of the antimicrobial agent. As needed, the level of antimicrobial agent is measured in other organs. In addition, the systemic level of the antimicrobial agent is measured by withdrawing a blood sample from the test animal. In order to determine whether the formulation impedes hearing, the hearing of the test animal is optionally tested.

Alternatively, an inner ear is provided (as removed from a test animal) and the migration of the antimicrobial agent is measured. As yet another alternative, an in vitro model of a round window membrane is provided and the migration of the antimicrobial agent is measured.

Kits/Articles of Manufacture

The disclosure also provides kits for preventing, treating or ameliorating the symptoms of a disease or disorder in a mammal. Such kits generally will comprise one or more of the antimicrobial agent controlled-release compositions or devices disclosed herein, and instructions for using the kit. The disclosure also contemplates the use of one or more of the antimicrobial agent controlled-release compositions, in the manufacture of medicaments for treating, abating, reducing, or ameliorating the symptoms of a disease, dysfunction, or disorder in a mammal, such as a human that has, is suspected of having, or at risk for developing an inner ear disorder.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products are also presented herein. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of antimicrobial agent formulations compositions provided herein are contemplated as are a variety of treatments for any disease, disorder, or condition that would benefit by controlled release administration of an antimicrobial agent to the inner ear.

In some embodiments, a kit includes one or more additional containers, each with one or more of various materials (such as reagents, optionally in concentrated form, and/or devices) desirable from a commercial and user standpoint for use of a formulation described herein. Non-limiting examples of such materials include, but are not limited to, buffers, diluents, filters, needles, syringes; carrier, package, container, vial and/or tube labels listing contents and/or instructions for use and package inserts with instructions for use. A set of instructions is optionally included. In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the pharmaceutical compositions are presented in a pack or dispenser device which contains one or more unit dosage forms containing a compound provided herein. In another embodiment, the pack for example contains metal or plastic foil, such as a blister pack. In a further embodiment, the pack or dispenser device is accompanied by instructions for administration. In yet a further embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

EXAMPLES

Example 1—Preparation of an Amoxicillin Thermoreversible Gel Formulation

| Ingredient | Quantity (mg/g of formulation) |
|---|---|
| Amoxicillin | 5.0 |
| Methylparaben | 1.0 |
| HPMC | 15.0 |
| Poloxamer 407 | 175.0 |
| TRIS HCl buffer (0.1M) | 804.0 |

A 10-g batch of gel formulation containing 0.5% of the antimicrobial agent amoxicillin is prepared by suspending 1.75 g of Poloxamer 407 (BASF Corp.) in 5.00 g of TRIS HCl buffer (0.1 M) and the components are mixed under agitation overnight at 4° C. to ensure complete dissolution. The hydroxypropyl methylcellulose (150.0 mg), methylparaben (10 mg) and additional TRIS HCl buffer (0.1 M) (3.04 g) are added and further stirring allowed until complete dissolution is observed. Amoxicillin (50 mg) is added and mixed in order to solubilize. The mixture is maintained below room temperature until use.

Example 2—Preparation of a Neomycin Mucoadhesive, Thermoreversible Gel Formulation Containing an Otoprotectant

| Ingredient | Quantity (mg/g of formulation) |
|---|---|
| Neomycin | 6.0 |
| Methylparaben | 1.0 |
| HPMC | 15.0 |
| Carbopol 934P | 2.0 |
| Poloxamer 407 | 180.0 |
| Deferoxamine | 5.0 |
| TRIS HCl buffer (0.1M) | 791.0 |

A 10-g batch of a mucoadhesive, gel formulation containing 0.6% of the antimicrobial agent neomycin is prepared by suspending 20.0 mg of Carbopol 934P and 1.80 g of Poloxamer 407 (BASF Corp.) in 5.00 g of TRIS HCl buffer (0.1 M) and the components are mixed under agitation overnight at 4° C. to ensure complete dissolution. The hydroxypropyl methylcellulose (150.0 mg), methylparaben (10 mg) and additional TRIS HCl buffer (0.1 M) (2.91 g) are added and further stirring allowed until complete dissolution is observed. The neomycin (60 mg) and deferoxamine (50 mg) are added and mixed in order to solubilize. The mixture is maintained below room temperature until use.

Example 3—Preparation of a Benzathine Penicillin G Mucoadhesive-Based Formulation

| Ingredient | Quantity (mg/g of formulation) |
|---|---|
| Benzathine penicillin G | 1.0 |
| Paraffin oil | 200 |

-continued

| Ingredient | Quantity (mg/g of formulation) |
|---|---|
| Trihydroxystearate | 10 |
| Cetyl dimethicon copolyol | 30 |
| Water | qs ad 1000 |
| Phosphate buffer pH 7.4 | qs pH 7.4 |

The cream-type formulation is first prepared by gently mixing benzathine penicillin G with an organic solvent. A second system is prepared by mixing paraffin oil, trihydroxystearate and cetyl dimethicon copolyol with warming to 60° C. Upon cooling to room temperature, the lipid system is mixed with the aqueous phase for 30 minutes.

Example 4—Preparation of a Ganciclovir Mucoadhesive, Thermoreversible Gel Formulation

| Ingredient | Quantity (mg/g of formulation) |
|---|---|
| Ganciclovir | 10.0 |
| Methylparaben | 1.0 |
| Poloxamer 407 | 90.0 |
| Carbopol 934P | 2.0 |
| TRIS HCl buffer (0.1M) | 397.0 |

The Carbopol 934P and Poloxamer 407 (BASF Corp.) are first suspended in the TRIS HCl buffer (0.1 M) and the components are mixed under agitation overnight at 4° C. to ensure complete dissolution. The methylparaben is added and further stirring allowed until complete dissolution is observed. Ganciclovir sodium is mixed in while maintaining stirring to produce a 2.0% ganciclovir mucoadhesive, thermoreversible gel formulation. The mixture is maintained below room temperature until use.

Example 5—Preparation of a Gentamicin Gel Formulation

| Ingredient | Quantity (mg/g of formulation) |
|---|---|
| Gentamicin | 20.0 |
| Chitosan | 20.0 |
| Glycerophosphate disodium | 80.0 |
| Water | 880 |

A 5 ml solution of acetic acid is titrated to a pH of about 4.0. The chitosan is added to achieve a pH of about 5.5. The gentamicin is then dissolved in the chitosan solution. This solution is sterilized by filtration. A 5 ml aqueous solution of glycerophosphate disodium is also prepared and sterilized. The two solutions are mixed and within 2 h at 37° C., the desired gel is formed.

Viscosity determinations of the pharmaceutical compositions described herein are performed at room temperature and 37° C. and are made using a Brookfield (spindle and cup) viscometer at 20 rpm.

Example 6—Controlled/Immediate Release Antimicrobial Formulation

| Ingredient | Quantity (mg/g of formulation) |
|---|---|
| PLA Microspheres comprising ~30% Benzathine penicillin G | 15 |
| Propylene Glycol | 30 |
| Glycerin | 20 |
| Methylcellulose (METHOCEL ® A4M) | 20 |
| Benzathine penicillin G | 10 |
| Water | qs ad 1000 |

PLA (poly(L-lactide)) microspheres comprising benzathine penicillin G are prepared by adding sufficient PLA to 100 mL dichloromethane to produce a 3% wt/vol solution. 1.29 g benzathine penicillin G is added to the solution with mixing. The solution is then added dropwise to 2 L distilled water containing 0.5% wt/vol poly(vinyl alcohol) with stirring to produce an oil/water emulsion. Stirring is continued for a sufficient period to allow evaporation of the dichloromethane and the formation of solid microspheres. Microspheres are filtered, washed with distilled water, and dried until no weight loss is observed.

The immediate release portion of the formulation is prepared by generating a 2% methylcellulose solution in a water/propylene glycol/glycerin solvent system under stirring. Benzathine penicillin G is added to the solution while stirring is continued to yield a 1% benzathine penicillin G low-viscosity gel. The appropriate amount of microspheres comprising benzathine penicillin G is then mixed with the low-viscosity gel to yield a combination controlled/immediate release benzathine penicillin G otic formulation.

Example 7—Preparation of a Thermoreversible Gel Ciprofloxacin Composition Comprising Micronized Ciprofloxacin Powder

| Ingredient | Quantity (mg/g of formulation) |
|---|---|
| ciprofloxacin | 20.0 |
| BHT | 0.002 |
| Poloxamer 407 | 160.0 |
| PBS buffer (0.1M) | 9.0 |

A 10-g batch of gel formulation containing 2.0% micronized ciprofloxacin is prepared. Micronized ciprofloxacin, 13.8 mg of sodium phosphate dibasic dihydrate USP (Fisher Scientific)+3.1 mg of sodium phosphate monobasic monohydrate USP (Fisher Scientific)+74 mg of sodium chloride USP (Fisher Scientific) is dissolved with 8.2 g of sterile filtered DI water and the pH is adjusted to 7.4 with 1 M NaOH. The buffer solution is chilled down and 1.6 g of poloxamer 407 (BASF Corp., containing approximately 100 ppm of BHT) is sprinkled into the chilled PBS solution while mixing, solution is mixed until all the poloxamer is dissolved. The poloxamer is sterile filtered using a 33 mm PVDF 0.22 μm sterile syringe filter (Millipore Corp.) and delivered to 2 mL sterile glass vials (Wheaton) in an aseptic environment, the vials are closed with sterile butyl rubber stoppers (Kimble) and crimped sealed with 13 mm Al seals (Kimble). 20 mg of micronized ciprofloxacin is placed in separate clean depyrogenated vials, the vials are closed with sterile butyl rubber stoppers (Kimble) and crimped sealed with 13 mm Al seals (Kimble), vials are dry heat sterilized (Fisher Scientific Isotemp oven) for 7 hours at 140° C. Before administration for the experiments described herein, 1 mL of the cold poloxamer solution is delivered to a vial containing 20 mg of sterile micronized ciprofloxacin using a 21G needle (Becton Dickinson) attached to a 1 mL sterile syringe (Becton Dickinson), suspension mixed well by shaking to ensure homogeneity of the suspension. The suspension is then withdrawn with the 21G syringe and the needle is switched to a 27 G needle for administration.

Formulations comprising gentamicin, azithromycin and micronized dexamethasone are prepared using the above procedure.

Example 8—Preparation of a Thermoreversible Gel Composition Comprising Micronized Ciprofloxacin Powder and Micronized Dexamethasone Powder

| Ingredient | Quantity (mg/g of formulation) |
| --- | --- |
| ciprofloxacin | 15.0 |
| dexamethasone | 15.0 |
| BHT | 0.002 |
| Poloxamer 407 | 160.0 |
| PBS buffer (0.1M) | 9.0 |

A 10-g batch of gel formulation containing 2.0% (micronized ciprofloxacin and micronized dexamethasone) is prepared. Micronized ciprofloxacin, micronized dexamethasone, 13.8 mg of sodium phosphate dibasic dihydrate USP (Fisher Scientific)+3.1 mg of sodium phosphate monobasic monohydrate USP (Fisher Scientific)+74 mg of sodium chloride USP (Fisher Scientific) is dissolved with 8.2 g of sterile filtered DI water and the pH is adjusted to 7.4 with 1 M NaOH. The buffer solution is chilled down and 1.6 g of poloxamer 407 (BASF Corp., containing approximately 100 ppm of BHT) is sprinkled into the chilled PBS solution while mixing, solution is mixed until all the poloxamer is dissolved. The poloxamer is sterile filtered using a 33 mm PVDF 0.22 µm sterile syringe filter (Millipore Corp.) and delivered to 2 mL sterile glass vials (Wheaton) in an aseptic environment, the vials are closed with sterile butyl rubber stoppers (Kimble) and crimped sealed with 13 mm Al seals (Kimble). 20 mg of micronized ciprofloxacin and micronized dexamethasone powders is placed in separate clean depyrogenated vials, the vials are closed with sterile butyl rubber stoppers (Kimble) and crimped sealed with 13 mm Al seals (Kimble), vials are dry heat sterilized (Fisher Scientific Isotemp oven) for 7 hours at 140° C. Before administration for the experiments described herein, 1 mL of the cold poloxamer solution is delivered to a vial containing 20 mg of sterile micronized ciprofloxacin and micronized dexamethasone using a 21G needle (Becton Dickinson) attached to a 1 mL sterile syringe (Becton Dickinson), suspension mixed well by shaking to ensure homogeneity of the suspension. The suspension is then withdrawn with the 21G syringe and the needle is switched to a 27 G needle for administration. I Example 9 Effect of pH on Degradation Products for Autoclaved 17% Poloxamer 407NF/2% Otic Agent in PBS Buffer A stock solution of a 17% poloxamer 407/2% otic agent is prepared by dissolving 351.4 mg of sodium chloride (Fisher Scientific), 302.1 mg of sodium phosphate dibasic anhydrous (Fisher Scientific), 122.1 mg of sodium phosphate monobasic anhydrous (Fisher Scientific) and an appropriate amount of an otic agent with 79.3 g of sterile filtered DI water. The solution is cooled down in a ice chilled water bath and then 17.05 g of poloxamer 407NF (SPECTRUM CHEMICALS) is sprinkled into the cold solution while mixing. The mixture is further mixed until the poloxamer is completely dissolved. The pH for this solution is measured.

17% poloxamer 407/2% otic agent in PBS pH of 5.3. Take an aliquot (approximately 30 mL) of the above solution and adjust the pH to 5.3 by the addition of 1 M HCl.

17% poloxamer 407/2% otic agent in PBS pH of 8.0. Take an aliquot (approximately 30 mL) of the above stock solution and adjust the pH to 8.0 by the addition of 1 M NaOH.

A PBS buffer (pH 7.3) is prepared by dissolving 805.5 mg of sodium chloride (Fisher Scientific), 606 mg of sodium phosphate dibasic anhydrous (Fisher Scientific), 247 mg of sodium phosphate monobasic anhydrous (Fisher Scientific), then QS to 200 g with sterile filtered DI water.

A 2% solution of an otic agent in PBS pH 7.3 is prepared by dissolving an appropriate amount of the otic agent in the PBS buffer and QS to 10 g with PBS buffer.

One mL samples are individually placed in 3 mL screw cap glass vials (with rubber lining) and closed tightly. The vials are placed in a Market Forge-sterilmatic autoclave (settings, slow liquids) and sterilized at 250° F. for 15 minutes. After the autoclave the samples are left to cool down to room temperature and then placed in refrigerator. The samples are homogenized by mixing the vials while cold.

Appearance (e.g., discoloration and/or precipitation) is observed and recorded. HPLC analysis is performed using an Agilent 1200 equipped with a Luna C18(2) 3 µm, 100 Å, 250×4.6 mm column) using a 30-80 acetonitrile gradient (1-10 min) of (water-acetonitrile mixture containing 0.05% TFA), for a total run of 15 minutes. Samples are diluted by taking 304, of sample and dissolved with 1.5 mL of a 1:1 acetonitrile water mixture. Purity of the otic agent in the autoclaved samples is recorded.

Formulations comprising gentamicin, ciprofloxacin and micronized dexamethasone, prepared according to the procedure above, are tested using the above procedure to determine the effect of pH on degradation during the autoclaving step.

Example 10 Effect of Autoclaving on the Release Profile and Viscosity of a 17% Poloxamer 407NF/2% Otic Agent in PBS An aliquot of a sample (autoclaved and not autoclaved) is evaluated for release profile and viscosity measurement to evaluate the impact of heat sterilization on the properties of the gel.

Dissolution is performed at 37° C. in snapwells (6.5 mm diameter polycarbonate membrane with a pore size of 0.4 µm). 0.2 mL of gel is placed into snapwell and left to harden, then 0.5 mL is placed into reservoir and shaken using a Labline orbit shaker at 70 rpm. Samples are taken every hour (0.1 mL withdrawn and replace with warm buffer). Samples are analyzed for poloxamer concentration by UV at 624 nm using the cobalt thiocyanate method, against an external calibration standard curve. In brief, 204, of the sample is mixed with 19804, of a 15 mM cobalt thiocyanate solution and absorbance measured at 625 nm, using a Evolution 160 UV/Vis spectrophotometer (Thermo Scientific).

The released otic agent is fitted to the Korsmeyer-Peppas equation $$\frac{Q}{Q_\alpha} = kt^n + b$$

where Q is the amount of otic agent released at time t, $Q_\alpha$ is the overall released amount of otic agent, k is a release constant of the nth order, n is a dimensionless number related to the dissolution mechanism and b is the axis intercept, characterizing the initial burst release mechanism wherein n=1 characterizes an erosion controlled mechanism. The mean dissolution time (MDT) is the sum of different periods of time the drug molecules stay in the matrix before release, divided by the total number of molecules and is calculated by:

$$MDT = \frac{nk^{-1/n}}{n+1}$$

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition.

Formulations comprising gentamicin, ciprofloxacin and micronized dexamethasone, prepared according to the procedures described above, are tested using the procedure described above to determine Tgel.

Example 11 Effect of Addition of a Secondary Polymer on the Degradation Products and Viscosity of a Formulation Containing 2% Otic Agent and 17% Poloxamer 407NF after Heat Sterilization (Autoclaving)

Solution A.

A solution of pH 7.0 comprising sodium carboxymethylcellulose (CMC) in PBS buffer is prepared by dissolving 178.35 mg of sodium chloride (Fisher Scientific), 300.5 mg of sodium phosphate dibasic anhydrous (Fisher Scientific), 126.6 mg of sodium phosphate monobasic anhydrous (Fisher Scientific) dissolved with 78.4 of sterile filtered DI water, then 1 g of Blanose 7M65 CMC (Hercules, viscosity of 5450 cP @ 2%) is sprinkled into the buffer solution and heated to aid dissolution, and the solution is then cooled down.

A solution of pH 7.0 comprising 17% poloxamer 407NF/1% CMC/2% otic agent in PBS buffer is made by cooling down 8.1 g of solution A in a ice chilled water bath and then adding an appropriate amount of an otic agent followed by mixing. 1.74 g of poloxamer 407NF (Spectrum Chemicals) is sprinkled into the cold solution while mixing. The mixture is further mixed until all the poloxamer is completely dissolved.

Two mL of the above sample is placed in a 3 mL screw cap glass vial (with rubber lining) and closed tightly. The vial is placed in a Market Forge-sterilmatic autoclave (settings, slow liquids) and sterilized at 250° F. for 25 minutes. After autoclaving the sample is left to cool down to room temperature and then placed in refrigerator. The sample is homogenized by mixing while the vials are cold.

Precipitation or discoloration are observed after autoclaving. HPLC analysis is performed using an Agilent 1200 equipped with a Luna C18(2) 3 μm, 100 Å, 250×4.6 mm column) using a 30-80 acetonitrile gradient (1-10 min) of (water-acetonitrile mixture containing 0.05% TFA), for a total run of 15 minutes. Samples are diluted by taking 304, of sample and dissolving with 1.5 mL of a 1:1 acetonitrile water mixture. Purity of the otic agent in the autoclaved samples is recorded.

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition.

Dissolution is performed at 37° C. for the non-autoclaved sample in snapwells (6.5 mm diameter polycarbonate membrane with a pore size of 0.4 μm), 0.2 mL of gel is placed into snapwell and left to harden, then 0.5 mL is placed into reservoir and shaken using a Labline orbit shaker at 70 rpm. Samples are taken every hour (0.1 mL withdrawn and replaced with warm buffer). Samples are analyzed for otic agent concentration by UV at 245 nm, against an external calibration standard curve.

Formulations comprising gentamicin, ciprofloxacin and micronized dexamethasone, are tested using the above procedure to determine the effect addition of a secondary polymer on the degradation products and viscosity of a formulation containing 2% otic agent and 17% poloxamer 407NF after heat sterilization (autoclaving).

Example 12 Effect of Buffer Type on the Degradation Products for Formulations Containing Poloxamer 407NF after Heat Sterilization (Autoclaving)

A TRIS buffer is made by dissolving 377.8 mg of sodium chloride (Fisher Scientific), and 602.9 mg of Tromethamine (Sigma Chemical Co.) then QS to 100 g with sterile filtered DI water, pH is adjusted to 7.4 with 1M HCl.

Stock Solution Containing 25% Poloxamer 407 Solution in TRIS Buffer:

Weigh 45 g of TRIS buffer, chill in an ice chilled bath then sprinkle into the buffer, while mixing, 15 g of poloxamer 407 NF (Spectrum Chemicals). The mixture is further mixed until all the poloxamer is completely dissolved.

A series of formulations is prepared with the above stock solution. An appropriate amount of otic agent (or salt or prodrug thereof) and/or otic agent as micronized/coated/liposomal particles (or salt or prodrug thereof) is used for all experiments.

Stock Solution (pH 7.3) Containing 25% Poloxamer 407 Solution in PBS Buffer:

PBS buffer described above is used. Dissolve 704 mg of sodium chloride (Fisher Scientific), 601.2 mg of sodium phosphate dibasic anhydrous (Fisher Scientific), 242.7 mg of sodium phosphate monobasic anhydrous (Fisher Scientific) with 140.4 g of sterile filtered DI water. The solution is cooled down in an ice chilled water bath and then 50 g of poloxamer 407NF (SPECTRUM CHEMICALS) is sprinkled into the cold solution while mixing. The mixture is further mixed until the poloxamer is completely dissolved.

A series of formulations is prepared with the above stock solution. An appropriate amount of otic agent (or salt or prodrug thereof) and/or otic agent as micronized/coated/liposomal particles (or salt or prodrug thereof) is used for all experiments.

Tables 2 and 3 list samples prepared using the procedures described above. An appropriate amount of otic agent is added to each sample to provide a final concentration of 2% otic agent in the sample.

TABLE 2

Preparation of samples containing TRIS buffer

| Sample | pH | 25% Stock Solution (g) | TRIS Buffer (g) |
| --- | --- | --- | --- |
| 20% P407/2% otic agent/TRIS | 7.45 | 8.01 | 1.82 |
| 18% P407/2% otic agent/TRIS | 7.45 | 7.22 | 2.61 |
| 16% P407/2% otic agent/TRIS | 7.45 | 6.47 | 3.42 |
| 18% P407/2% otic agent/TRIS | 7.4 | 7.18 | 2.64 |
| 4% otic agent/TRIS | 7.5 | — | 9.7 |
| 2% otic agent/TRIS | 7.43 | — | 5 |
| 1% otic agent/TRIS | 7.35 | — | 5 |
| 2% otic agent/TRIS (suspension) | 7.4 | — | 4.9 |

TABLE 3

Preparation of samples containing PBS buffer (pH of 7.3)

| Sample | 25% Stock Solution in PBS (g) | PBS Buffer (g) |
| --- | --- | --- |
| 20% P407/2% otic agent/PBS | 8.03 | 1.82 |
| 18% P407/2% otic agent/PBS | 7.1 | 2.63 |
| 16% P407/2% otic agent/PBS | 6.45 | 3.44 |
| 18% P407/2% otic agent/PBS | — | 2.63 |
| 2% otic agent/PBS | — | 4.9 |

One mL samples are individually placed in 3 mL screw cap glass vials (with rubber lining) and closed tightly. The vials are placed in a Market Forge-sterilmatic autoclave (setting, slow liquids) and sterilized at 250° F. for 25 minutes. After the autoclaving the samples are left to cool down to room temperature. The vials are placed in the refrigerator and mixed while cold to homogenize the samples.

HPLC analysis is performed using an Agilent 1200 equipped with a Luna C18(2) 3 µm, 100 Å, 250×4.6 mm column) using a 30-80 acetonitrile gradient (1-10 min) of (water-acetonitrile mixture containing 0.05% TFA), for a total run of 15 minutes. Samples are diluted by taking 30λ, of sample and dissolving with 1.5 mL of a 1:1 acetonitrile water mixture. Purity of the otic agent in the autoclaved samples is recorded. The stability of formulations in TRIS and PBS buffers is compared.

Viscosity measurements are performed using a Brookfield viscometer RVDV-II+P with a CPE-51 spindle rotated at 0.08 rpm (shear rate of 0.31 $s^{-1}$), equipped with a water jacketed temperature control unit (temperature ramped from 15-34° C. at 1.6° C./min). Tgel is defined as the inflection point of the curve where the increase in viscosity occurs due to the sol-gel transition. Only formulations that show no change after autoclaving are analyzed.

Formulations comprising gentamicin, ciprofloxacin and micronized dexamethasone, are tested using the above procedure to determine the effect addition of a secondary polymer on the degradation products and viscosity of a formulation containing 2% otic agent and 17% poloxamer 407NF after heat sterilization (autoclaving). Stability of formulations containing micronized otic agent is compared to non-micronized otic agent formulation counterparts.

Example 13: Pulsed Release Otic Formulations

A combination of ciprofloxacin and ciprofloxacin hydrochloride (ratio of 1:1) is used to prepare a pulsed release otic agent formulation using the procedures described herein. 20% of the delivered dose of ciprofloxacin is solubilized in a 17% poloxamer solution of example 9 with the aid of beta-cyclodextrins. The remaining 80% of the otic agent is then added to the mixture and the final formulation is prepared using any procedure described herein.

Pulsed release formulations comprising gentamicin, azithromycin and micronized dexamethasone, prepared according to the procedures and examples described herein, are tested using procedures described herein to determine pulse release profiles.

Example 14: Preparation of a 17% Poloxamer 407/2% Otic Agent/78 ppm Evans Blue in PBS A Stock solution of Evans Blue (5.9 mg/mL) in PBS buffer is prepared by dissolving 5.9 mg of Evans Blue (Sigma Chemical Co) with 1 mL of PBS buffer (from example 9).

A Stock solution containing 25% Poloxamer 407 solution in PBS buffer is used in this study. An appropriate amount of an otic agent is added to the stock solution to prepare formulations comprising 2% of an otic agent (Table 4).

TABLE 4

Preparation of poloxamer 407 samples containing Evans Blue

| Sample ID | 25% P407 in PBS (g) | PBS Buffer (g) | Evans Blue Solution (µL) |
| --- | --- | --- | --- |
| 17% P407/2% otic agent/EB | 13.6 | 6 | 265 |
| 20% P407/2% otic agent/EB | 16.019 | 3.62 | 265 |
| 25% P407/2% otic agent/EB | 19.63 | — | 265 |

Formulations comprising gentamicin, ciprofloxacin and micronized dexamethasone, are prepared according to the procedures described above and are sterile filtered through 0.22 µm PVDF syringe filters (Millipore corporation), and autoclaved.

The above formulations are dosed to guinea pigs in the middle ear by procedures described herein and the ability of formulations to gel upon contact and the location of the gel is identified after dosing and at 24 hours after dosing.

Example 15: Terminal Sterilization of Poloxamer 407 Formulations with and without a Visualization Dye 17% poloxamer407/2% otic agent/in phosphate buffer, pH 7.3:

Dissolve 709 mg of Sodium chloride (Fisher Scientific), 742 mg of sodium phosphate dibasic dehydrate USP (Fisher Scientific), 251.1 mg of sodium phosphate monobasic monohydrate USP (Fisher Scientific) and an appropriate amount of an otic agent with 158.1 g of sterile filtered DI water. The solution is cooled down in an ice chilled water bath and then 34.13 g of poloxamer 407NF (Spectrum chemicals) is sprinkled into the cold solution while mixing. The mixture is further mixed until the poloxamer is completely dissolved.

17% Poloxamer407/2% Otic Agent/59 ppm Evans Blue in Phosphate Buffer:

Take two mL of the 17% poloxamer407/2% otic agent/in phosphate buffer solution and add 2 mL of a 5.9 mg/mL Evans blue (Sigma-Aldrich chemical Co) solution in PBS buffer.

25% Poloxamer407/2% Otic Agent/in Phosphate Buffer:

Dissolve 330.5 mg of sodium chloride (Fisher Scientific), 334.5 mg of sodium phosphate dibasic dehydrate USP (Fisher Scientific), 125.9 mg of sodium phosphate monobasic monohydrate USP (Fisher Scientific) and an appropriate amount of an otic agent with 70.5 g of sterile filtered DI water.

The solution is cooled down in an ice chilled water bath and then 25.1 g of poloxamer 407NF (Spectrum chemicals) is sprinkled into the cold solution while mixing. The mixture is further mixed until the poloxamer is completely dissolved.

25% Poloxamer407/2% Otic Agent/59 ppm Evans Blue in Phosphate Buffer:

Take two mL of the 25% poloxamer407/2% otic agent/in phosphate buffer solution and add 2 mL of a 5.9 mg/mL Evans blue (Sigma-Aldrich chemical Co) solution in PBS buffer.

Place 2 mL of formulation into a 2 mL glass vial (Wheaton serum glass vial) and seal with 13 mm butyl str (kimble stoppers) and crimp with a 13 mm aluminum seal. The vials are placed in a Market Forge-sterilmatic autoclave (settings, slow liquids) and sterilized at 250° F. for 25 minutes. After the autoclaving the samples are left to cool down to room temperature and then placed in refrigeration. The vials are placed in the refrigerator and mixed while cold to homogenize the samples. Sample discoloration or precipitation after autoclaving is recorded.

HPLC analysis is performed using an Agilent 1200 equipped with a Luna C18(2) 3 μm, 100 Å, 250×4.6 mm column) using a 30-95 methanol:acetate buffer pH 4 gradient (1-6 min), then isocratic for 11 minutes, for a total run of 22 minutes. Samples are diluted by taking 304, of sample and dissolved with 0.97 mL of water. The main peaks are recorded. Purity before autoclaving is greater than 99% using this method.

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min). Tgel is defined as the inflection point of the curve where the increase in viscosity occurs due to the sol-gel transition.

Formulations comprising gentamicin, ciprofloxacin and micronized dexamethasone, prepared according to the procedures described herein, are tested using the above procedures to determine stability of the formulations.

Example 16: In Vitro Comparison of Release Profile

Dissolution is performed at 37° C. in snapwells (6.5 mm diameter polycarbonate membrane with a pore size of 0.4 μm), 0.2 mL of a gel formulation described herein is placed into snapwell and left to harden, then 0.5 mL buffer is placed into reservoir and shaken using a Labline orbit shaker at 70 rpm. Samples are taken every hour (0.1 mL withdrawn and replace with warm buffer). Samples are analyzed for otic agent concentration by UV at 245 nm against an external calibration standard curve. Pluronic concentration is analyzed at 624 nm using the cobalt thiocyanate method. Relative rank-order of mean dissolution time (MDT) as a function of % P407 is determined. A linear relationship between the formulations mean dissolution time (MDT) and the P407 concentration indicates that the otic agent is released due to the erosion of the polymer gel (poloxamer) and not via diffusion. A non-linear relationship indicates release of otic agent via a combination of diffusion and/or polymer gel degradation.

Alternatively, samples are analyzed using the method described by Li Xin-Yu paper [Acta Pharmaceutica Sinica 2008,43(2):208-203] and Rank-order of mean dissolution time (MDT) as a function of % P407 is determined.

Formulations comprising gentamicin, ciprofloxacin and micronized dexamethasone, prepared according to the procedures described herein, are tested using the above procedure to determine the release profile of the otic agents.

Example 17: In Vitro Comparison of Gelation Temperature

The effect of Poloxamer 188 and an otic agent on the gelation temperature and viscosity of Poloxamer 407 formulations is evaluated with the purpose of manipulating the gelation temperature.

A 25% Poloxamer 407 stock solution in PBS buffer and the PBS solution described above are used. Poloxamer 188NF from BASF is used. An appropriate amount of otic agent is added to the solutions described in Table 5 to provide a 2% formulation of the otic agent.

TABLE 5

Preparation of samples containing poloxamer 407/poloxamer 188

| Sample | 25% P407 Stock Solution (g) | Poloxamer 188 (mg) | PBS Buffer (g) |
| --- | --- | --- | --- |
| 16% P407/10% P188 | 3.207 | 501 | 1.3036 |
| 17% P407/10% P188 | 3.4089 | 500 | 1.1056 |
| 18% P407/10% P188 | 3.6156 | 502 | 0.9072 |
| 19% P407/10% P188 | 3.8183 | 500 | 0.7050 |
| 20% P407/10% P188 | 4.008 | 501 | 0.5032 |
| 20% P407/5% P188 | 4.01 | 256 | 0.770 |

Mean dissolution time, viscosity and gel temperature of the above formulations are measured using procedures described herein.

An equation is fitted to the data obtained and can be utilized to estimate the gelation temperature of F127/F68 mixtures (for 17-20% F127 and 0-10% F68).

$$T_{gel}=-1.8(\% \, F127)+1.3(\% \, F68)+53$$

An equation is fitted to the data obtained and can be utilized to estimate the Mean Dissolution Time (hr) based on the gelation temperature of F127/F68 mixtures (for 17-25% F127 and 0-10% F68), using results obtained in examples above.

$$MDT=-0.2(T_{gel})+8$$

Formulations comprising gentamicin, ciprofloxacin and micronized dexamethasone, are prepared by addition of an appropriate amount of otic agents to the solutions described in Table 5. The gel temperature of the formulations is determined using the procedure described above.

Example 18: Determination of Temperature Range for Sterile Filtration

The viscosity at low temperatures is measured to help guide the temperature range at which the sterile filtration needs to occur to reduce the possibility of clogging.

Viscosity measurements are performed using a Brookfield viscometer RVDV-II+P with a CPE-40 spindle rotated at 1, 5 and 10 rpm (shear rate of 7.5, 37.5 and 75 s$^{-1}$), equipped with a water jacketed temperature control unit (temperature ramped from 10-25° C. at 1.6° C./min).

The Tgel of a 17% Pluronic P407 is determined as a function of increasing concentration of otic agent. The increase in Tgel for a 17% pluronic formulation is estimated by:

$$\Delta T_{gel}=0.93[\% \text{ otic agent}]$$

Formulations comprising gentamicin, ciprofloxacin and micronized dexamethasone, prepared according to procedures described herein, are tested using the above procedure to determine the temperature range for sterile filtration. The effect of addition of increased amounts of otic agent on the Tgel, and the apparent viscosity of the formulations is recorded.

Example 19: Determination of Manufacturing Conditions

TABLE 6

Viscosity of potential formulations at manufacturing/filtration conditions.

| | Apparent Viscosity$^a$ (cP) | | |
|---|---|---|---|
| Sample | 5° C. below Tgel | 20° C. | Temperature @ 100 cP |
| Placebo | 52 cP @ 17° C. | 120 cP | 19° C. |
| 17% P407/ 2% otic agent | 90 cP @ 18° C. | 147 cP | 18.5° C. |
| 17% P407/ 6% otic agent | 142 cP @ 22° C. | 105 cP | 19.7° C. |

$^a$Viscosity measured at a shear rate of 37.5 s$^{-1}$

An 8 liter batch of a 17% P407 placebo is manufactured to evaluate the manufacturing/filtration conditions. The placebo is manufactured by placing 6.4 liters of DI water in a 3 gallon SS pressure vessel, and left to cool down in the refrigerator overnight. The following morning the tank is taken out (water temperature 5° C., RT 18° C.) and 48 g of sodium chloride, 29.6 g of sodium phosphate dibasic dehydrate and 10 g of sodium phosphate monobasic monohydrate is added and dissolved with an overhead mixer (IKA RW20 @ 1720 rpm). Half hour later, once the buffer is dissolved (solution temperature 8° C., RT 18° C.), 1.36 kg of poloxamer 407 NF (spectrum chemicals) is slowly sprinkled into the buffer solution in a 15 minute interval (solution temperature 12° C., RT 18° C.), then speed is increased to 2430 rpm. After an additional one hour mixing, mixing speed is reduced to 1062 rpm (complete dissolution).

The temperature of the room is maintained below 25° C. to retain the temperature of the solution at below 19° C. The temperature of the solution is maintained at below 19° C. up to 3 hours of the initiation of the manufacturing, without the need to chill/cool the container.

Three different Sartoscale (Sartorius Stedim) filters with a surface area of 17.3 cm$^2$ are evaluated at 20 psi and 14° C. of solution
1) Sartopore 2, 0.2 µm 5445307HS-FF (PES), flow rate of 16 mL/min
2) Sartobran P, 0.2 µm 5235307HS-FF (cellulose ester), flow rate of 12 mL/min
3) Sartopore 2 XLI, 0.2 µm 54453071S-FF (PES), flow rate of 15 mL/min Sartopore 2 filter 5441307H4-SS is used, filtration is carried out at the solution temperature using a 0.45, 0.2 µm Sartopore 2 150 sterile capsule (Sartorius Stedim) with a surface area of 0.015 m$^2$ at a pressure of 16 psi. Flow rate is measured at approximately 100 mL/min at 16 psi, with no change in flow rate while the temperature is maintained in the 6.5-14° C. range. Decreasing pressure and increasing temperature of the solution causes a decrease in flow rate due to an increase in the viscosity of the solution. Discoloration of the solution is monitored during the process.

TABLE 7

Predicted filtration time for a 17% poloxamer 407 placebo at a solution temperature range of 6.5-14° C. using Sartopore 2, 0.2 µm filters at a pressure of 16 psi of pressure.

| Filter (mL/min) | Size (m$^2$) | Estimated flow rate (mL/min) | Time to filter 8 L (estimated) |
|---|---|---|---|
| Sartopore 2, size 4 | 0.015 | 100 mL/min | 80 min |
| Sartopore 2, size 7 | 0.05 | 330 mL/min | 24 min |
| Sartopore 2, size 8 | 0.1 | 670 mL/min | 12 min |

Viscosity, Tgel and UV/Vis absorption is checked before filtration evaluation. Pluronic UV/Vis spectra are obtained by a Evolution 160 UV/Vis (Thermo Scientific). A peak in the range of 250-300 nm is attributed to BHT stabilizer present in the raw material (poloxamer). Table 8 lists physicochemical properties of the above solutions before and after filtration.

TABLE 8

Physicochemical properties of 17% poloxamer 407 placebo solution before and after filtration

| Sample | Tgel (° C.) | Viscosity$^a$ @ 19° C. (cP) | Absorbance @ 274 nm |
|---|---|---|---|
| Before filtration | 22 | 100 | 0.3181 |
| After filtration | 22 | 100 | 0.3081 |

$^a$Viscosity measured at a shear rate of 37.5 s$^{-1}$

The above process is applicable for manufacture of 17% P407 formulations, and includes temperature analysis of the room conditions. Preferably, a maximum temperature of 19° C. reduces cost of cooling the container during manufacturing. In some instances, a jacketed container is used to further control the temperature of the solution to ease manufacturing concerns.

Example 20 In Vitro Release of Otic Agent from an Autoclaved Micronized Sample

17% poloxamer 407/1.5% otic agent in TRIS buffer: 250.8 mg of sodium chloride (Fisher Scientific), and 302.4 mg of Tromethamine (Sigma Chemical Co.) is dissolved in 39.3 g of sterile filtered DI water, pH is adjusted to 7.4 with 1M HCl. 4.9 g of the above solution is used and an appropriate amount of micronized otic agent is suspended and dispersed well. 2 mL of the formulation is transferred into a 2 mL glass vial (Wheaton serum glass vial) and sealed with 13 mm butyl styrene (kimble stoppers) and crimped with a 13 mm aluminum seal. The vial is placed in a Market Forge-sterilmatic autoclave (settings, slow liquids) and sterilized at 250° F. for 25 minutes. After the autoclaving the sample is left to cool down to room temperature. The vial is placed in the refrigerator and mixed while cold to homogenize the sample. Sample discoloration or precipitation after autoclaving is recorded.

Dissolution is performed at 37° C. in snapwells (6.5 mm diameter polycarbonate membrane with a pore size of 0.4 µm), 0.2 mL of gel is placed into snapwell and left to harden, then 0.5 mL PBS buffer is placed into reservoir and shaken using a Labline orbit shaker at 70 rpm. Samples are taken every hour [0.1 mL withdrawn and replaced with warm PBS buffer containing 2% PEG-40 hydrogenated castor oil (BASF) to enhance otic agent solubility]. Samples are analyzed for otic agent concentration by UV at 245 nm against an external calibration standard curve. The release rate is compared to other formulations disclosed herein. MDT time is calculated for each sample.

Solubilization of otic agent in the 17% poloxamer system is evaluated by measuring the concentration of the otic agent in the supernatant after centrifuging samples at 15,000 rpm for 10 minutes using an eppendorf centrifuge 5424. Otic agent concentration in the supernatant is measured by UV at 245 nm against an external calibration standard curve.

Formulations comprising gentamicin, ciprofloxacin and micronized dexamethasone, prepared according to the procedures described herein, are tested using the above procedures to determine release rate of the otic agent from each formulation.

Example 21: Release Rate or MDT and Viscosity of Formulation Containing Sodium Carboxymethyl Cellulose 17% Poloxamer 407/2% Otic Agent/1% CMC (Hercules Blanose 7M):

A sodium carboxymethylcellulose (CMC) solution (pH 7.0) in PBS buffer is prepared by dissolving 205.6 mg of sodium chloride (Fisher Scientific), 372.1 mg of sodium phosphate dibasic dihydrate (Fisher Scientific), 106.2 mg of sodium phosphate monobasic monohydrate (Fisher Scientific) in 78.1 g of sterile filtered DI water. 1 g of Blanose 7M CMC (Hercules, viscosity of 533 cP @ 2%) is sprinkled into the buffer solution and heated to ease solution, solution is then cooled down and 17.08 g poloxamer 407NF (Spectrum Chemicals) is sprinkled into the cold solution while mixing. A formulation comprising 17% poloxamer 407NF/1% CMC/2% otic agent in PBS buffer is made adding/dissolving an appropriate amount of otic agent to 9.8 g of the above solution, and mixing until all the otic agent is completely dissolved.

17% Poloxamer 407/2% Otic Agent/0.5% CMC (Blanose 7M65):

A sodium carboxymethylcellulose (CMC) solution (pH 7.2) in PBS buffer is prepared by dissolving 257 mg of sodium chloride (Fisher Scientific), 375 mg of sodium phosphate dibasic dihydrate (Fisher Scientific), 108 mg of sodium phosphate monobasic monohydrate (Fisher Scientific) in 78.7 g of sterile filtered DI water. 0.502 g of Blanose 7M65 CMC (Hercules, viscosity of 5450 cP @ 2%) is sprinkled into the buffer solution and heated to ease solution, solution is then cooled down and 17.06 g poloxamer 407NF (Spectrum Chemicals) is sprinkled into the cold solution while mixing. A 17% poloxamer 407NF/1% CMC/2% otic agent solution in PBS buffer is made adding/dissolving an appropriate amount of otic agent to 9.8 g of the above solution, and mixing until the otic agent is completely dissolved.

17% poloxamer 407/2% otic agent/0.5% CMC (Blanose 7H9): A sodium carboxymethylcellulose (CMC) solution (pH 7.3) in PBS buffer is prepared by dissolving 256.5 mg of sodium chloride (Fisher Scientific), 374 mg of sodium phosphate dibasic dihydrate (Fisher Scientific), 107 mg of sodium phosphate monobasic monohydrate (Fisher Scientific) in 78.6 g of sterile filtered DI water, then 0.502 g of Blanose 7H9 CMC (Hercules, viscosity of 5600 cP @ 1%) is sprinkled to the buffer solution and heated to ease solution, solution is then cooled down and 17.03 g poloxamer 407NF (Spectrum Chemicals) is sprinkled into the cold solution while mixing. A 17% poloxamer 407NF/1% CMC/ 2% otic agent solution in PBS buffer is made adding/ dissolving an appropriate amount of otic agent to 9.8 of the above solution, and mixing until the otic agent is completely dissolved.

Viscosity measurements are performed using a Brookfield viscometer RVDV-II+P with a CPE-40 spindle rotated at 0.08 rpm (shear rate of 0.6 s$^{-1}$), equipped with a water jacketed temperature control unit (temperature ramped from 10-34° C. at 1.6° C./min). Tgel is defined as the inflection point of the curve where the increase in viscosity occurs due to the sol-gel transition.

Dissolution is performed at 37° C. in snapwells (6.5 mm diameter polycarbonate membrane with a pore size of 0.4 µm). 0.2 mL of gel is placed into snapwell and left to harden, then 0.5 mL PBS buffer is placed into reservoir and shaken using a Labline orbit shaker at 70 rpm. Samples are taken every hour, 0.1 mL withdrawn and replaced with warm PBS buffer. Samples are analyzed for otic agent concentration by UV at 245 nm against an external calibration standard curve. The release rate is compared to the formulations disclosed in above examples, and MDT time is calculated for each of the above formulations.

Formulations comprising gentamicin, ciprofloxacin and micronized dexamethasone, prepared according to procedures described above, are tested using the above procedures to determine relationship between release rate and/or mean dissolution time and viscosity of formulation containing sodium carboxymethyl cellulose. Any correlation between the mean dissolution time (MDT) and the apparent viscosity (measured at 2° C. below the gelation temperature) is recorded.

Example 22 Effect of Poloxamer Concentration and Otic Agent Concentration on Release Kinetics A series of compositions comprising varying concentrations of a gelling agent and micronized dexamethasone was prepared using procedures described above. The mean dissolution time (MDT) for each composition in Table 9 was determined using procedures described above.

TABLE 9

Preparation of poloxamer/otic agent compositions

| Sample | pH | MDT |
|---|---|---|
| 15.5% P407/1.5% dexamethasone/PBS | 7.4 | 46 h |
| 16% P407/1.5% dexamethasone/PBS | 7.4 | 40 h |
| 17% P407/1.5% dexamethasone/PBS | 7.4 | 39 h |
| 15.5% P407/4.5% dexamethasone/PBS | 7.4 | >7 days |
| 16% P407/4.5% dexamethasone/PBS | 7.4 | >7 days |
| 17% P407/4.5% dexamethasone/PBS | 7.4 | >7 days |

The effect of gel strength and otic agent concentration on release kinetics of an otic agent from the composition or device was determined by measurement of the MDT for poloxamer, and measurement of MDT for otic agent. The half life of the otic agent and mean residence time of the otic agent was also determined for each formulation by measurement of concentration of the otic agent in the perilymph using procedures described herein.

The apparent viscosity of each composition was measured as described above. A thermoreversible polymer gel concentration of about 15.5% in a composition or device described above provided an apparent viscosity of about 270,000 cP. A thermoreversible polymer gel concentration of about 16% in a composition or device described above provided an apparent viscosity of about 360,000 cP. A thermoreversible polymer gel concentration of about 17% in a composition or device described above provided an apparent viscosity of about 480,000 cP.

Compositions comprising gentamicin, ciprofloxacin and amoxicillin, prepared according to the procedures described above are tested using the above procedure to determine release rate of the otic agent from each composition.

Example 23—Application of an Enhanced Viscosity Antimicrobial Agent Formulation onto the Round Window Membrane A formulation according to Example 7 is prepared and loaded into 5 ml siliconized glass syringes attached to a 15-gauge luer lock disposable needle. Lidocaine is topically applied to the tympanic membrane, and a small incision made to allow visualization into the middle ear cavity. The needle tip is guided into place over the round window membrane, and the antimicrobial agent formulation applied directly onto the round-window membrane.

Example 24—In Vivo Testing of Intratympanic Injection of Antimicrobial Agent Formulation in a Guinea Pig A cohort of 21 guinea pigs (Charles River, females weighing 200-300 g) is intratympanically injected with 50 µL of different P407-otic agent formulations described herein, containing 0 to 50% otic agent. The gel elimination time course for each formulation is determined. A faster gel elimination time course of a formulation indicates lower mean dissolution time (MDT). Thus the injection volume and the concentration of an antimicrobial agent in a formulation are tested to determine optimal parameters for preclinical and clinical studies.

Example 25—In Vivo Extended Release Kinetics

A cohort of 21 guinea pigs (Charles River, females weighing 200-300 g) is intratympanically injected with 50 µL 17% Pluronic F-127 formulation buffered at 280 mOsm/kg and containing 1.5% to 35% antimicrobial agent by weight of the formulation. Animals are dosed on day 1. The release profile for the formulations is determined based on analysis of the perilymph.

Example 26—Evaluation of Antimicrobial Agent Formulations in an AIED Animal Model Methods and Materials
Induction of Immune Response Female albino National Institutes of Health-Swiss mice (Harlan Sprague-Dawley, Inc., Indianapolis, Inc.) weighing 20 to 24 g are used. Keyhole limpet hemocyanin (KLH; Pacific Biomarine Supply Co., Venice, Calif.) is suspended in phosphate-buffered saline (PBS) IpH 6.4), dialyzed aseptically against PBS and centrifuged twice. The precipitate (associated KLH) is dissolved in PBS and injected subcutaneously in the back of the animal (0.2 mg emulsified in Freund's complete adjuvant). The animals are given a booster (0.2 mg KLH in Freund's incomplete adjuvant, and then injected ten weeks later with 0.1 mg KLH in 5 µl PBS (pH 6.4) through a microhole drilled through the cochlear capsule. The cochlea is approached using an operating microscope and sterile technique. A postauricular incision is made, and a hole is drilled into the bullae to allow good visualization of the promontory of the cochlear basal turn, stapedial artery, and round window niche. The stapedial artery is cauterized and removed, and a 25 µm hole is drilled through the cochlear capsule into the scala tympani of the lateral basal turn. KLH or PBS control is slowly injected using a Hamilton syringe coupled with a plastic tube to a glass micropipette filled with the antigen or control. The hole is sealed with bone wax after injection, and excess fluid is removed. Only one cochlea per animal is treated with KLH.

Treatment

KLH and control mice are sorted into two groups (n=10 in each group). The antimicrobial agent formulation of Example 4 is applied to the round window membrane of one group of animals. Control formulation containing no ganciclovir is applied to the second group. The antimicrobial agent and control formulations are reapplied three days after the initial application. The animals are sacrificed after the seventh day of treatment.

Analysis of Results
Electrophysiologic Testing

The hearing threshold for the auditory brainstem response threshold (ABR) to click stimuli for each ear of each animal is initially measured and 1 week after the experimental procedure. The animals are placed in a single-walled acoustic booth (Industrial Acoustics Co, Bronx, N.Y., USA) on a heating pad. Subdermal electrodes (Astro-Med, Inc. Grass Instrument Division, West Warwick, R.I., USA) were inserted at the vertex (active electrode), the mastoid (reference), and the hind leg (ground). Click stimuli (0.1 millisecond) are computer generated and delivered to a Beyer DT 48, 200 Ohm speaker fitted with an ear speculum for placement in the external auditory meatus. The recorded ABR is amplified and digitized by a battery-operated pre-amplifier and input to a Tucker-Davis Technologies ABR recording system that provides computer control of the stimulus, recording, and averaging functions (Tucker Davis Technology, Gainesville, Fla., USA). Successively decreasing amplitude stimuli are presented in 5-dB steps to the animal, and the recorded stimulus-locked activity is averaged (n=512) and displayed. Threshold is defined as the stimulus level between the record with no visibly detectable response and a clearly identifiable response.

Histochemical Analysis

Animals are anesthetized and sacrificed via intracardiac perfusion of heparinized warm saline followed by approximately 40 ml periodate-lysine-paraformaldehyde (4% paraformaldehyde final concentration) fixative. Right-side temporal bones are immediately removed and decalcified with buffered 5% ethylenediamine tetra-acetate (pH 7.2) for 14 days (4° C.). After decalcification, temporal bones are immersed sequentially in increasing concentrations (50%, 75%, 100%) of optimal cutting temperature (OCT) compound (Tissue-Tek, Miles Inc., Elkhart, Ind.), snap-frozen (−70° C.), and cryostat-sectioned (4 μm) parallel to the modiolus. Sections are collected for hematoxylin and eosin (H&E) staining and immunohistochemical analysis.

The severity of inflammation is assessed according to the amount of cellular infiltration of the scala tympani, and an unbiased score is given to each cochlea. A score of 0 indicates no inflammation, and a score of 5 indicates that all cochlear turns had severe infiltration of inflammatory cells.

Example 27—Evaluation of Antimicrobial Agent Formulations in an Otitis Media Animal Model Induction of Otitis Media Healthy adult chinchillas weight 400 to 600 g with normal middle ears, ascertained by otoscopy and tympanometry are used for these studies. Eustachian tube obstruction is performed 24 hours before inoculation to prevent the inoculum from flowing out of the eustachian tube. One milliliter of type 3 *S. pneumoniae* strain at 4-h-log phase (containing approximately 40 colony forming units (CFU)) is placed directly into both middle ear hypotympanic bullae of the chinhillas. Control mice are inoculated with one milliliter sterile PBS.

Treatment

*S. pneumoniae* inoculated and control mice are sorted into two groups (n=10 in each group). The antimicrobial agent formulation of Example 1 containing amoxicillin is applied to the walls of the tympanic cavity of one group of animals. Control formulation containing no amoxicillin is applied to the second group. The amoxicillin and control formulations are reapplied three days after the initial application. The animals are sacrificed after the seventh day of treatment.

Analysis of Results

Auris media ear fluid (MEF) is sampled at 1, 2, 6, 12, 24, 48 and 72 hours after pneumoccal inocualtion. Quantitative MEF cultures are performed on sheep blood agar, with the quantitation threshold set at 50 CFU/ml. Inflammatory cells are quantitated with a hemocytometer, and differential cell enumeration performed with Wright's staining.

Example 28—Evaluation of Antimicrobial Agent Formulations in an Otitis Externa Animal Model Otitis externa is induced in 20 Sprague-Dawley rats using a plastic pipette to aggravate the tissue of the ear canal. All of the rats develop OE within one day. The antimicrobial formulation of Example 2 containing neomycin is administered to the ears of half of the rats using a needle and syringe, while the remaining rats receive the same formulation without the neomycin. The ear canal tissue is observed for redness and swelling that characterizes the condition. Light microscopy is used to analyze biopsy samples from the rats.

Example 29—Clinical Trial of Antimicrobial Agent Formulations for the Treatment of Otosyphilis Patients selected for the study present symptoms of cochleovestibular dysfunction and positive syphilis serology. Patients are divided into two groups, a test group receiving intratympanic administration of the formulation of Example 6 in conjunction with an intramuscular (IM) injection of 2.4 million units of benzathine penicillin G (the recommended treatment for syphilis), and a control group receiving only the carrier and microspheres of the otic formulation of Example 6 in conjunction with an IM injection of 2.4 million units of benzathine penicillin G. Patients are monitored for improvement of hearing, tinnitus, vertigo, and nystagmus following administration of the active agents. The primary outcome of the trial is improvement of cochleovestibular function at the 6 month post-treatment visit. The outcome for patients receiving the formulation of Example 6 and the recommended therapy is compared to the outcome for patients receiving only the carrier for the otic formulation and the recommended therapy in order to determine the efficacy of localized delivery of an antimicrobial agent formulation for the treatment of otic symptoms of syphilis.

Example 30—Clinical Trial of Antimicrobial Agent Formulations in Combination with Tympanostomy for Treatment of Otitis Media with Effusion The purpose of this study is to determine if a composition comprising a combination of Ciprofloxacin and Dexamethasone administered in combination with a tympanostomy is safe and effective in preventing and/or treating middle ear infections in patients with ear tubes.

Study Type:

Interventional

Study Design:

This will be a non-inferiority open label study to compare the current standard of care versus the use of extended release intratympanic compositions in combination with tympanostomy. The current standard of care requires the use of otic drops for 5-7 days post-surgery. The study is designed to test whether administration of a sustained release composition at the time of surgery obviates the need for outpatient treatment. The test hypothesis is that administration of a single injection of an extended release composition at the time of surgery is not inferior to administration of otic drops after surgery.

Inclusion Criteria:

6 months to 12 years old, Acute Otitis Media with effusion in one or both ears

Patient may not have had otic surgery other than tube placement in the last year Patient may not have any disease or condition that would negatively affect the conduct of the study Patient may not require any other systemic antimicrobial therapy during the study.
Analgesic use (other than acetaminophen) is not allowed
Patient may not be pre-disposed to neurosensory hearing loss
Exclusion Criteria:
Age
Study Protocol:
Twenty patients will be divided into two groups. The first group of patients will receive an injection of an extended release composition comprising micronized ciprofloxacin and micronized dexamethasone during the surgical procedure. Each patient will undergo a tympanostomy for placement of a tube. During the surgical procedure, the surgeon will clean the ear of all effusion and while the myngotomoy incision is open, the surgeon injects a test composition into the middle ear space. The tube is inserted after injection of the extended release composition into the middle ear space. The test composition is either prepared in the operating room by suspending dry micronized powder of ciprofloxacin and dexamethasone with other excipients, or the test composition is a prepared suspension ready for injection.

The second group of patients will be given ear drops comprising non-micronized ciprofloxacin and non-micronized dexamethasone as immediate release components to be administered for 5-7 days after the surgery.

Patients are monitored with weekly follow up visits for one month. Any differences in treatment outcomes between the two groups are recorded.

Primary Outcome Measures:
Time to cessation of otorrhea as recorded by the parent or guardian via a patient.
Secondary Outcome Measures:
Clinical cure rate; Microbiological outcome; Treatment failures; Recurrence of disease.

The treatment outcome for each group of patients is compared to determine whether administration of the extended release composition comprising ciprofloxacin and dexamethasone in combination with tympanostomy is no worse than administration of ear drops comprising ciprofloxacin and dexamethasone after surgery for reduction of otorrhea, infections, or inflammation associated with tympanostomy.

While preferred embodiments of the present invention have been shown and described herein, such embodiments are provided by way of example only. Various alternatives to the embodiments described herein are optionally employed in practicing the inventions. It is intended that the following claims define the scope of the invention and that methods and structures within the scope of these claims and their equivalents be covered thereby.

We claim:

1. An otic pharmaceutical composition for use in the treatment of an otic disease or condition, comprising an auris acceptable hydrogel and a micronized and non-microencapsulated antimicrobial agent, wherein the composition is free of corticosteroid, wherein the composition is free of preservative, and wherein the composition provides sustained release of the antimicrobial agent into the ear for a period of at least 5 days, and wherein the antimicrobial agent is an antibiotic selected from a sulfonamide, a penicillin, a quinolone, a cephalosporin, or a macrolide antibiotic.

2. The composition of claim 1, wherein the composition is injectable with a needle having a gauge in the range of 18-31.

3. The composition of claim 1, wherein the composition has a viscosity between about 15,000 cP and about 1,000,000 cP.

4. The composition of claim 1, wherein the composition has a pH of about 7.0 to about 8.0.

5. The composition of claim 1, wherein the antibiotic is a quinolone selected from ciprofloxacin, enoxacin, gatifloxacin, levofloxacin, lomefloxacin, moxifloxacin, norfloxacin, ofloxacin, trovafloxacin, grepafloxacin, sparfloxacin, AL-15469A, and AL-38905.

6. The composition of claim 1, wherein the otic disease or condition is otitis media.

7. The composition of claim 1, wherein the otic disease or condition is otitis media with effusion.

8. The composition of claim 1, wherein the otic disease or condition is swimmer's ear.

9. The composition of claim 1, wherein the antibiotic is ciprofloxacin.

* * * * *